(12) United States Patent
Guo et al.

(10) Patent No.: US 10,378,018 B2
(45) Date of Patent: Aug. 13, 2019

(54) RNA-BASED COMPOSITIONS AND ADJUVANTS FOR PROPHYLACTIC AND THERAPEUTIC TREATMENT

(71) Applicant: UNIVERSITY OF KENTUCKY RESEARCH FOUNDATION, Lexington, KY (US)

(72) Inventors: Peixuan Guo, Lexington, KY (US); Hui Li, Lexington, KY (US); Emil Khisamutdinov, Lexington, KY (US); Daniel Jasinski, Lexington, KY (US)

(73) Assignee: UNIVERSITY OF KENTUCKY RESEARCH FOUNDATION, Lexington, KY (US)

(*) Notice: Subject to any disclaimer, the term of this patent is extended or adjusted under 35 U.S.C. 154(b) by 0 days.

(21) Appl. No.: 15/383,575

(22) Filed: Dec. 19, 2016

(65) Prior Publication Data

US 2017/0175122 A1 Jun. 22, 2017

Related U.S. Application Data

(63) Continuation-in-part of application No. PCT/US2015/036798, filed on Jun. 19, 2015.

(60) Provisional application No. 62/014,503, filed on Jun. 19, 2014.

(51) Int. Cl.
| | |
|---|---|
| *C07H 21/04* | (2006.01) |
| *C12N 15/117* | (2010.01) |
| *A61K 39/39* | (2006.01) |
| *A61K 39/00* | (2006.01) |

(52) U.S. Cl.
CPC ............ *C12N 15/117* (2013.01); *A61K 39/39* (2013.01); *A61K 2039/55561* (2013.01); *A61K 2039/6025* (2013.01); *A61K 2039/64* (2013.01); *C12N 2310/17* (2013.01); *C12N 2310/3519* (2013.01); *C12N 2310/52* (2013.01)

(58) Field of Classification Search
None
See application file for complete search history.

(56) References Cited

U.S. PATENT DOCUMENTS

| | | |
|---|---|---|
| 2009/0081157 A1 | 3/2009 | Kornbluth et al. |
| 2011/0244025 A1 | 10/2011 | Uhlmann et al. |
| 2014/0135487 A1 | 5/2014 | Lipford et al. |

FOREIGN PATENT DOCUMENTS

| | | |
|---|---|---|
| WO | 2003/086280 | 10/2003 |
| WO | 2005/003293 | 1/2005 |
| WO | 2012/170372 | 12/2012 |
| WO | 20130119676 | 8/2013 |

OTHER PUBLICATIONS

Zhou et al. (Pharmaceuticals 2013, 6(1), 85-107).*
Brannon-Peppas et al. (Advanced Drug Delivery Reviews 2012: 206-212).*
Ohno, Hirohisa, et al. "Synthetic RNA-protein complex shaped like an equilateral triangle." Nature nanotechnology 6.2 (2011): 116-120.
Petrov, Anton I., Craig L. Zirbel, and Neocles B. Leontis. "WebFR3D—a server for finding, aligning and analyzing recurrent RNA 3D motifs." Nucleic acids research 39.suppl_2 (2011): W50-W55.
Ponchon, Luc, and Frédéric Dardel. "Recombinant RNA technology: the tRNA scaffold." Nature methods 4.7 (2007): 571-576.
Reif, Randall, Farzin Hague, and Peixuan Guo. "Fluorogenic RNA nanoparticles for monitoring RNA folding and degradation in real time in living cells." Nucleic acid therapeutics 22.6 (2012): 428-437.
Saha, Asim, et al. "CpG oligonucleotides enhance the tumor antigen-specific immune response of an anti-idiotype antibody-based vaccine strategy in CEA transgenic mice." Cancer Immunology, Immunotherapy 55.5 (2006): 515-527.
Sandler, Anthony D., et al. "CpG oligonucleotides enhance the tumor antigen-specific immune response of a granulocyte macrophage colony-stimulating factor-based vaccine strategy in neuroblastoma." Cancer research 63.2 (2003): 394-399.
Severcan, Isil, et al. "A polyhedron made of tRNAs." Nature chemistry 2.9 (2010): 772-779.
Severcan, Isil, et al. "Square-shaped RNA particles from different RNA folds." Nano letters 9.3 (2009): 1270-1277.
Shapiro, Bruce A., et al. "Protocols for the in silico design of RNA nanostructures." Nanostructure Design: Methods and Protocols (2008): 93-115.
Shu, Dan, et al. "Bottom-up assembly of RNA arrays and superstructures as potential parts in nanotechnology." Nano letters 4.9 (2004): 1717-1723.
Shu, Dan, et al. "Construction of phi29 DNA-packaging RNA monomers, dimers, and trimers with variable sizes and shapes as potential parts for nanodevices." Journal of nanoscience and nanotechnology 3.4 (2003): 295-302.
Shu, Dan, et al. "Programmable folding of fusion RNA in vivo and in vitro driven by pRNA 3WJ motif of phi29 DNA packaging motor." Nucleic acids research 42.2 (2013): e10-e10.
Shu, Dan, et al. "Thermodynamically stable RNA three-way junction for constructing multifunctional nanoparticles for delivery of therapeutics." Nature nanotechnology 6.10 (2011): 658-667.
Shu, Yi, et al. "Fabrication of 14 different RNA nanoparticles for specific tumor targeting without accumulation in normal organs." Rna 19.6 (2013): 767-777.

(Continued)

*Primary Examiner* — Kimberly Chong
(74) *Attorney, Agent, or Firm* — Baker Donelson

(57) ABSTRACT

The present invention is directed towards an artificial RNA nanostructure comprising multiple external strands of RNA, each external strand comprising about 40-50 nucleotides; one internal strand of RNA comprising more than about 50 nucleotides; the internal strands and external strands assembled to form a triangle nanostructure, a square nanostructure, or a polygon nanostructure and a pRNA three-way junction (3WJ) motif at each vertex of the nanostructure. Such nanostructure can be provided in a composition together with an adjuvant for use in inducing the production of high affinity neutralizing antibodies or inhibitory antibodies, inducing the production of cytokines, inducing an immune response in a subject, or a combination thereof.

16 Claims, 46 Drawing Sheets
Specification includes a Sequence Listing.

(56) References Cited

OTHER PUBLICATIONS

Shu, Yi, et al. "Fabrication of pRNA nanoparticles to deliver therapeutic RNAs and bioactive compounds into tumor cells." Nature protocols 8.9 (2013): 1635-1659.
Walter, Frank, et al. "Global structure of four-way RNA junctions studied using fluorescence resonance energy transfer." RNA 4.6 (1998): 719-728.
Winter, Patrick M., et al. "Molecular imaging of angiogenesis in early-stage atherosclerosis with a v β 3-integrin—targeted nanoparticles." Circulation 108.18 (2003): 2270-2274.
Zhang, Hui, et al. "Crystal structure of 3WJ core revealing divalent ion-promoted thermostability and assembly of the Phi29 hexameric motor pRNA." Rna 19.9 (2013): 1226-1237.
Abdelmawla, Sherine, et al. "Pharmacological characterization of chemically synthesized monomeric phi29 pRNA nanoparticles for systemic delivery." Molecular Therapy 19.7 (2011): 1312-1322.
Afonin, Kirill A., Dennis J. Cieply, and Neocles B. Leontis. "Specific RNA self-assembly with minimal paranemic motifs." Journal of the American Chemical Society 130.1 (2008): 93-102.
Afonin, Kirill A., et al. "In vitro assembly of cubic RNA-based scaffolds designed in silico." Nature nanotechnology 5.9 (2010): 676-682.
Batey, Robert T., Robert P. Rambo, and Jennifer A. Doudna. "Tertiary motifs in RNA structure and folding." Angewandte Chemie International Edition 38.16 (1999): 2326-2343.
Bindewald, Eckart, et al. "RNAJunction: a database of RNA junctions and kissing loops for three-dimensional structural analysis and nanodesign." Nucleic acids research 36.suppl_1 (2007): D392-D397.
Binzel, Daniel W., Emil F. Khisamutdinov, and Peixuan Guo. "Entropy-driven one-step formation of Phi29 pRNA 3WJ from three RNA fragments." Biochemistry 53.14 (2014): 2221-2231.
Borsi, Laura, et al. "Expression of different tenascin isoforms in normal, hyperplastic and neoplastic human breast issues." International journal of cancer 52.5 (1992): 688-692.
Cayrol, Bastien, et al. "A nanostructure made of a bacterial noncoding RNA." Journal of the American Chemical Society 131.47 (2009): 17270-17276.
Chadalavada, Durga M., and Philip C. Bevilacqua. "Analyzing RNA and DNA folding using temperature gradient gel electrophoresis (TGGE) with application to in vitro selections." Methods in enzymology 468 (2009): 389-408.
Chen, Chaoping, et al. "A Dimer as a Building Block in Assembling RNA a Hexamer That Gears Bacterial Virus phi29 DNA-Translocating Machinery." Journal of Biological Chemistry 275.23 (2000): 17510-17516.
Chen, Chaoping, et al. "Sequence requirement for hand-in-hand interaction in formation of RNA dimers and hexamers to gear f29 DNA translocation motor." Rna 5.6 (1999): 805-818.
Chworos, Arkadiusz, et al. "Building programmable jigsaw puzzles with RNA." Science 306.5704 (2004): 2068-2072.
Collins, Tony J. "ImageJ for microscopy." Biotechniques 43.1 Suppl (2007): 25-30.
Dibrov, Sergey M., et al. "Self-assembling RNA square." Proceedings of the National Academy of Sciences 108.16 (2011): 6405-6408.
Garver, Kyle, and Peixuan Guo. "Mapping the inter-RNA interaction of bacterial virus phi29 packaging RNA by site-specific photoaffinity cross-linking." Journal of Biological Chemistry 275.4 (2000): 2817-2824.
Geary, Cody, Arkadiusz Chworos, and Luc Jaeger. "Promoting RNA helical stacking via A-minor junctions." Nucleic acids research 39.3 (2010): 1066-1080.
Grabow, Wade W., et al. "Self-assembling RNA nanorings based on RNAI/II inverse kissing complexes." Nano letters 11.2 (2011): 878-887.
Guo, Peixuan, et al. "Inter-RNA interaction of phage f29 pRNA to form a hexameric complex for viral DNA transportation." Molecular cell 2.1 (1998): 149-155.

Guo, Peixuan. "Rolling circle transcription of tandem siRNA to generate spherulitic RNA nanoparticles for cell entry." Molecular Therapy—Nucleic Acids 1.8 (2012): e36.
Guo, Peixuan. "The emerging field of RNA nanotechnology." Nature nanotechnology 5.12 (2010): 833-842.
Guo, Song, Faqing Huang, and P. Guo. "Construction of folate-conjugated pRNA of bacteriophage phi29 DNA packaging motor for delivery of chimeric siRNA to nasopharyngeal carcinoma cells." Gene therapy 13.10 (2006): 814-820.
Guo, Songchuan, et al. "Specific delivery of therapeutic RNAs to cancer cells via the dimerization mechanism of phi29 motor pRNA." Human gene therapy 16.9 (2005): 1097-1110.
Haque, Farzin, et al. "Ultrastable synergistic tetravalent RNA nanoparticles for targeting to cancers." Nano today 7.4 (2012): 245-257.
Hemmi, Hiroaki, et al. "A Toll-like receptor recognizes bacterial DNA." Nature 408.6813 (2000): 740-745.
Ishikawa, Junya, et al. "GNRA/receptor interacting modules: versatile modular units for natural and artificial RNA architectures." Methods 54.2 (2011): 226-238.
Jaeger, Luc, Eric Westhof, and Neocles B. Leontis. "TectoRNA: modular assembly units for the construction of RNA nano-objects." Nucleic acids research 29.2 (2001): 455-463.
Khaled, Annette, et al. "Controllable self-assembly of nanoparticles for specific delivery of multiple therapeutic molecules to cancer cells using RNA nanotechnology." Nano letters 5.9 (2005): 1797-1808.
Khisamutdinov, Emil F., et al. "Enhancing immunomodulation on innate immunity by shape transition among RNA triangle, square and pentagon nanovehicles." Nucleic acids research 42.15 (2014): 9996-10004.
Krieg, Arthur M. "CpG motifs: the active ingredient in bacterial extracts?." Nature medicine 9.7 (2003): 831-835.
Latz, Eicke, et al. "TLR9 signals after translocating from the ER to CpG DNA in the lysosome." Nature immunology 5.2 (2004): 190-198.
Lee, Fook-Thean, et al. "Specific Localization, Gamma Camera Imaging, and Intracellular Trafficking of Radiolabelled Chimeric Anti-GD3 Ganglioside Monoclonal Antibody KM871 in SK-MEL-28 Melanoma Xenografts." Cancer research 61.11 (2001): 4474-4482.
Lee, Jong Bum, et al. "Self-assembled RNA interference microsponges for efficient siRNA delivery." Nature materials 11.4 (2012): 316-322.
Leontis, Neocles B., and Eric Westhof. "Analysis of RNA motifs." Current opinion in structural biology 13.3 (2003): 300-308.
Leontis, Neocles B., and Eric Westhof. "The annotation of RNA motifs." Comparative and functional genomics 3.6 (2002): 518-524.
Lescoute, Aurélie, and Eric Westhof. "Topology of three-way junctions in folded RNAs." Rna 12.1 (2006): 83-93.
Li, Jiang, et al. "Self-assembled multivalent DNA nanostructures for noninvasive intracellular delivery of immunostimulatory CpG oligonucleotides." ACS nano 5.11 (2011): 8783-8789.
Lilley, David MJ. "Structures of helical junctions in nucleic acids." Quarterly reviews of biophysics 33.2 (2000): 109-159.
Liu, Jing, et al. "Fabrication of stable and RNase-resistant RNA nanoparticles active in gearing the nanomotors for viral DNA packaging." ACS nano 5.1 (2010): 237-246.
Lyubchenko, Yuri L., and Luda S. Shlyakhtenko. "AFM for analysis of structure and dynamics of DNA and protein-DNA complexes." Methods 47.3 (2009): 206-213.
Lyubchenko, Yuri L., et al. "Atomic force microscopy imaging of double stranded DNA and RNA." Journal of biomolecular structure and dynamics 10.3 (1992): 589-606.
Matsuoka, Nao, et al. "Structural and immunostimulatory properties of Y-shaped DNA consisting of phosphodiester and phosphorothioate oligodeoxynucleotides." Journal of Controlled Release 148.3 (2010): 311-316.
Medzhitov, Ruslan. "CpG DNA: security code for host defense." Nature immunology 2.1 (2001): 15-17.

(56) References Cited

OTHER PUBLICATIONS

Mo, Ji-Hun, et al. "Suppression of allergic response by CpG motif oligodeoxynucleotide—house-dust mite conjugate in animal model of allergic rhinitis." American journal of rhinology20.2 (2006): 212-218.

Mohri, Kohta, et al. "Design and development of nanosized DNA assemblies in polypod-like structures as efficient vehicles for immunostimulatory CpG motifs to immune cells." ACS nano 6.7 (2012): 5931-5940.

Mohri, Kohta, et al. "Increased immunostimulatory activity of polypod-like structured DNA by ligation of the terminal loop structures." Journal of controlled release 163.3 (2012): 285-292.

Murphy, Mark K., et al. "Evaluation of the new cesium-131 seed for use in low-energy x-ray brachytherapy." Medical physics 31.6 (2004): 1529-1538.

Narunsky, Lian, et al. "Imaging aspects of the tumor stroma with therapeutic implications." Pharmacology & therapeutics141.2 (2014): 192-208.

Nasalean, Lorena, et al. "Controlling RNA self-assembly to form filaments." Nucleic acids research 34.5 (2006): 1381-1392.

Noël, Agnes, Maud Jost, and Erik Maquoi. "Matrix metalloproteinases at cancer tumor—host interface." Seminars in cell & developmental biology. vol. 19. No. 1. Academic Press, 2008.

Novikova, Irina V., et al. "Engineering cooperative tecto—RNA complexes having programmable stoichiometries." Nucleic acids research 39.7 (2010): 2903-2917.

Khisamutdinov, E. F., et al.; RNA as a Boiling-Resistant Anionic Polymer Material to Build Robust Structures With Defined Shape and Stoichiometry. ACS NANO, vol. 8, No. 5, pp. 411-4781; published online Apr. 3, 2014; abstract, figure 1A; p. 4771, second column, first paragraph, p. 4772, column.

Kobayahi, N. et al., Oligode oxynucleotides Expressing Polyguanosine Motifs Promote Anti-Tumor Activity through the Up-Regulation of IL-2. Journal of Immunolog. Feb. 15, 2013. vol. 190, No. 4: pp. 1882-1889, DOI:10.4049/immunol.1201063; abstract, figure 2C.

Qui, M. et al.; RNA Nanotechnology for Computer Design and in Vivo Computation. Phil Trans R Soc A 371: Sep. 2, 2013. DOI: 10.1098/rsta.2012.0310, pp. 1-24; figures 9, 10.

International Search Report dated Dec. 3, 2015.

Written Opinion dated Dec. 3, 2015.

* cited by examiner

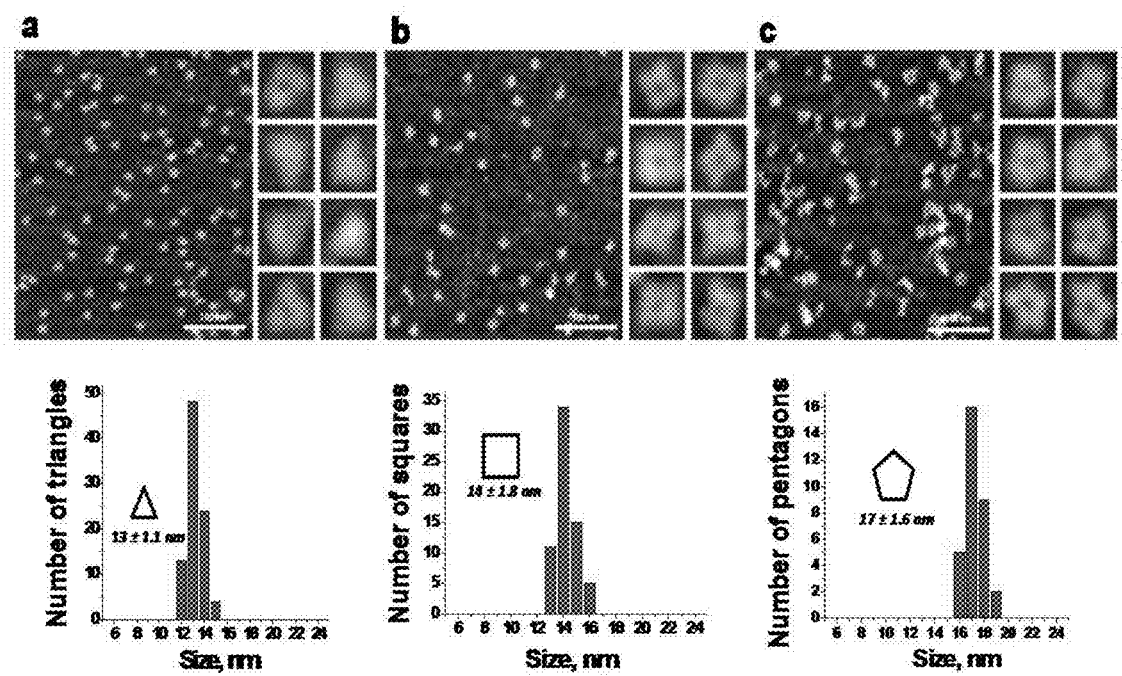
FIG. 9A-C

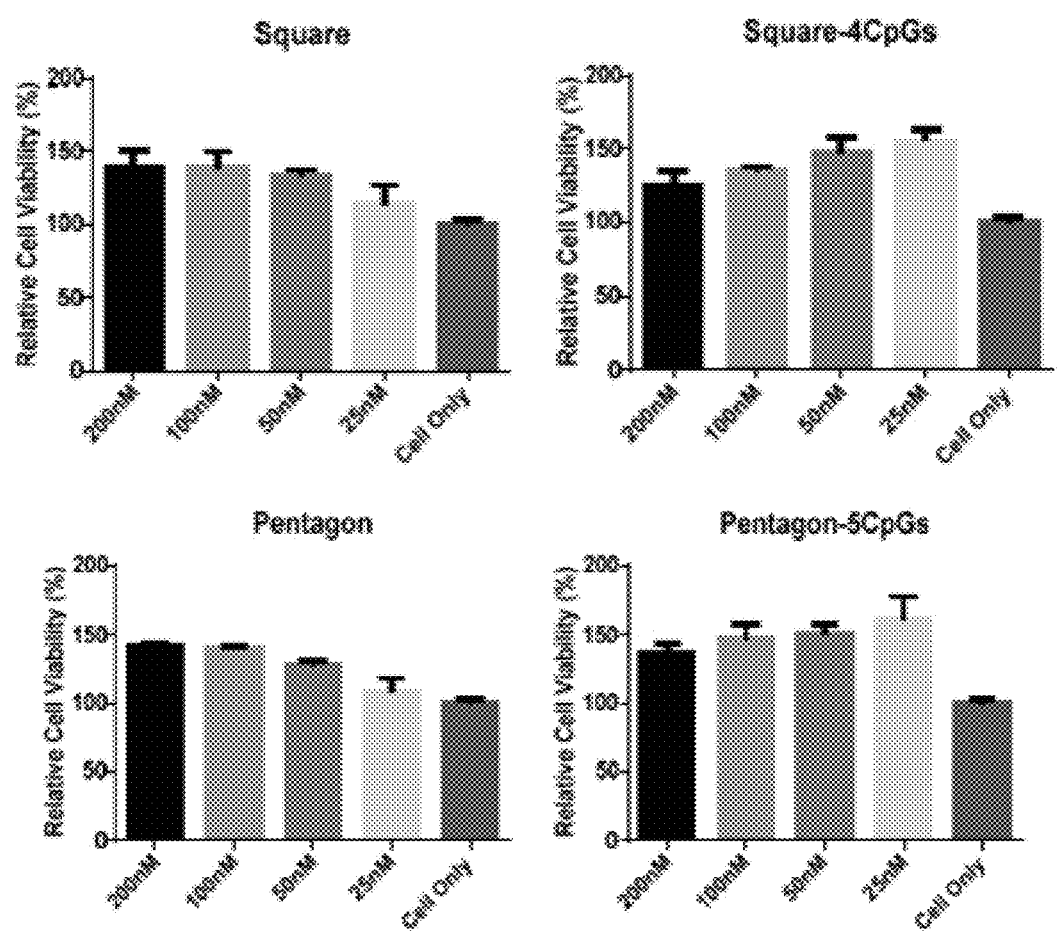
FIG. 13, Cont'd

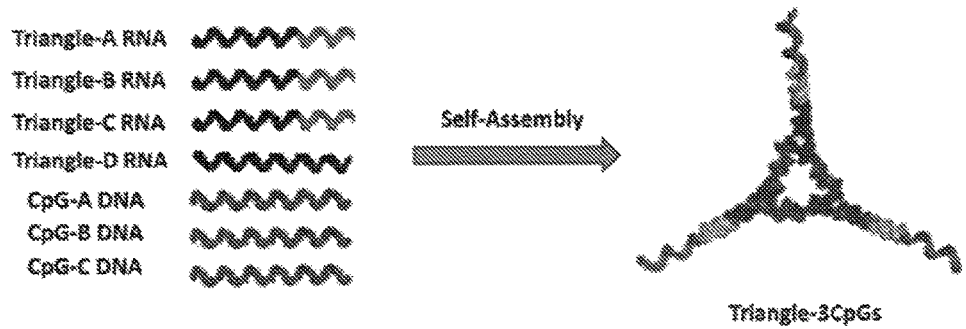

FIG. 16

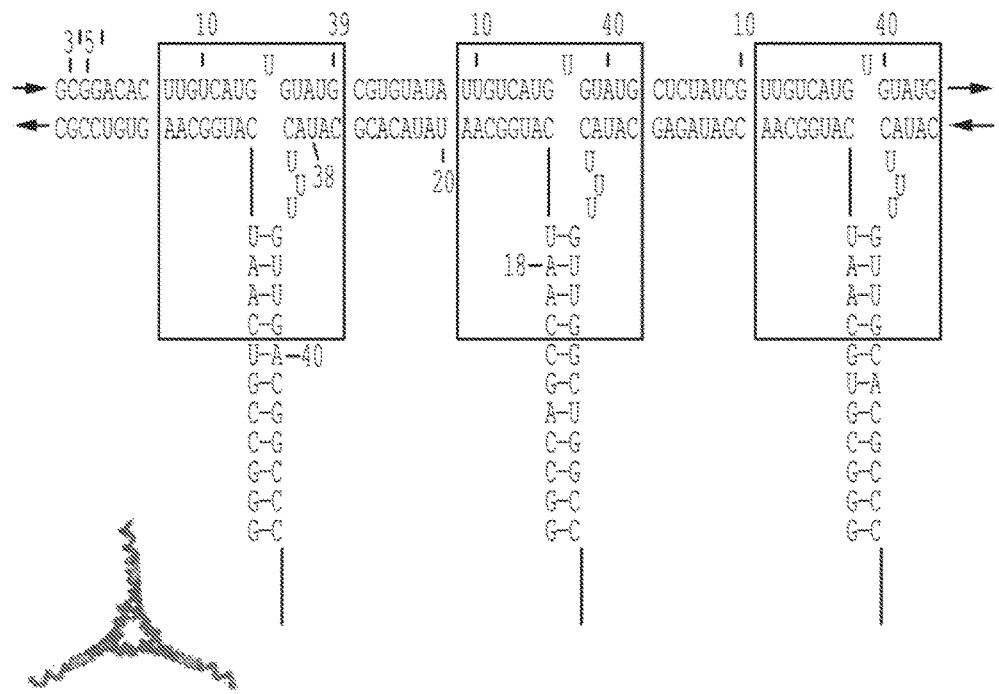

A21 5'-GGGCCGUCAAUCAUGGCAAGUGUCCGCCAUACUUUGUUGCACGCCC UCGGAAUGCA AUACGACUGU A-3'
B21 5'-GGGCGUGCAAUCAUGGCAACGAUAGAGCAUACUUUGUUGGCUGGCC UAGUUGGAAA UGGCGGUAUG G-3'
C21 5'-GGCCAGCCAAUCAUGGCAAUAUACACGCAUACUUUGUUGACGGCCC AGUUAAACAU CGCAUGUGCU U-3'

| CpG DNA with 21 nt overhang and 7T linker |
|---|
| 5'-TCC ATG ACG TTC CTG ACG TTT TTT T TAC AGT CGT ATT GCA TTC CGA -3'  SEQ ID NO: 17 |
| 5'-TCC ATG ACG TTC CTG ACG TTT TTT T CCA TAC CGC CAT TTC CAA CTA -3'  SEQ ID NO: 19 |
| 5'-TCC ATG ACG TTC CTG ACG TTT TTT T AAG CAC ATG CGA TGT TTA ACT -3'  SEQ ID NO: 21 |

FIG. 17

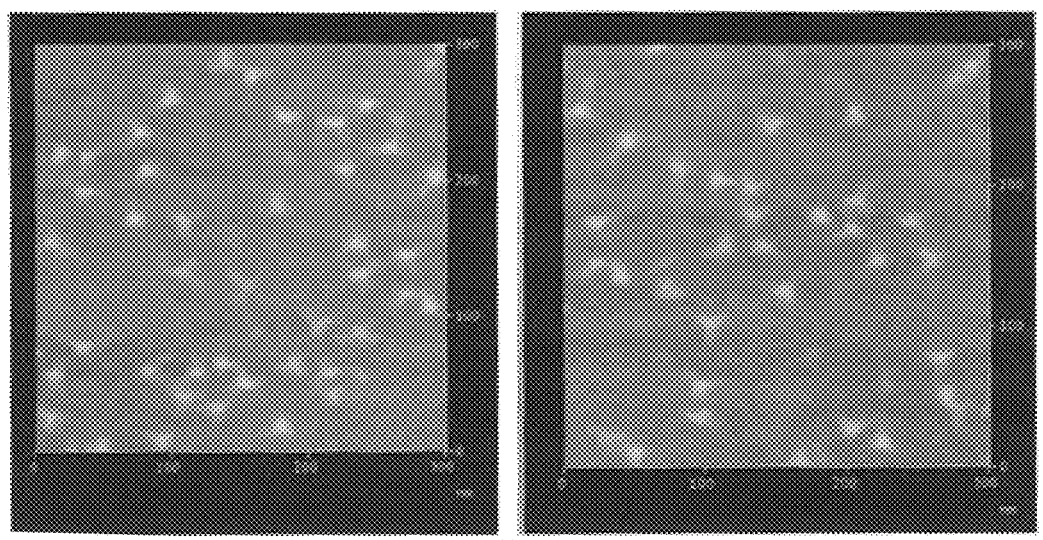
FIG. 30
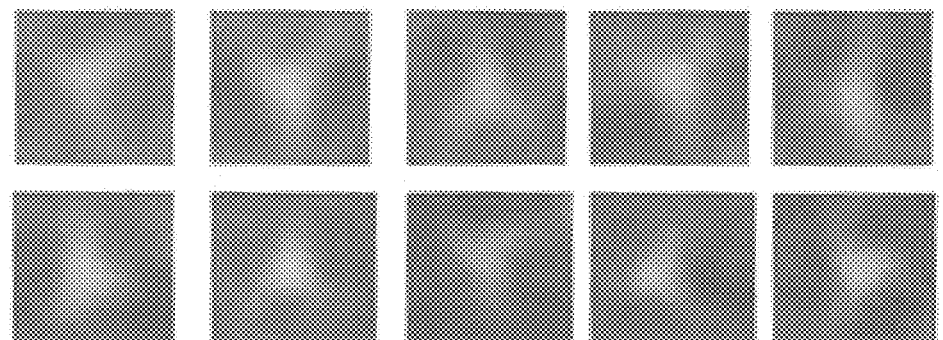
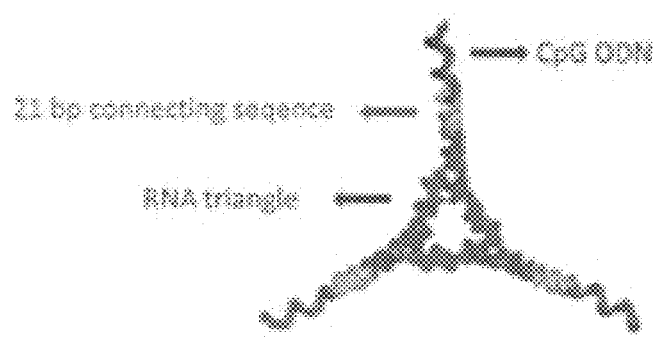
FIG. 31

| CpG | Positive Binding (%) | Triangle-1CpG | Positive Binding (%) | Triangle-2CpGs | Positive Binding (%) | Triangle-3CpGs | Positive Binding (%) |
|---|---|---|---|---|---|---|---|
| 300nM | 20.3 | 300nM | 98.8 | 300nM | 98.4 | 300nM | 97.2 |
| 150nM | 7.19 | 150nM | 93.6 | 150nM | 82.7 | 150nM | 90.8 |
| 75nM | 4.77 | 75nM | 57.3 | 75nM | 68.4 | 75nM | 53.3 |
| 37.5nM | 2.39 | 37.5nM | 26.4 | 37.5nM | 31.7 | 37.5nM | 26.6 |

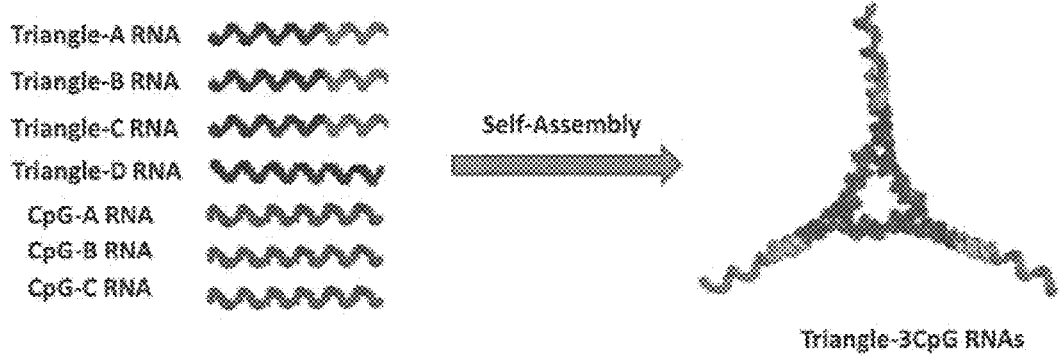

CpG RNA with 21nt overhang and 5U linker (CpG motif underlined)
5'-UCCAUGACG UUCCUGACGU UUUUUUACA GUCGUAUUGC AUUCCGA-3' SEQ ID NO: 16
5'-UCCAUGACGU UCCUGACGUU UUUUUCCAUA CCGCCAUUUC CAACUA-3' SEQ ID NO: 18
5'-UCCAUGACGU UCCUGACGUU UUUUAAGCA CAUGCGAUGU UUAACU-3' SEQ ID NO: 20

FIG. 56

A21 CpG RNA

- 5'-UCCAUGACG UUCCUGACGU UUUUUUACA GUCGUAUUGC AUUCCGA-3' 46 SEQ ID NO: 16
- DNA : TAA TAC GAC TCA CTATA TCC ATG ACG TTC CTG ACG TTT TTT T TAC AGT CGT ATT GCA TTC CGA 63nt SEQ ID NO: 25
- 5' Primer: TAA TAC GAC TCA CTATA TCC ATG ACG TTC CTG ACG TTT SEQ ID NO: 26
- 3' Primer: TCGGAATGCA ATACGACTGT AAAAAAACG TCAGGAA SEQ ID NO: 27

FIG. 57

B21 CpG RNA

- 5'-UCCAUGACGU UCCUGACGUU UUUUUCCAUA CCGCCAUUUC CAACUA-3' 46n  SEQ ID NO: 18
- DNA: TAA TAC GAC TCA CTATA TCC ATG ACG TTC CTG ACG TTT TTT T CCA TAC CGC CAT TTC AAC CTA 63nt  SEQ ID NO: 28
- 5' Primer: TAA TAC GAC TCA CTATA TCC ATG ACG TTC CTG ACG TTT  SEQ ID NO: 29
- 3' Primer: TAGTTGGAAA TGGCGGTATG GAAAAAACG TCAGGAA  SEQ ID NO: 30

FIG. 58

C21 CpG RNA

- 5'-UCCAUGACGU UCCUGACGUU UUUUUAAGCA CAUGCGAUGU UUAACU-3' 46n  SEQ ID NO: 20
- DNA: TAA TAC GAC TCA CTATA TCC ATG ACG TTC CTG ACG TTT TTT T AAG CAC ATG CGA TGT TTA ACT 63nt  SEQ ID NO: 31
- 5' Primer: TAA TAC GAC TCA CTATA TCC ATG ACG TTC CTG ACG TTT  SEQ ID NO: 32
- 3' Primer: AGTTAAACAT CGCATGTGCT TAAAAAACG TCAGGAA  SEQ ID NO: 33

FIG. 59

1. DNA for A21 CpG RNA (63nt)
2. DNA for B21 CpG RNA (63nt)
3. DNA for C21 CpG RNA (63nt)
4. ULR ladder CpG RNA with 21nt overhang and 5U linker (CpG motif underlined)
5'-UCCAUGACG UUCCUGACGU UUUUUUUACA GUCGUAUUGC AUUCCGA-3'  SEQ ID NO: 16
5'-UCCAUGACGU UCCUGACGUU UUUUUCCAUA CCGCCAUUUC CAACUA-3'  SEQ ID NO: 18
5'-UCCAUGACGU UCCUGACGUU UUUUUAAGCA CAUGCGAUGU UUAACU-3'  SEQ ID NO: 20

US 10,378,018 B2

RNA-BASED COMPOSITIONS AND ADJUVANTS FOR PROPHYLACTIC AND THERAPEUTIC TREATMENT

RELATED APPLICATIONS

This application is a continuation-in-part of PCT application No. PCT/US2015/036798, filed Jun. 19, 2015, which claims priority of U.S. Provisional Patent Application No. 62/014,503, filed Jun. 19, 2014, and the entire disclosures of which are hereby incorporated by reference in their entireties.

GOVERNMENT INTEREST

This invention was made with government support under EB003730, EB 012135, and CA 151648 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 23, 2017, is named 2935720-000002 SL.txt and is 25,100 bytes in size.

TECHNICAL FIELD

The presently-disclosed subject matter relates to RNA-based compositions, including immunostimulatory RNA-containing compositions and RNA nanoparticle-containing compositions, methods of making the compositions, and use of RNA-based adjuvants for prophylactic and therapeutic treatment.

INTRODUCTION

Cancer and infectious diseases such as influenza and human immunodeficiency virus infection/acquired immunodeficiency syndrome (HIV/AIDS) are still a huge threat to public health world-wide. Prophylactic and treatment vaccines could offer promising opportunities for controlling these diseases. However, despite tens of years of extensive research, such vaccines are still far away from completely controlling these diseases due to either low effectiveness or safety issues. New strategies and approaches in designing and developing new vaccines and adjuvants targeting these diseases are urgently needed.

SUMMARY

The presently-disclosed subject matter meets some or all of the needs as described herein, as will become evident to those of ordinary skill in the art after a study of information as described herein.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter comprises RNA that can be used as a construction material, immunostimulatory agent, or a combination thereof for the development of new nanovaccines and adjuvants for disease prevention and treatment.

The presently-disclosed subject matter comprises a composition which is comprised of an RNA-oligonucleotide, which can be single-stranded or double stranded, and an immunostimulatory motif.

In some embodiments, the RNA-oligonucleotide comprises a chemical modification. In some preferred embodiments, the chemical modification is selected from 2'Fluoro, 2'Amine, and 2'O-Methyl. In some embodiments, the RNA-oligonucleotide is about 8-50 bases in length. In some embodiments, the RNA-oligonucleotide is partially double stranded, for example containing a hair-pin.

In some embodiments, the immunostimulatory motif is immunostimulatory RNA or a CpG oligodeoxyribonucleotide. In some embodiments, the immunostimulatory motif is conjugated to the RNA-oligonucleotide. In some embodiments the immunostimulatory motif is oligodeoxyribonucleotide. In some embodiments, the composition is provided as an adjuvant.

The presently-disclosed subject matter comprises an artificial RNA nanostructure comprising multiple external strands and one internal strand, wherein the external strands and internal strand self-assemble to form a nanostructure. In some embodiments, the multiple external strands can, for example, be 3, 4, or 5 strands. In some embodiments, the external strands comprise about 48 nucleotides; and in some preferred embodiments, the nanostructure comprises a pRNA 3WJ motif at each vertex. In some embodiments, the external strands comprise more than 48 nucleotides. In some embodiments, the external strands comprise less than 48 nucleotides. In some embodiments, the external strands comprise about 10, about 20, about 30, about 40, about 50, about 60, about 70, about 80, about 90, about 100 nucleotides.

In some embodiments the artificial RNA nanostructure comprises a triangle and has a stretched intrahelical angle between about H1 and H2. In other embodiments, the nanostructure comprises a square and has a stretched intrahelical angle between about H1 and H2. In other embodiments, nanostructure comprises a pentagon and has a stretched intrahelical angle between about H1 and H2. In some embodiments, the RNA nanostructure comprises an RNA triangle, RNA square, RNA pentagon, RNA hexagon, RNA three-way junction, and RNA four-way junction. In some embodiments, the RNA nanostructure is derived from a 3WJ motif. In some embodiments, the RNA nanostructure comprises a stretched intrahelical angle between about H1 and H2, as exemplified in FIG. 1.

In some embodiments, the subject matter relates to a composition comprising an RNA nanostructure that comprises an adjuvant, an antigen, and/or a targeting ligand. In some embodiments, the composition induces an immune response. In some embodiments, the immune response increases cytokine at least ten fold as compared to the adjuvant, the antigen, and/or the targeting ligand provided independently of the RNA nanostructure. In some embodiments, the adjuvant comprises a composition comprising an RNA-oligonucleotide and an immunostimulatory motif. In some embodiments, the RNA-oligonucleotide and immunostimulatory motif are incorporated into the RNA nanoparticle by the RNA-oligonucleotide being covalently bonded to an RNA strand of the RNA nanoparticle. Non-limiting examples of the bond between RNA-oligonucleotide and the RNA strand of the RNA nanoparticle is ionic bond or hydrogen bond. In some embodiments, the RNA-oligonucleotide and immunostimulatory motif are incorporated into the RNA nanoparticle by base pairing between the RNA-oligonucleotide and the RNA nanoparticle. In some embodiments, the adjuvant comprises an immunostimulatory RNA (isRNA), and in some embodiments the adjuvant comprises a CpG oligodeoxyribonucleotide. In some embodiments, the adjuvant comprises isRNA that is about 8 to about 50 bases in length. In some embodiments, the adjuvant comprises isRNA that is less than 8 bases in length. In some embodiments, the adjuvant comprises isRNA that is more than 50 bases in length. In some embodiments, the adjuvant comprises isRNA that is about 1, about 2, about 3, about 4, about 5, about 6, about 7, about 8, about 9, about 10, about 20, about 30, about 40, about 50, about 60, about 70, about 80, about 90, about 100 bases in length. In some embodiments, the adjuvant is CpG RNA. In some embodiments, the adjuvant is covalently bonded to an RNA strand of the RNA nanoparticle. In other embodiments, the adjuvant is incorporated into the RNA nanoparticle by base pairing.

Embodiments as described herein comprise one or more of the sequences of SEQ ID NOS: 16-24. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% identity to a nucleic acid sequence comprising SEQ ID NOS: 16-24. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% similarity to a nucleic acid sequence comprising SEQ ID NOS: 16-24.

In some embodiments, the RNA nanostructure comprises an antigen. In some embodiments, the antigen is derived from a bacteria, virus, or cell. In some embodiments, the antigen binds to a neutralizing antibody or an inhibitory antibody. In some embodiments, the antigen comprises a neutralizing epitope. In some embodiments, the antigen comprises B-cell epitope, T-cell epitope, T-helper epitope, epitopes derived from PG120, gp41 epitopes, glycans, peptides, T-helper peptides, streptavidin, or a combination thereof.

In some embodiments, the RNA nanostructure comprises a targeting ligand. In some embodiments, the targeting ligand comprises an aptamer, a cell surface marker, folate, siRNA, shRNA, or a combination thereof. In some embodiments, the aptamer binds to an HIV epitope. In other embodiments, the cell surface marker comprises a macrophage or lymphocyte. In some embodiments, the targeting ligand targets B cells, T cells, dendritic cells, macrophages, cancer cells, or a combination thereof. In some embodiments, there are more than one targeting ligand. In some embodiments, the targeting ligands are the same. In other embodiments, the targeting ligands are not all the same.

Embodiments as described herein comprise a method of inducing an immune response in a subject, comprising administering to the subject an effective amount of the compositions of the present invention. In some embodiments, the method comprises administering an RNA-oligonucleotide and an immunostimulatory motif. In some embodiments, the method comprises administering a composition comprising an RNA nanostructure and an adjuvant, an antigen, and/or a targeting ligand.

Embodiments as described herein comprise a method of inducing the production of cytokines. In some embodiments, the cytokines comprise TNF-alpha, IL-6, IL-12, or a combination thereof. In some embodiments, the method comprises administering an RNA-oligonucleotide and an immunostimulatory motif. In some embodiments, the production of cytokines is increased at least ten fold as compared to the immunostimulatory motif provided independently of the RNA-oligonucleotide.

In some embodiments, the method comprises administering a composition comprising an RNA nanostructure and an adjuvant, an antigen, a targeting ligand, or a combination of the adjuvant, ligand, or targeting ligand. In some embodiments, the induction of the production of cytokines is increased at least ten fold as compared to the adjuvant, the antigen, and/or the targeting ligand provided independently of the RNA nanostructure.

In some embodiments, administering a composition as described herein to a subject induces the production of high affinity neutralizing antibodies or inhibitory antibodies. In some embodiments, the subject has or is at risk of having a pathological condition. In some embodiments, the pathological condition comprises cancer, human immunodeficiency virus (HIV), influenza, drug and substance abuse, or a combination thereof.

In some embodiments, embodiments as described herein are used for the manufacture of a medicament useful for the treatment of a pathological condition in a subject. In some embodiments, the medicament is used prophylactically.

Embodiments as described herein also provide methods of making an RNA nanostructure. In some embodiments, the method of making an RNA nanostructure comprises mixing equimolar concentrations of a multiple of external RNA strands, and one internal RNA strand to make a mixture, annealing the mixture, and cooling the mixture slowly. In some embodiments, the mixture is cooled at about 1° C. per minute. In some embodiments, the mixtures is cooled faster or slower than about 1° C. per minute. In some embodiments, the mixture is cooled from about 80° C. to about 4° C. In some embodiments, the mixture is cooled to a temperature greater than 80° C. In some embodiments, the mixture is cooled to a temperature less than 80° C. In some embodiments, the mixture is cooled to about 1° C., about 2° C., about 3° C., about 4° C., about 5° C., about 6° C., about 7° C., about 8° C., about 9° C., about 10° C., about 20° C., about 30° C., about 40° C., about 50° C., about 60° C., or about 70° C. In some embodiments, the mixture is annealed for about one hour. In some embodiments, the mixture is annealed for more than one hour. In some embodiments, the mixture is annealed for less than one hour. In some embodiments, the mixture is annealed for up to about 10, about 20, about 30, about 40, or about 50 minutes. In some embodiments, the mixture is annealed for up to about 1, about 2, about 3, about 4, about 5, about 6, about 10, about 12, about 18, or about 24 hours. In some embodiments, the method comprises modifying one or more of the external strands to comprise at least one antigen, at least one adjuvant, at least one targeting ligand, or a combination thereof. In some embodiments, there are optionally 3, 4, or 5 external strands. In some embodiments, the external strands comprise about 48 nucleotides. In some embodiments, the external strands comprise more than 48 nucleotides. In some embodiments, the external strands comprise less than 48 nucleotides. In some embodiments, the external strands comprise about 10, about 20, about 30, about 40, about 50, about 60, about 70, about 80, about 90, about 100 nucleotides. In some embodiments, the nanostructure produces by the method comprises a pRNA 3WJ motif at each vertex. In some methods, the nanostructure shape comprises a triangle, square and pentagon. In some embodiments, the shapes produced by the method have a stretched intrahelical angle between about H1 and about H2.

Embodiments as described herein comprise an RNA-oligonucleotide and an immunostimulatory motif. In embodiments, the RNA oligonucleotide can be single-stranded, double stranded, or partially double stranded. In embodiments, the RNA-oligonucleotide comprises a chemical modification, examples of which comprise 2'Fluoro, 2'Amine, and 2'O-Methyl. In embodiments, the RNA oligonucleotide comprises about 8 to about 50 bases in length.

Embodiments as described herein comprise an immunostimulatory motif. In embodiments, the immunostimulatory motif comprises an immunostimulatory RNA (isRNA), and a CpG oligodeoxyribonucleotide. In embodiments, the immunostimulatory motif can be conjugated to the RNA-oligonucleotide. For example, the immunostimulatory motif is CpG oligodeoxyribonucleotide conjugated to the RNA-oligonucleotide. For example, the isRNA is CpG RNA conjugated to the RNA-oligonucleotide. Embodiments as described herein can be provided as an adjuvant.

Embodiments as described herein comprise the oligonucleotide sequence of A21 CpG RNA (SEQ ID NO: 16), B21 CpG RNA (SEQ ID NO: 18), and C21 CpG RNA (SEQ ID NO: 20). Embodiments as described herein comprise one or more of the sequences of SEQ ID NOs 16-21. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% identity to a nucleic acid sequence comprising SEQ ID Nos 16-21. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% similarity to a nucleic acid sequence comprising SEQ ID Nos 16-21.

Embodiments as described herein comprise an artificial RNA nanostructure comprising three, four, or five external strands of RNA. In embodiments, each external strand comprises about 40 to about 50 nucleotides; one internal strand of RNA, including more than about 50 nucleotides, the internal strands and external strands assembled to form a triangle nanostructure, a square nanostructure, or a polygon nanostructure; and a pRNA three-way junction (3WJ) motif at each vertex of the nanostructure.

In embodiments, the nanostructure comprises a triangle. In embodiments, the triangle has a stretched intrahelical angle between about H1 and about H2. In embodiments, the angle comprises about 60°. In embodiments, the angle comprises greater than 60°. In other embodiments, the angle comprises less than 60°.

In embodiments, the nanostructure comprises a square. In embodiments, the square has a stretched intrahelical angle between about H1 and about H2. In some embodiments, the angle comprises about 90°. In embodiments, the angle comprises greater than 90°. In other embodiments, the angle comprises less than 90°.

In embodiments, the nanostructure comprises a pentagon. In embodiments, the pentagon has a stretched intrahelical angle between about H1 and about H2. In some embodiments, the angle comprises about 100°. In embodiments, the angle comprises greater than 108°. In other embodiments, the angle comprises less than 108°.

Embodiments as described herein comprise one or more of the sequences of SEQ ID NOs 1-4. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% identity to a nucleic acid sequence comprising SEQ ID Nos 1-4. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% similarity to a nucleic acid sequence comprising SEQ ID Nos 1-4.

Embodiments as described herein comprise one or more of the sequences of SEQ ID NOs 5-9. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% identity to a nucleic acid sequence comprising SEQ ID Nos 5-9. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% similarity to a nucleic acid sequence comprising SEQ ID Nos 5-9.

Embodiments as described herein comprise one or more of the sequences of SEQ ID NOs 10-15. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% identity to a nucleic acid sequence comprising SEQ ID Nos 10-15. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% similarity to a nucleic acid sequence comprising SEQ ID Nos 10-15.

Embodiments as described herein comprise one or more immunostimulatory motifs as described herein. For example, such motifs comprise one or more immunostimulatory RNAs (isRNA) or CpG motifs.

Embodiments as described herein comprise an RNA nanostructure as described herein, an adjuvant, an antigen, a targeting ligand, or a combination thereof. In embodiments, the RNA nanostructure comprises an RNA triangle, RNA square, RNA pentagon, RNA hexagon, RNA three-way junction, RNA four-way junction, or any combination thereof. Embodiments as described herein can be derived from a 3JW motif. In embodiments, the RNA nanostructure contains a stretched intrahelical angle between H1 and H2, as described herein.

In embodiments, the adjuvant comprises an immunostimulatory RNA (isRNA) and a CpG oligodeoxyribonucleotide (CpG). In embodiments, the isRNA comprises an oligonucleotide comprising about 8 to about 50 bases in length.

In embodiments, the isRNA is incorporated into the RNA nanoparticle by being covalently bonded to an RNA strand of the RNA nanoparticle. In embodiments, the CpG RNA comprises CpG RNA. In embodiments, the CpG RNA comprises A21 CpG RNA (SEQ ID NO: 16), B21 CpG RNA (SEQ ID NO: 18), and C21 CpG RNA (SEQ ID NO: 20), as described herein.

In embodiments, the isRNA is incorporated into the RNA nanoparticle by base pairing. In embodiments, the isRNA comprises a CpG RNA. In embodiments, the CpG RNA comprises A21 CpG RNA (SEQ ID NO: 16), B21 CpG RNA (SEQ ID NO: 18), and C21 CpG RNA (SEQ ID NO: 20), as described herein.

In embodiments, an adjuvant refers to a composition as described herein given in combination with an RNA nanostructure to enhance its immunogenicity.

In embodiments, the RNA-oligonucleotide and immunostimulatory motif are incorporated into the RNA nanoparticle by base pairing between the RNA-oligonucleotide and the RNA nanoparticle.

In embodiments, the RNA-oligonucleotide and immunostimulatory motif are incorporated into the RNA nanoparticle by the RNA-oligonucleotide being covalently bonded to an RNA strand of the RNA nanoparticle.

In embodiments, the antigen comprises at least one antigen derived from a bacteria, virus, cell, a combination thereof, or a portion thereof.

In embodiments, the antigen comprises at least one antigen that binds to a neutralizing antibody, an inhibitory antibody, a combination thereof, or a portion thereof.

In embodiments, the antigen comprises at least one neutralizing epitope.

In embodiments, the antigen comprises B-cell epitope, T-cell epitope, T-helper epitope, epitopes derived from PG120, gp41 epitopes, glycans, peptides, T-helper peptides, streptavidin, or a combination thereof.

In embodiments, the targeting ligand comprises an aptamer, a cell surface marker, folate, siRNA, shRNA, or a combination thereof. In embodiments, the aptamer binds to an HIV epitope. In embodiments, the cell surface marker is a macrophage or a lymphocyte. In embodiments, the targeting ligand targets B cells, T cells, dendritic cells, macrophages, and/or cancer cells.

Embodiments as described herein comprise one or more targeting ligands. Embodiments as described herein comprise at least two targeting ligands. In embodiments, the targeting ligands are the same. In other embodiments, the targeting ligands are not all the same. In other embodiments, the targeting ligands are different.

Embodiments as described herein induce an immune response in a subject. In embodiments, the immune response increases cytokines at least about one fold, about two fold, about three fold, about four fold, about five fold, about six fold, about seven fold, about eight fold, about nine fold, about ten fold, about fifteen fold, about twenty fold, about thirty fold, about forty fold, about fifty fold as compared to the adjuvant, the antigen, and/or the targeting ligand provided independently of the RNA nanostructure.

Embodiments as described herein comprise a method of inducing an immune response in a subject comprising administering to the subject an effective amount of an embodiment as described herein.

Embodiments as described herein comprise a method of inducing the production of cytokines comprising administering to a subject an effective amount of an embodiment as described herein. In embodiments, the inducing the production of cytokines is increased at least about one fold, about two fold, about three fold, about four fold, about five fold, about six fold, about seven fold, about eight fold, about nine fold, about ten fold, about fifteen fold, about twenty fold, about thirty fold, about forty fold, about fifty fold as compared to the immunostimulatory motif provided independently of the RNA-oligonucleotide.

In embodiments, the subject has or is at risk of having a pathological condition. In embodiments, the subject has been diagnosed with a pathological condition. In embodiments, the pathological condition comprises cancer, human immunodeficiency virus (HIV), influenza, drug and substance abuse, or a combination thereof.

Embodiments as described herein comprise a method of inducing the production of cytokines. In embodiments, the method comprises administering to the subject an effective amount of an embodiment as described herein. In embodiments, the inducing the production of cytokines is increased at least about one fold, about two fold, about three fold, about four fold, about five fold, about six fold, about seven fold, about eight fold, about nine fold, about ten fold, about fifteen fold, about twenty fold, about thirty fold, about forty fold, about fifty fold as compared to the adjuvant, the antigen, and/or the targeting ligand provided independently of the RNA nanostructure. In embodiments, the cytokines comprise TNF-alpha, IL-6, IL-12, or a combination thereof.

In embodiments, the subject has or is at risk of having a pathological condition. In embodiments, the subject has been diagnosed with a pathological condition. In embodiments, the pathological condition comprises cancer, human immunodeficiency virus (HIV), influenza, drug and substance abuse, or a combination thereof.

Embodiments as described herein comprise a method of inducing the production of high affinity neutralizing antibodies or inhibitory antibodies. In embodiments, the method comprises administering embodiments as described herein to a subject having a pathological condition. In embodiments, the pathological condition comprises cancer, human immunodeficiency virus (HIV), influenza, drug and substance abuse, or a combination thereof.

Embodiments as described herein comprise the use of embodiments as described herein for the manufacture of a medicament useful for the treatment of a pathological condition in a subject. In embodiments, the pathological condition comprises cancer, human immunodeficiency virus (HIV), influenza, drug and substance abuse, or a combination thereof.

Embodiments as described herein comprise a composition as described herein for use in the prophylactic or therapeutic treatment of a pathological condition. In embodiments, the pathological condition comprises cancer, human immunodeficiency virus (HIV), influenza, drug and substance abuse, or a combination thereof.

Embodiments as described herein comprise a method of making an RNA nanostructure. In embodiments, the method comprises mixing a multiple of external RNA strands, and one internal RNA strand to make a mixture; annealing the mixture for one hour in a thermocycler; cooling the mixture at about 1° C. per minute from about 80° C. to about 4° C. In embodiments, equimolar concentrations of a multiple of external RNA strands, and one internal RNA strand can be mixed. In embodiments, the mixture can be annealed for 1, 5, 10, 20, 30, 40, 50, 60, 70, 80, 90 minutes. In embodiments, the mixture can be cooled to 1, 2, 3, 4, 5, 6, 7, 8, 9, 10, 20, 30, 40, 50, 60, 70° C. In embodiments, the mixture can be cooled at about 1, about 2, about 3, about 4, about 5, about 6, about 7, about 8, about 9, about 10° C. per minute. In embodiments, the method can further comprise modifying one or more of the external strands to contain an antigen, adjuvant, targeting ligand, or combination thereof. In embodiments, the external strands comprise 1, 2, 3, 4, 5, 6, 7, 8, 9, 10 strands. In embodiments, the external strands comprise 10, 20, 30, 40, 41, 42, 43, 44, 45, 46, 47, 48, 49, 50, 51, 52, 53, 54, 55, 56, 57, 58, 59, 60 nucleotides. In embodiments, the nanostructure comprises a pRNA 3WJ motif at each vertex. In embodiments, the nanostructure has a shape comprising a triangle, square and pentagon. In embodiments, the shape comprises a stretched intrahelical angle between H1 and H2.

Embodiments as described herein can comprise one or more of SEQ ID. NO 1, SEQ ID. NO 2, SEQ ID. NO 3, SEQ ID. NO 4, SEQ ID. NO 5, SEQ ID. NO 6, SEQ ID. NO 7, SEQ ID. NO 8, SEQ ID. NO 9, SEQ ID. NO 10, SEQ ID. NO 11, SEQ ID. NO 12, SEQ ID. NO 13, SEQ ID. NO 14, SEQ ID. NO 15, SEQ ID. NO 16, SEQ ID. NO 17, SEQ ID. NO 18, SEQ ID. NO 19, SEQ ID. NO 20, SEQ ID. NO 21, SEQ ID. NO 22, SEQ ID. NO 23, SEQ ID. NO 24, SEQ ID. NO 25, SEQ ID. NO 26, SEQ ID. NO 27, SEQ ID. NO 28, SEQ ID. NO 29, SEQ ID. NO 30, SEQ ID. NO 31, SEQ ID. NO 32, SEQ ID. NO 33, or any combination thereof. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% identity to a nucleic acid sequence comprising SEQ ID Nos 1-33. In one embodiment, the oligonucleotide has at least 60%, at least 65%, at least 70%, at least 80%, at least 85%, at least 90%, at least 91%, at least 92%, at least 93%, at least 94%, at least 95%, at least 96%, at least 97%, at least 98%, at least 99%, or 100% similarity to a nucleic acid sequence comprising SEQ ID Nos 1-33.

BRIEF DESCRIPTION OF THE DRAWINGS

The new features of embodiments as described herein are set forth with particularity in the appended claims. The drawings were originally published in color, incorporated by reference in their entireties (Emil F. Khisamutdinov, et. al., Enhancing immunomodulation on innate immunity by shape transition among RNA triangle, square and pentagon nanovehicles, *Nucleic Acids Res.* 2014 Sep. 2; 42(15): 9996-10004.). The black and white drawing of the instant application correspond to the color ones published. A better understanding of the features and advantages of the present invention will be obtained by reference to the following detailed description that sets forth illustrative embodiments, in which the principles of the invention are used, and the accompanying drawings of which:

FIG. 2 (C) Assembly properties of polygons evaluated on 7% native PAGEs. Asterisks '*' indicate the Cy5 labeled strands utilized on each type of polygon assembly.

FIG. 8A discloses regions $A_{TRI}$-$D_{TRI}$ as SEQ ID NOS 37-40, respectively. FIG. 8B discloses regions $A_{SQR}$-$E_{SQR}$ as SEQ ID NOS 41-45, respectively. FIG. 8C discloses regions $A_{PENT}$-$F_{PENT}$ as SEQ ID NOS 46-51, respectively.

FIG. 9A-9C shows RNA polygons population on mica surface AFM images of RNA polygons and population distribution of RNA triangle (a), square (b), and pentagon (c) polygons in 0.5 mm$^2$ area of AFM mica surface. Error represents counts from several independent images.

FIG. 16 shows thermodynamically stable RNA nanoparticles for efficient delivery of immunostimulatory CpG oligonucleotides, RNA or antigen to immune cells, FIG. 17 shows RNA and DNA sequence for triangle-3CpGs (SEQ ID NOS 78-85, 17, 19, and 21, respectively, in order of appearance)

FIG. 30 shows AFM images of RNA nanostructure triangles harboring three CpGs.

FIG. 31 shows detailed AFM images of RNA nanostructure triangles harboring three CpGs and a scheme of the CpG harboring RNA triangle. Triangle with 2 CpG ODN can be successfully purified and imaged by AFM. The image shows that triangle-CpG assemble well and most of the particles are shown as triangular shape. Based on the AFM image, the diameter of triangle with 3 CpG is around 30 nm, a bit larger than the original triangle.

FIG. 56 shows a schematic showing self-assembly of RNA triangle nanostructure harboring CpG RNAs, and the CpG RNA sequences with 21 nucleotide overhang and 5U linker.

FIG. 57 shows the sequence of A21 CpGRNA, the 63 nucleotide DNA, the 5' Primer and the 3' Primer.

FIG. 58 shows the sequence of B21 CpGRNA, the 63 nucleotide DNA, the 5' Primer and the 3' Primer.

FIG. 59 shows the sequence of C21 CpGRNA, the 63 nucleotide DNA, the 5' Primer and the 3' Primer.

DESCRIPTION OF THE SEQUENCE LISTING

Figure 1A:
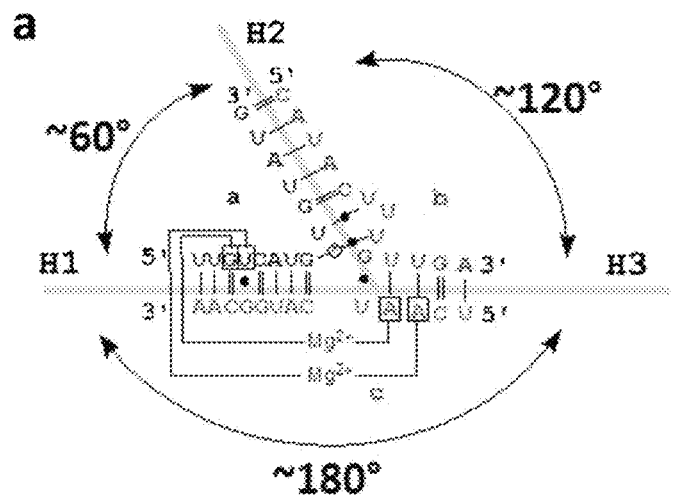
FIGS. 1A and 1B shows details of the structural features of the pRNA 3WJ motif. (A) Secondary structure of 3WJ motif with base pairs annotated using Leontis-Westhof nomen-clature. Figure discloses SEQ ID NOS 34-36, respectively, in order of appearance. (B) Tertiary structure of the 3WJ motif with indication of the ∠AOB~60° angle formed between H1 and H2. The ∠AOB Angle corresponds to inner angles of polygons.

SEQ ID NO 1 is an exemplary RNA sequence for Triangle short strand A used in assembly of an RNA triangle nanostructure.

SEQ ID NO 2 is an exemplary RNA sequence for Triangle short strand B used in assembly of an RNA triangle nanostructure.

SEQ ID NO 3 is an exemplary RNA sequence for Triangle short strand C used in assembly of an RNA triangle nanostructure.

SEQ ID NO 4 is an exemplary RNA sequence for Triangle long strand D used in assembly of an RNA triangle nanostructure.

SEQ ID NO 5 is an exemplary RNA sequence for Square short strand A used in assembly of an RNA square nanostructure.

SEQ ID NO 6 is an exemplary RNA sequence for Square short strand B used in assembly of an RNA square nanostructure.

SEQ ID NO 7 is an exemplary RNA sequence for Square short strand C used in assembly of an RNA square nanostructure.

SEQ ID NO 8 is an exemplary RNA sequence for Square short strand D used in assembly of an RNA square nanostructure.

SEQ ID NO 9 is an exemplary RNA sequence for Square long strand E used in assembly of an RNA square nanostructure.

SEQ ID NO 10 is an exemplary RNA sequence for pentagon short strand A used in assembly of an RNA pentagon nanostructure.

SEQ ID NO 11 is an exemplary RNA sequence for pentagon short strand B used in assembly of an RNA pentagon nanostructure.

SEQ ID NO 12 is an exemplary RNA sequence for pentagon short strand C used in assembly of an RNA pentagon nanostructure.

SEQ ID NO 13 is an exemplary RNA sequence for pentagon short strand D used in assembly of an RNA pentagon nanostructure.

SEQ ID NO 14 is an exemplary RNA sequence for pentagon short strand E used in assembly of an RNA pentagon nanostructure.

SEQ ID NO 15 is an exemplary RNA sequence for pentagon long strand F used in assembly of an RNA pentagon nanostructure.

SEQ ID NO 16 is an exemplary strand A21 CpG RNA.
SEQ ID NO 17 is an exemplary strand A21 CpG DNA.
SEQ ID NO 18 is an exemplary strand B21 CpG RNA.
SEQ ID NO 19 is an exemplary strand B21 CpG DNA.
SEQ ID NO 20 is an exemplary strand C21 CpG RNA.
SEQ ID NO 21 is an exemplary strand C21 CpG DNA.
SEQ ID NO 22 is an exemplary RNA sequence Tri A-Cpg for assembly of RNA Triangle harboring RNA CpG motif.

SEQ ID NO 23 is an exemplary RNA sequence Tri B-CpG for assembly of RNA Triangle harboring RNA CpG motif.

SEQ ID NO 24 is an exemplary RNA sequence Tri C-CpG for assembly of RNA Triangle harboring RNA CpG motif.

SEQ ID NO: 25 is a 63 nucleotide DNA sequence including the sequence of SEQ ID NO: 17, and SEQ ID NO: 26 and SEQ ID NO: 27 are 5'- and 3'-primers, as set forth in FIG. 57.

SEQ ID NO: 28 is a 63 nucleotide DNA sequence including the sequence of SEQ ID NO: 19, and SEQ ID NO: 29 and SEQ ID NO: 30 are 5'- and 3'-primers, as set forth in FIG. 58.

SEQ ID NO: 31 is a 63 nucleotide DNA sequence including the sequence of SEQ ID NO: 21, and SEQ ID NO: 32 and SEQ ID NO: 33 are 5'- and 3'-primers, as set forth in FIG. 59.

DESCRIPTION OF EXEMPLARY EMBODIMENTS

The details of one or more embodiments of the presently-disclosed subject matter are set forth in this document.

Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" comprises a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about" can encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. For example, the term "about" can refer to a value or an amount of mass, weight, time, volume, concentration, percentage, number, or temperature.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "sequence identity", "sequence similarity" or "homology" is used to describe sequence relationships between two or more nucleotide sequences.

The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa.

As used herein, "Adjuvant" refers to a composition, chemical or biological agent given in combination with a composition, an antibody, polynucleotide or polypeptide to enhance its immunogenicity.

The area of biomimetic nanotechnology involves the construction of nano-scale, supramolecular architectures utilizing modular units of functional nucleic acids. The aim is to design nanostructures that undergo self-assembly in controllable and recyclable fashion. Ribonucleic acid (RNA) was discovered as an attractive material to build nanoparticles via nanotechnology (1), offering a variety of structural modules and motifs that can be manipulated into 1D, 2D and 3D architectures (for review see (2)). In the past decade, a variety of geometric RNA nanoparticles and nano-scaffolds have been obtained via the approaches of hand-in-hand (1,3-5), foot-to-foot (6-9), branch extension (10-14), loop-receptor contact (15-17), 'sticky' or 'dangling' ends (6, 18, 19) and synthetic RNA-protein complex interactions (20). These motifs are available in data bases and can be used to build artificial nanostructures by manipulating their interchangeable units (21). Recently, RNA rolling cycle transcription has been utilized to generate RNA sponges (22,23). In RNA tectonics approach, structural motifs like double helices, loops and junctions can be isolated from large and complex RNA molecules appearing in structural data bases and used to build artificial nanostructures by manipulating their interchangeable units (24,25). As such, previously reported designs of RNA nanoparticles, e.g. tecto-square (26), square-shaped nano-scaffolds (27,28), RNA nano-rings (1, 5, 7, 9) or pRNA dimers, tetramers and hexamers (1, 7, 9, 29, 30), as well as RNA nano-cubes (19), RNA polyhedron (14), RNA bundles (6,31) and filaments (15,16) utilize fundamental principles of RNA structure and folding (32-36). Overall stability of conventional constructs though, mainly relies on the stability of canonical and non-canonical base pair (bp) forming by loop-loop, receptor-loop, or 'sticky-ends' with a number of pairing nucleotides usually not exceeding six. A new approach is needed to increase overall stability of RNA nanoparticles, one that uses naturally-selected stable RNA building blocks for structure building, and the example is the 3WJ motif from pRNA of bacteriophage phi29 DNA packaging motorional nucleic acids. The aim is to design nanostructures that undergo self-assembly in controllable and recyclable fashion. A new approach is needed to increase overall stability of RNA nanoparticles, one that uses naturally-selected stable RNA building blocks for structure building. An example is the 3WJ motif from pRNA of bacteriophage phi29 DNA packaging motor. In addition to discovering that the pRNA-3WJ shows exceptional stability under physiological conditions and in the presence of strong denaturing agent (10,11), recent studies also suggest that the thermodynamic stability of the 3WJ is entropy driven (37). Stable RNA polygons have the potential to serve as a new generation of delivery systems for immunomodulators.

Embodiments as described herein comprise compositions and adjuvants useful for prophylactic and therapeutic treatment. For example, embodiments comprise immunostimulatory RNA-containing compositions and RNA nanoparticle-containing compositions. The compositions described herein are safe, effective, versatile, and easy to manufacture, offering new solutions to address unmet needs associated with current approaches to vaccine design and development.

RNA can be used as a construction material, immunostimulatory agent, or a combination thereof for the development of new nanovaccines and adjuvants for disease prevention and treatment.

Ultrastable RNA nanoparticles comprising RNA, CpG DNA, peptide antigen or protein antigen can be pre-designed in silico and fabricated by thermodynamically-driven self-assembly. The fabricated RNA nanoparticle-based nanovaccine and adjuvants have pre-defined stoichiometry, size and structure, and are also thermodynamically ultrastable and resistant to degradation in serum. The cellular uptake of the RNA nanoparticle-based nanovaccine and adjuvants is greatly enhanced compared to CpG DNA only and antigen only. The immune response induced by the RNA nanoparticle-based nanovaccine and adjuvants will also be greatly enhanced compared to CpG DNA only and antigen only. The RNA nanoparticle-based nanovaccines and adjuvants could also be conjugated to a variety of targeting ligands for targeting to B cells, T cells, dendritic cells, macrophages, cancer cells, or a combination thereof. The targeting ligands comprises but are not limited to folate, RNA aptamers, DNA aptamers, or a combination thereof. In certain embodiments, multiple targeting ligands can be conjugated to one nanoparticle to enhance the targeting efficacy.

ssRNA, dsRNA and siRNA have been shown to have immunostimulatory activities. Embodiments as described herein comprise an immunostimulatory agent comprising chemically modified RNA. The chemically modified RNA comprises immunostimulatory motifs which comprises, but are not limited to, the CpG motif. Embodiments as described herein further comprise vaccine and adjuvant platforms that use the immunostimulatory RNA as one of the platform components. Moreover, the immunostimulatory RNA can also be incorporated into ultrastable RNA nanoparticles comprising RNA, CpG DNA, peptide antigen or protein antigen to form nanovaccines. The fabricated RNA nanoparticle-based nanovaccine and adjuvants have pre-defined stoichiometry, size and structure, and are also thermodynamically ultrastable and resistant to degradation in serum. The immune response induced by the immunostimulatory RNA platform will be greatly enhanced compared to CpG DNA only and antigen only. The immunostimulatory RNA platform could also be conjugated to a variety of targeting ligands for targeting to B cells, T cells, dendritic cells, macrophages, cancer cells, or a combination thereof. The targeting ligands comprise but are not limited to folate, siRNA, shRNA, RNA aptamers, DNA aptamers, or a combination thereof. In certain embodiments, multiple targeting ligands can be conjugated to one platform to enhance the targeting efficacy. The vaccine platform according to the invention and the adjuvants platform according to the invention are employed to treat or prevent various diseases comprising, but not limited to, cancer, immunology, respiratory, central nervous system, inflammatory, cardiovascular, infectious diseases, drug and substance abuse, or a combination thereof.

RNA-based compositions disclosed herein, including RNA-nanoparticle-containing and RNA-oligonucleotide-containing compositions, have a number of advantageous features. Such advantages comprises the following. The RNA-based compositions have defined size, structure and stoichiometry, such that unpredictable side effects arising from heterogeneous particles can be avoided. Due to the multivalent nature of RNA nanoparticles, multiple antigen and adjuvants could be incorporated into one particle for achieving synergistic or enhanced immune repose such as cytokine induction and antibody production. The nanosize of the particles will facilitate tissue penetration and target to important immune tissues or organs such as lymph nodes for achieving targeted and enhanced immune stimulation. Multiple targeting ligands could be incorporated into one particle for achieving better targeting to immune cells such as B cells, T cells, dendritic cells and macrophages. Economic and easy fabrication of RNA-based compositions could be performed in a cell-free system which allows for industrial scale production and avoids possible contamination. RNA nanoparticles are highly soluble and not prone to aggregation. They do not require any addition steps, such as linkage to PEG to keep them stable in solution. RNA nanoparticles are also thermodynamically stable. For example, the triangular shaped RNA nanoparticles are resistant to boiling. The three-way junction RNA nanoparticles are resistant to 8M urea denaturation. Thus RNA nanoparticles will remain intact and not disassociate at ultra-low concentrations in vivo. 2'F-modified RNA-based compositions, for example, are resistant to degradation in serum and stable in the blood. The cellular uptake of the RNA nanoparticle-based nanovaccine and adjuvants is greatly enhanced compared to CpG DNA only and antigen only. The immunostimulatory activity of the chemical modified RNA-based compositions disclosed herein is stronger than other adjuvants such as CpG DNA. Due to the larger size of RNA nanoparticle-based nanovaccine and adjuvants compared to antigen and adjuvants only, the in vivo half-life of RNA nanoparticle-based nanovaccine and adjuvants is significantly prolonged, offering better pharmacokinetics profiles and better patient compliance. The immunostimulatory RNA can also be incorporated into ultrastable RNA nanoparticles composed of RNA, CpG DNA, peptide antigen or protein antigen to form nanovaccine. The fabricated RNA nanoparticle-based nanovaccine and adjuvants have pre-defined stoichiometry, size and structure, and are also thermodynamically ultrastable and resistant to degradation in serum. The immune response induced by the immunostimulatory RNA platform will be greatly enhanced compared to CpG DNA only and antigen only. RNA-based compositions as described herein are ultrastable and resistant to degradation in serum, and can be conjugated to ligands to target, for example, B, T, dendritic, macrophage, cancer cells, or a combination thereof.

The presently-disclosed subject matter comprises a composition comprising an RNA-oligonucleotide and an immunostimulatory motif.

In some embodiments, the RNA-oligonucleotide comprises a chemical modification, examples of which comprise 2'Fluoro, 2'Amine, and 2'O-Methyl. In some embodiments, the RNA-oligonucleotide comprises about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 bases in length. In some embodiments, the RNA-oligonucleotide comprises at least one single-stranded RNA oligonucleotide. In other embodiments, the RNA-oligonucleotide comprises at least one double-stranded or partially double-stranded (e.g., containing a hair-pin) RNA oligonucleotide.

In some embodiments, the immunostimulatory motif comprises an immunostimulatory RNA (isRNA) and a CpG oligodeoxyribonucleotide (CpG). The isRNA can be any isRNA known to the skilled artisan, examples of which are set forth in Patent Application Publication Nos. US 2014/0135487 and WO 2003/086280, which are incorporated by reference in their entireties. In some embodiments, the immunostimulatory motif is conjugated to the RNA-oligonucleotide. In some embodiments, the immunostimulatory motif is CpG conjugated to the RNA-oligonucleotide.

In some embodiments, the composition comprising an RNA-oligonucleotide and an immunostimulatory motif is provided as an adjuvant. In some embodiments, the immune modulation effect for cytokine induction is increased at least about ten fold as compared to the immunostimulatory motif provided independently of the RNA-oligonucleotide. In some embodiments, the immune modulation effect for cytokine induction is increased at least about two fold, three fold, four fold, five fold, six fold, seven fold, eight fold, nine fold, fifteen fold, twenty fold, thirty fold, forty fold, fifty fold as compared to the immunostimulatory motif provided independently of the RNA-oligonucleotide. In some embodiments when immunostimulatory motif is conjugated to the RNA-oligonucleotide, the immune modulation effect for cytokine induction and cell binding is enhanced at least 10, at least 20, at least 30, at least 40, at least 50, at least 75, at least 100, at least 150, or at least 200 times.

Embodiments as described herein comprise a composition comprising an RNA nanostructure, and an adjuvant, an antigen, and/or a targeting ligand. Examples of RNA nanostructures comprise RNA triangle, RNA square, RNA pentagon, RNA hexagon, RNA three-way junction, RNA four-way junction In some embodiments, the RNA nanostructure comprise an RNA triangle, RNA square, RNA pentagon, RNA hexagon, RNA three-way junction, RNA four-way junction. In some embodiments, the RNA nanostructure is derived from a 3WJ motif. A non-limiting example of the RNA nanostructure comprises an RNA nanostructure that is derived from the 3WJ motif, such as that described in the Examples herein. Other RNA nanostructures are known to those skilled in the art, for example that which is found in International Patent Application Publication No. WO 2012/170372, which is incorporated by reference in its entirety.

In embodiments as described herein, the adjuvant comprises an immunostimulatory RNA (isRNA), a CpG oligodeoxyribonucleotide (CpG), or a combination thereof. In some embodiments, the isRNA, can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or about 35 bases in length. In some embodiments the isRNA is about 8 to about 30 bases in length. In some embodiments, the adjuvant comprises isRNA and the isRNA is incorporated into the RNA nanoparticle by base pairing. In some embodiments, the adjuvant comprises isRNA and the isRNA is incorporated into the RNA nanoparticle by being covalently bonded to an RNA strand of the RNA nanoparticle. In some embodiments, the adjuvant comprises a composition as described herein, an example of which comprises an RNA-oligonucleotide and an immunostimulatory motif. In some embodiments, the RNA-oligonucleotide and immunostimulatory motif are incorporated into the RNA nanoparticle by base pairing between the RNA-oligonucleotide and the RNA nanoparticle. In some embodiments, the RNA-oligonucleotide and immunostimulatory motif are incorporated into the RNA nanoparticle by the RNA-oligonucleotide being covalently bonded to an RNA strand of the RNA nanoparticle.

Embodiments as described here comprise an antigen, non-limiting examples of which can be derived from a bacteria, virus, or cell. In some embodiments, the antigen binds to a neutralizing antibody or an inhibitory antibody. In some embodiments, the antigen comprises a neutralizing epitope. In some embodiments, the antigen comprises a B-cell epitope, T-cell epitope, T-helper epitope, epitopes derived from PG120, gp41 epitopes, glycans, peptides, T-helper peptides, streptavidin, or combination thereof.

Embodiments as described herein comprise a targeting ligand, non-limiting examples of which comprise an aptamer, a cell surface marker, a cancer cell, or a combination thereof. In some embodiments, where the targeting ligand comprises an aptamer, the aptamer can bind to at least one HIV epitope. In some embodiments, where the targeting ligand comprises a cell surface marker, the cell surface marker comprises a macrophage or a lymphocyte. In some embodiments, the composition comprises at least two targeting ligands. In some embodiments, the composition comprises one, two, three, four, five, six, seven, eight, nine, or ten targeting ligands. In some embodiments the multiple targeting ligands are the same. In other embodiments, the targeting ligands are different. In some embodiments, not all of the multiple targeting ligands are the same.

As will be appreciated by the skilled artisan, compositions disclosed herein can be formulated to comprises a pharmaceutically-acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles comprises water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can comprise sugars such as lactose. Desirably, at least 95% by weight of the particles of the active ingredient have an effective particle size in the range of 0.01 to 10 micrometers.

The presently-disclosed subject matter further comprises methods as disclosed herein. For example, a method of inducing an immune response in a subject comprises administering to the subject an effective amount of a composition as described herein. In some embodiments, the subject has or is at risk of having a pathological condition. Embodiments as described herein further comprises a method of inducing the production of cytokines comprising administering to a subject an effective amount of a composition as described herein. In some embodiments, the cytokines comprise TNF-alpha, IL-6, IL-12, or a combination thereof. The presently-disclosed subject matter further comprises a method of inducing the production of high affinity neutralizing antibodies or inhibitory antibodies comprising administering a composition as described herein to a subject having a pathological condition. Exemplary pathological conditions comprises, but are not limited to, cancer, immunology, respiratory, central nervous system, inflammatory, cardiovascular, infectious diseases, influenza, human immunodeficiency virus (HIV), and drug and substance abuse, such as cocaine or nicotine abuse.

As used herein, the term "subject" refers to a target of administration. The subject of the herein described methods can be a vertebrate, such as a mammal, a fish, a bird, a reptile, or an amphibian. Thus, the subject of the herein described methods can be a human or non-human. Thus, veterinary therapeutic uses are provided in accordance with the presently described subject matter. As such, the presently described subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals comprise but are not limited to carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. The term does not denote a particular age or sex.

The presently-described subject matter is further illustrated by the following specific but non-limiting examples. The following examples may comprise compilations of data that are representative of data gathered at various times during the course of development and experimentation related to the present invention.

EXAMPLES

Modulation of immune response is important in cancer immunotherapy, vaccine adjuvant development and inflammatory or immune disease therapy. Here we report the development of new immunomodulators via control of shape transition among RNA triangle, square and pentagon nanostructures. Changing one RNA strand in polygons automatically induced the stretching of the interior angle from 60° to 90° or 108°, resulting in self-assembly of elegant RNA triangles, squares and pentagons. When immunological adjuvants were incorporated, their immunomodulation effect for cytokine TNF-a and IL-6 induction was greatly enhanced in vitro and in animals up to 100-fold, while RNA polygon controls induced unnoticeable effect. The RNA nanoparticles were delivered to macrophages specifically. The degree of immunostimulation greatly depended on the size, shape and number of the payload per nanoparticles. Stronger immune response was observed when the number of adjuvants per polygon was increased, demonstrating the advantage of shape transition from triangle to pentagon.

By stretching the 60° AOB angle (∠) (FIG. 1) of the thermodynamically stable pRNA 3WJ motif, stable RNA architectures can be designed. We demonstrate that it can be stretched to wide conformations resulting in different 2D polygons: triangle (∠AOB=) 60°, square (∠AOB=90°) and pentagon (∠AOB=108°). Intermolecular interactions such as kissing loops, receptor loop, or 'sticky-ends' were avoided by introducing linkages through base pairing between corners of the polygons using RNA double helices. Therefore, this system is advantageous with an increased thermo-stability in the overall construct.

We further demonstrate that the RNA polygons have the potential to serve as a new generation of delivery systems for immunomodulators. Synthetic unmethylated cytosine-phosphate-guanine oligodeoxynucleotides (CpG ODN) are immunostimulatory DNA molecules that mimic the immunostimulatory activity of bacterial DNA (38,39). CpG DNA motifs strongly activate the mammalian innate immune system by interacting with various immune cells via endosomal Toll-like receptor 9 (TLR9) (40,41). Upon the stimulation by CpG DNA, immune cells could secret a variety of proinflammatory and antiviral cytokines including tumor necrosis factor-alpha (TNF-alpha, or TNF-α), interleukin-6 (IL-6), interleukin-12 (IL-12) and interferon (IFN), which leads to potent immune response. The therapeutic potential of CpG DNA has also been extensively explored in both basic research and human clinical trials, including the development of new vaccine adjuvants, anticancer agents, immunoprotective agents and anti-allergic agents (42-45). Recently, several groups have reported the utilization of DNA nanostructures such as DNA tetrahedrons (46), DNA polypod-like structures (47), DNA origami structures (48), Y-shaped DNA (49) and DNA dendrimers (50) to deliver immunostimulatory CpG DNA. In this work, to the best of our knowledge, we report the first use of RNA nanostructures to deliver CpG DNA in vitro and in vivo. The immunostimulatory efficacy of RNA polygons was evaluated by measuring the release of cytokines. We found that the induction of cytokines is highly dependent on the number of CpG per polygon. With increasing number of CpG per polygon, stronger immune response was observed, demonstrating the advantage of the transition from a triangle to a pentagon that can carry five CpGs.

We also report RNA CpG. The characteristic of RNA that differentiates it from DNA is the 2'-hydroxyl (2'-OH) on each ribose sugar of the backbone. The 2'-OH group offers RNA a special property. From a structural point of view, the advantage of this additional hydroxyl group is that it locks the ribose sugar into a 3'-endo chair conformation, and it will be structurally favorable for the RNA double helix to adopt the A-form helix rather than the B-form helix that is typically present in the DNA. From a thermodynamic point of view, remarkably, the RNA double helix is more thermodynamically stable than the DNA double helix considering $\Delta G0$ for RNA double helix formation is −3.6 to −8.5 kJmol-1 per base pair stacked and $\Delta G0$ for DNA double helix formation is −1.4 kJmol-1 per base pair stacked. Moreover, the presence of special structures such as bends, stacks, junctions and loops in the 3D structure of RNA as well as various proteins and metal ions may also further improve its stability. Similar to DNA CpG sequence, RNA CpG sequence can also induce immune response and can be applied to the development of cancer immunotherapy and vaccine adjuvants.

Materials and Methods

RNA Nanoparticles Design, Synthesis and Self-Assembly

The 3WJ crystal structure of the pRNA molecule (PDB ID: 4KZ2) was primarily used for designing polygon models using Swiss PDB viewer, as previously described (51). RNA strands for corresponding triangle, square and pentagon, were synthesized by in vitro T7 transcription using polymerase chain reaction (PCR) generated DNA templates. RNAs were purified by denaturing polyacrylamide gel electrophoresis (PAGE) and were either Cy5 whole body RNA labeled (Minis Bio LLC) or 5'-end [-32P] ATP (PerkinElmer) labeled, as previously described (8).

RNA polygons were assembled in one pot by mixing equimolar concentrations (final concentration of 1 IIM) of four RNA strands for the triangle, five RNA strands for the square and six RNA strands for the pentagon in 1×TMS buffer (50 mM TRIS pH 8.0, 100 mM NaCl and 10 mM MgCl2). Samples were annealed for 1 h in a thermocycler with controlled, slow cooling (1° C./min) from 80 to 4° C. All RNA polygons harboring CpG ODNs were assembled from their corresponding 2'F-U/C modified strands in one pot.

The three short RNA strands and one long RNA strands for assembly of the RNA polygon are provided in Table 1.

TABLE 1

RNA Triangle Nanostructure

| | RNA Sequence | SEQ. ID NO |
|---|---|---|
| Triangle short strand A | 5'GGGAGCCGUCAAUCAUGGCAAGUGUCCGCCAUACUUUG UUGCACGCAC -3' | 1 |
| Triangle Short Strand B | 5'GGGAGCGUGCAAUCAUGGCAACGAUAGAGCAUACUUUG UUGGCUGGAC -3' | 2 |
| Triangle Short Strand C | 5'GGGACCAGCCAAUCAUGGCAAUAUACACGCAUACUUUG UUGACGGCGG -3' | 3 |
| Triangle Long Strand D | 5'GGACACUUGUCAUGUGUAUGCGUGUAUAUUGUCAUGUG UAUGCUCUAUCGUUGUCAUGUGUAUGGC -3' | 4 |

The four short strands and one long strand for assembly of the square RNA nanostructure are provided in Table 2.

TABLE 2

RNA Square Nanostructure

| | RNA Sequence | SEQ. ID NO |
|---|---|---|
| Square Short Strand A | 5'GGGAGCCGUCAAUCAUGGCAAGUGUCCGCCAUAC UUUGUUGCACGCAC -3' | 5 |
| Square Short Strand B | 5'GGGAGCGUGCAAUCAUGGCAAGCGCAUCGCAUAC UUUGUUGCGACCUA -3' | 6 |
| Square Short Strand C | 5'GGGAGGUCGCAAUCAUGGCAACGAUAGAGCAUA CUUUGUUGGCUGGAC -3' | 7 |
| Square Short Strand D | 5'GGGACCAGCCAAUCAUGGCAAUAUACACGCAUAC UUUGUUGACGGCGG -3' | 8 |
| Square Long Strand E | 5'GGACACUUGUCAUGUGUAUGCGUGUAUAUUGUC AUGUAUGCUCUAUCGUUGUCAUGUGUAUGCGA UGCGCUUGUCAUGUGUAUGGC -3' | 9 |

The five short strands and one long strand for assembly of the pentagon RNA nanostructure are provided in Table 3.

TABLE 3

RNA Pentagon Nanostructure

| | RNA Sequence | SEQ. ID NO |
|---|---|---|
| Pentagon Short Strand A | 5'GGGAGCCGUCAAUCAUGGCAAGUGUCCGCCAUAC UUUGUUGUAGGGCA -3' | 10 |
| Pentagon Short Strand B | 5'GGGACCCUACAAUCAUGGCAAAUAUGCGCCAUAC UUUGUUGCACGCAC -3' | 11 |
| Pentagon Short Strand C | 5'GGGAGCGUGCAAUCAUGGCAAGCGCAUCGCAUAC UUUGUUGCGACCUA -3' | 12 |
| Pentagon Short Strand D | 5'GGGAGGUCGCAAUCAUGGCAACGAUAGAGCAUA CUUUGUUGGCUGGAG -3' | 13 |
| Pentagon Short Strand E | 5'GGGACCAGCCAAUCAUGGCAAUAUACACGCAUAC UUUGUUGACGGCGG -3' | 14 |
| Pentagon Long Strand F | 5'GGACACUUGUCAUGUGUAUGCGUGUAUAUUGUC AUGUGUAUGCUCUAUCGUUGUCAUGUGUAUGCGA UGCGCUUGUCAUGUGUAUGGCGCAUAUUUGUCAUG UGUAUGGC -3' | 15 |

Table 4 provides sequences for CpG motifs.

TABLE 3

CpG motifs

| | RNA Sequence | SEQ. ID NO |
|---|---|---|
| A21 CpG | 5'-UCCAUGACG UUCCUGACGU UUUUUUUACA GUCGUAUUGC AUUCCGA-3' | 16 |
| | 5'-TCCATGACG TTCCTGACGT TTTTTTTACA GTCGTATTGC ATTCCGA-3' | 17 |
| B21 CpG | 5'-UCCAUGACGU UCCUGACGUU UUUUCCAUA CCGCAUUUC CAACUA-3' | 18 |
| | 5'-TCCATGACGT TCCTGACGTT TTTTCCATA CCGCATTTC CAACTA-3' | 19 |
| C21 CpG | 5'-UCCAUGACGU UCCUGACGUU UUUUAAGCA CAUGCGAUGU UUAACU-3' | 20 |
| | 5'-TCCATGACGT TCCTGACGTT TTTTAAGCA CATGCGATGT TTAACT-3' | 21 |

Table 5 provides the sequences for the RNA Triangle harboring the RNA CpG motif.

TABLE 5

RNA Triangle Nanostructure Harboring RNA CpG motif

| | RNA Sequence and DNA Sequence | SEQ. ID NO |
|---|---|---|
| Tri A-CpG | 5'- GGUCCAUGAC GUUCCUGACG UUUUUUUGGG CCGUCAAU CAUGGCAAGU GUCGC CAUAC UUU GUUGCACGCC C -3' | 22 |
| Tri B-CpG | 5'- GGUCCAUGAC GUUCCUGACG UUUUUUUGGG CGUGCAAU CAUGGCAACG AUAGAGCAUA C UUU GUUGGCUGGG C -3' | 23 |
| Tri C-CpG | 5'- GGUCCAUGAC GUUCCUGACG UUUUUUUGGC CAGCCAAU CAUGGCAAUA UACACGCAUA C UUU GUUGACGGCC C -3' | 24 |

Native PAGE, Temperature Gradient Gel Electrophoresis (TGGE) and Boiling Resistance Assays RNA assemblies were evaluated on 7% (29:1) native poly-acrylamide gels in the presence of 0.5×TMS buffer. Gels were run at constant 90 V, +4° C. Gels were imaged with Typhoon FLA 7000 (GE Healthcare) to visualize RNA strands. Temperature gradient gel electrophoresis (TGGE) analysis was performed on 7% native PAGE in a buffer containing 50 mM TRIS pH 8.0, 100 mM NaCl and 0.2 mM $MgCl_2$, as previously described (14, 26, 28). A gradient temperature of 30-70° C. was applied perpendicular to electrical current and the experiment was run for 1 h at 20 W. A total RNA concentration of 100 nM was used in TGGE analysis. Apparent TM values corresponded to the temperature at which half of the polygons fractions were dissociated and apparent KD values for multiple RNA strands were calculated, as described previously (7).

Boiling resistance assay was performed in 10 Ill containing 1 IIM preassembled polygons in TMS buffer or in the presence of 8M urea. Samples were incubated at 100° C. for several minutes, then snap cooled on dry ice to prevent refolding following evaluation on 7% native PAGE at 4° C. Individual experiments were repeated several times to reduce error.

Quantification analysis was performed using ImageJ (52). Equal-sized boxes were drawn around the lanes corresponding to the triangle, square, or pentagon complexes and corresponding quantified values for each type of polygon were divided by the sum of the values presented in the corresponding lane.

Cell Cultures

Mouse macrophage-like RAW 264.7 cells were grown in Dulbecco's Modified Eagle's Medium supplemented with 10% fetal bovine serum, 100 units/ml penicillin and 100 mg/ml streptomycin at 37° C. in humidified air containing 5% CO2. Cells were then seeded on 24-well plates or 96-well plates at a density of 5×105 cells/ml and cultured overnight before use.

Cytokine Secretion from RAW264.7 Cells

RAW 264.7 cells were plated into 24-well plates with the density of 2.5×105 cells per well and cultured overnight.

Then, RNA nanoparticles harboring different numbers of CpG ODNs were diluted in Opti-MEM medium (Life Technologies Corporation, Carlsbad, Calif., USA) and added to the cells. The cells were continually cultured for 8 h at 37° C. in humidified air containing 5% CO2, and the cell culture supernatant were collected and stored at −80° C. until use. The concentration of TNF-α and IL-6 in the supernatant were determined by enzyme-linked immunosorbent assay (ELISA) using Mouse ELISA MAX™ Deluxe sets (BioLegend, Inc., San Diego, Calif.), following protocols provided by the manufacturer.

Cytokine Secretion from Mice

Male CD-1 mice (4-5 weeks old) were purchased from Charles River Laboratories. All animal procedures were approved by the Institutional Animal Care and Use Committee at University of Kentucky and were performed in accordance with guidelines issued by the National Institutes of Health for the care of laboratory animals. For in vivo immunostimulation, RNA triangular nanoparticles harboring CpG ODN, RNA triangular nanoparticles, or CpG ODN were dissolved in phosphate buffered saline (PBS) and administrated to the mice via tail vein injection at 2 mg/kg (CpG ODN per body weight). The same volume of PBS was injected into a mouse as a control. Blood samples were collected 3 h post-injection by cardiac puncture. Serum was prepared by centrifugation at 12 800 g for 10 min. Serum TNF-a and IL-6 levels were determined by enzyme-linked immunosorbent assay (ELISA) using Mouse ELISA MAX™ Deluxe sets (BioLegend, Inc., San Diego, Calif., USA), following protocols provided by the manufacturer.

Confocal Microscopy Imaging

RAW 264.7 cells were seeded on glass coverslips in 24-well plates and cultured at 37° C. in humidified air containing 5% CO2 overnight. The culture medium was removed and the cells were washed with Opti-MEM medium twice to remove dead cells. RNA nanoparticles harboring Cy3-labeled CpG DNA or Cy3-labeled CpG DNA only were diluted in Opti-MEM medium and added to the cells. After 4 h incubation at 37° C. in humidified air containing 5% CO2, the cells were washed twice with PBS and fixed with 4% formaldehyde. ProLong R Gold Antifade Reagent with DAPI (Life Technologies Corporation, Carlsbad, Calif.) was used to stain the cell nucleus and mount the samples. Alexa FluorR 488 phalloidin (Life Technologies Corporation, Carlsbad, Calif., USA) was used to stain actin. The images were obtained on a Olympus FV1000 confocal microscope (Olympus Corporation, Tokyo, Japan).

Atomic Force Microscopy Imaging

RNA polygons were imaged with MultiMode AFM NanoScope IV system (Veeco), as per previously reported methods (61). Briefly, the RNA samples were diluted with 1×TMS buffer to a final concentration of 3-5 nM. Then, droplets of samples (5-10 L) were immediately deposited on APS mica. After 2 min incubation on the specifically modified APS mica surface (41;42), excess samples were washed with DEPC treated water and dried under a flow of Argon gas. AFM images in air were acquired using MultiMode AFM NanoScope IV system (Veeco/Digital Instruments, Santa Barbara, Calif.) operating in tapping mode.

Dynamic Light Scattering

Apparent hydrodynamic sizes of preassembled triangle, square, and pentagon complexes (10 μM) in 504, TMS buffer were measured by Zetasizer nano-ZS (Malvern Instrument, LTD) at 25° C. The laser wavelength was 633 nm.

Flow Cytometry Assay

RAW264.7 cells were detached from the cell culture flask by using a cell scraper. The cells were washed with Opti-MEM medium and aliquot in 1.5 mL Eppendorf tubes at the density of 5×105 cells per tube. RNA nanoparticles harboring Cy3-labeled CpG DNA or Cy3-labeled CpG DNA only were diluted in Opti-MEM medium and incubated with the cells at 37° C. for 1.5 h. The cells were vortexed every 30 min during the incubation. After washing with PBS, the cells were resuspended in PBS and the intensity of fluorescence was determined by FACSCalibur flow cytometer (BD Biosciences, San Jose, Calif.).

Cytotoxicity Assay

The cytotoxicity of RNA nanoparticles harboring CpG ODNs was evaluated with an MTT assay kit (Promega, Madison, Wis.), according to the protocol provided by the manufacturer. Briefly, RAW 264.7 cells were seeded at 96 well plates and cultured overnight at 37° C. in humidified air containing 5% CO2. RNA nanoparticles harboring CpG ODNs and controls were dissolved in fresh cell culture medium at the indicated concentrations and added to the cells for incubation at 37° C. for 24 h. Then, 15 μL of the dye solution was added to each well, followed by a 4 h incubation at 37° C., Next, 100 μl of the solubilization solution was added to each well and the plate was future incubated at room temperature on a plate shaker until the formazan crystals were completely solubilized. The absorbance was measured at 570 nm using a microplate reader. The cell viability was calculated relative to the absorbance of the cell only control (viability of cell only control=1).

RNA Polygons: Triangle, Square and Pentagon Fabrication and Self-Assembly

Figure 1B:
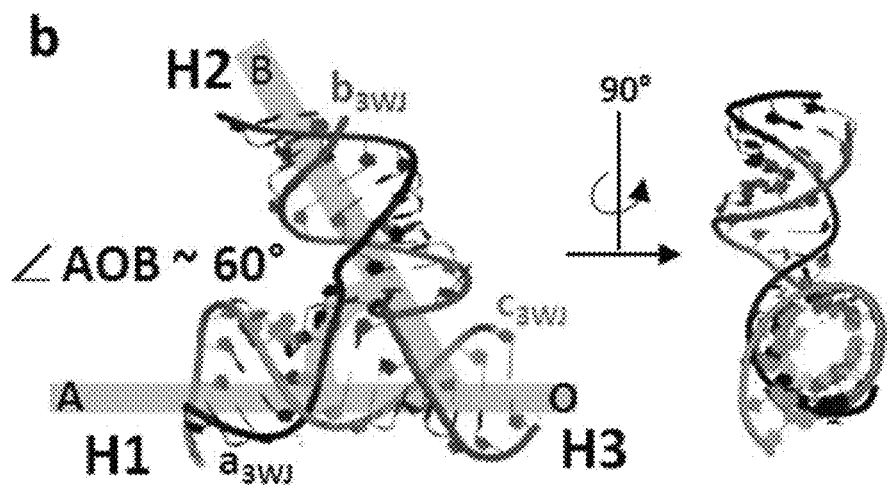
Figure 2A:
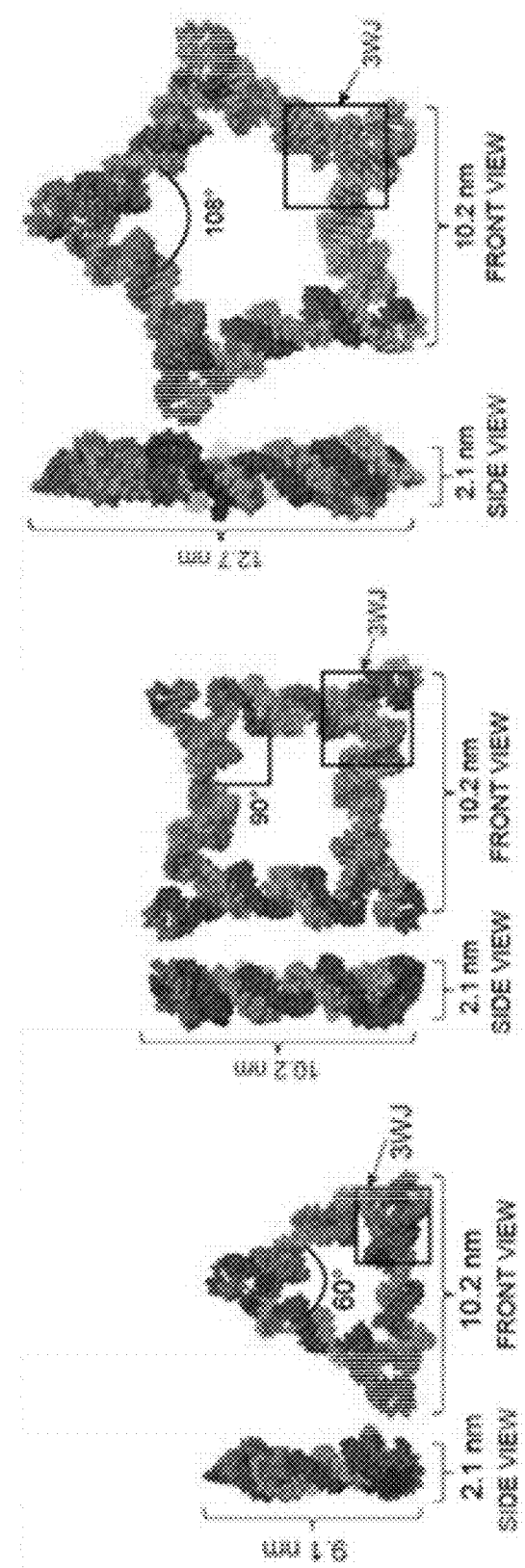
FIGS. 2A-2C shows the design of RNA nanostructure polygons and assembly properties. (A) 3D modeled structures of polygons with 3WJ motif located at vertices, inner angle corresponds to ∠AOB 60°. (B) The increasing length of the internal strand stretches the 3WJ ∠AOB at which the nanoparticles assemble, along with increasing number of external 'short' strands.

The structural features of the recently discovered ultrastable pRNA 3WJ module from the bacteriophage Phi29 DNA packaging motor were utilized for in silico design of the RNA triangle, square and pentagon 2D polygons. During the computer modeling we used the particular angle of the 3WJ formed by H1 and H2 as an inner angle of the polygons as we hypothesized that the angle could be stretched to a more open conformation. Throughout this report the intra-helical angle between H1 and H2 is denoted as ∠AOB, as shown in FIG. 1. Each RNA model contained a pRNA 3WJ motif at each vertex, and the inner angles correspond to ∠AOB. The resulting 3D models exhibited flat conformations, as expected from the plane geometry of the 3WJ motif (51) (FIG. 2A). As used herein, vertex refers to a point of an angle, such as ∠AOB, and vertex refers to a corner of a polygon. By way of example, and with reference FIG. 2B, the triangular polygon defined by internal strand D and external strands A, B, and C, includes three vertexes; the square polygon defined by internal strand E and external strands A, B, C, and D, includes four vertexes; and the pentagon polygon defined by internal strand F and external strands A, B, C, D, and E, includes five vertexes.

Figure 2B:
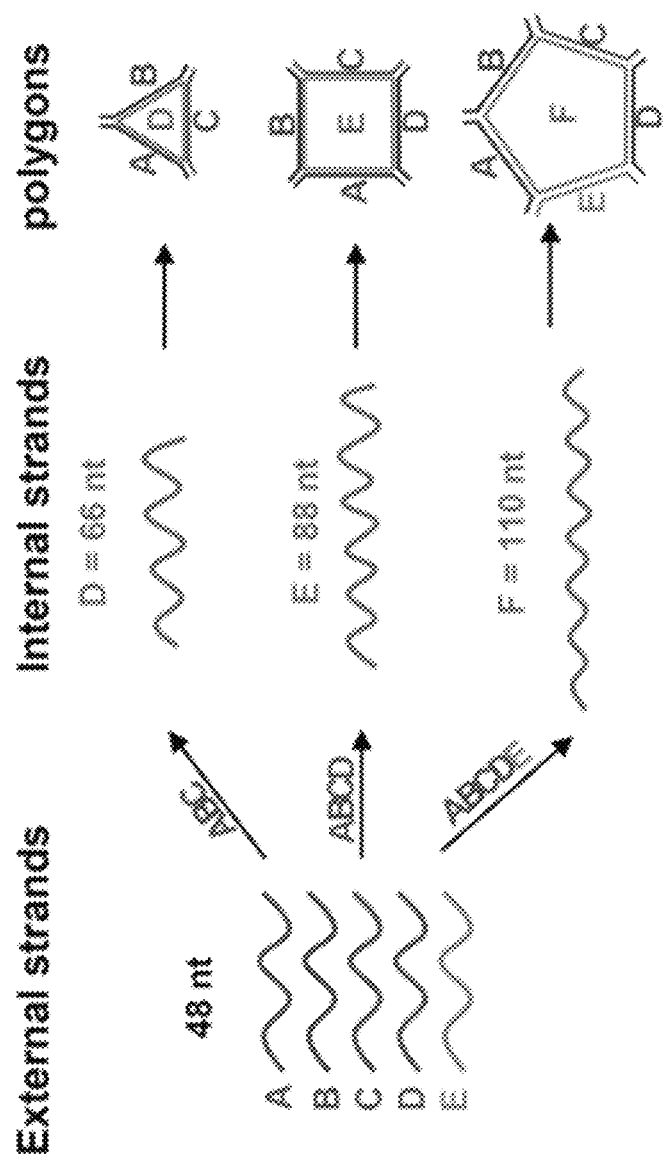
Figure 2C:
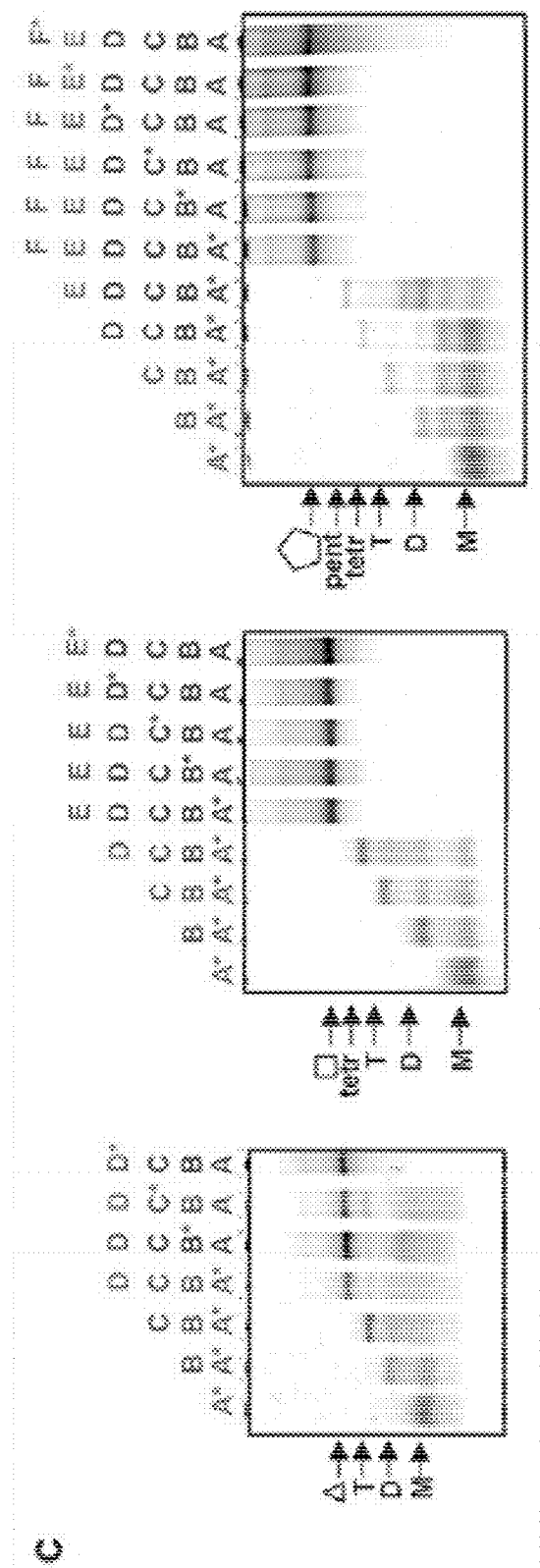

Each polygon was composed of a different number of RNA strands classified as short strands (external) and long strands (internal) (FIG. 2B). By increasing the number of external strands and the propagation of the central or internal strand, the tension on the inter-helical ∠AOB increased to 60°, 90° and 108°, allowing for 2D formation of corresponding triangle, square and pentagon shapes. The measured widths, from one corner to another, were 10.2 nm, while the heights differed as follows: triangle=9.1 nm, square=10.2 nm and pentagon=12.7 nm. Following the transcription of individual RNA strands, self-assembly properties of the triangle, square and pentagon designs were evaluated on 7% native polyacrylamide gel electrophoresis (PAGE) (FIG.

Figures 7A, 7B, 7C:
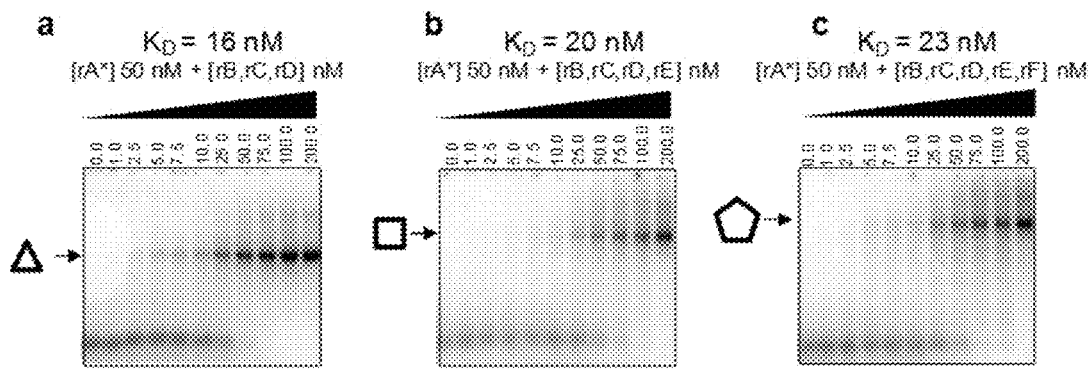
FIGS. 7A-7D shows RNA polygons dissociation constant determination at equilibrium state. These are 7% native PAGE titration data for formation of triangle (a), square (b), and pentagon (c) polygons. Below, the gels is the plot used to determine the equilibrium concentration for each polygon which were then used to calculate the apparent dissociation constant.
Figure 7D:
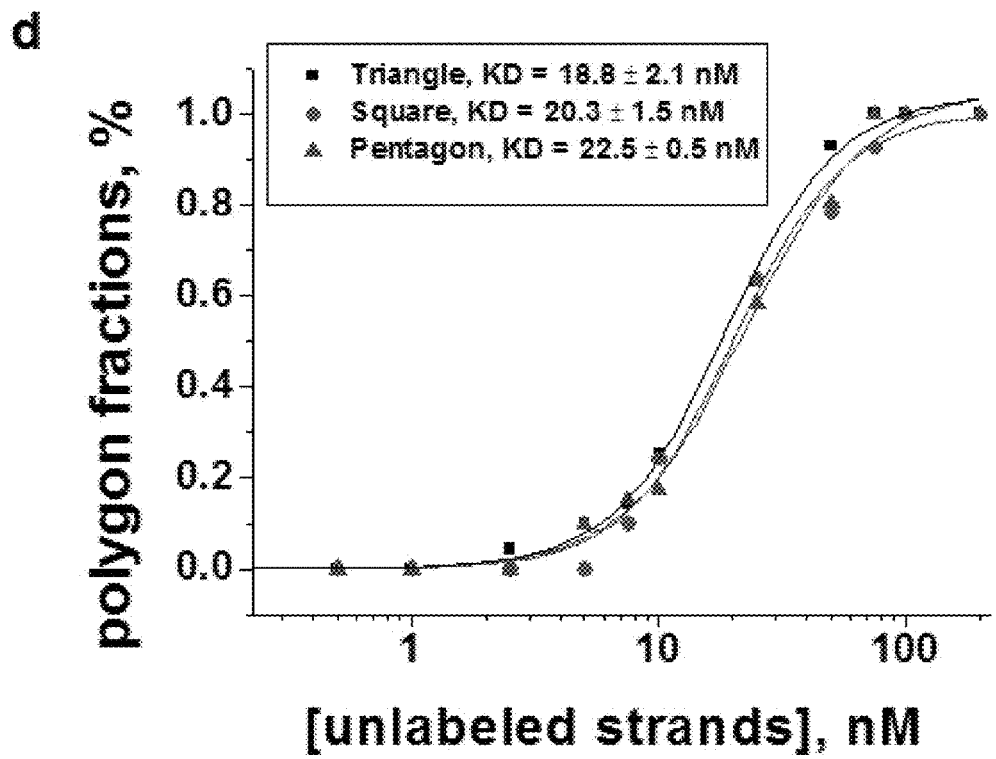
Figure 8A:
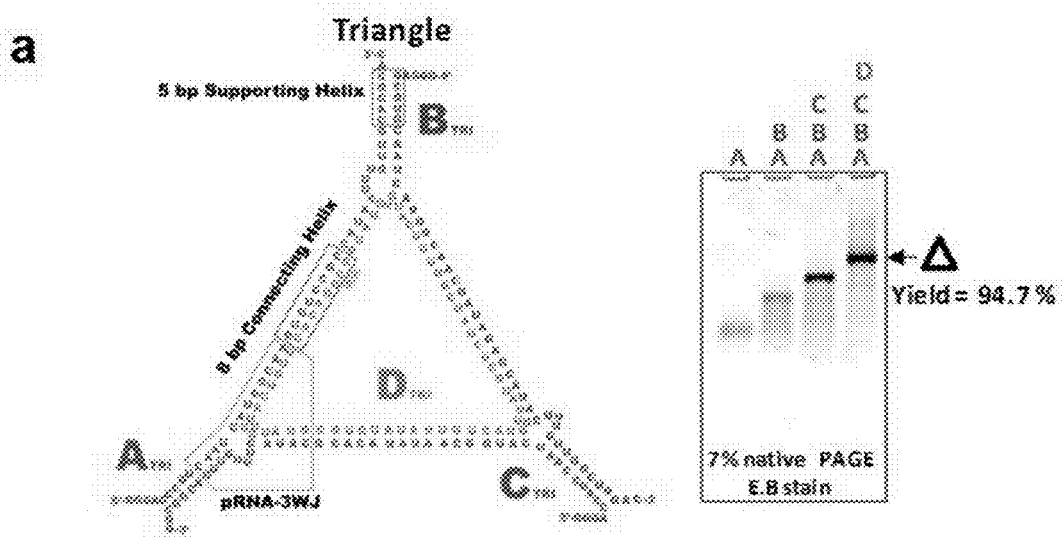
FIGS. 8A-8C shows sequences and secondary structures of RNA polygons. RNA polygons and quantified assembly yields for triangle (a), square (b) and pentagon (c).
Figure 8B:
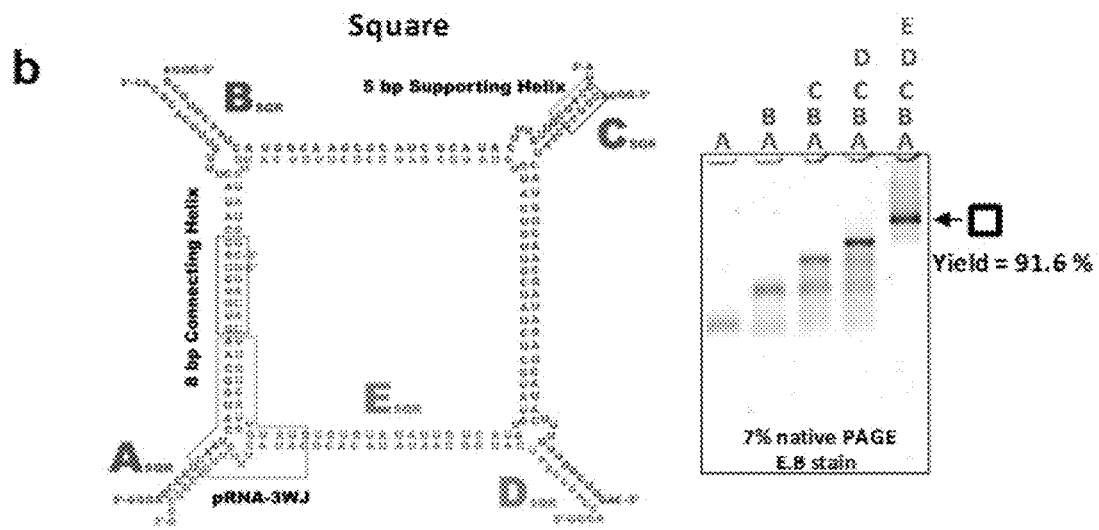
Figure 8C:
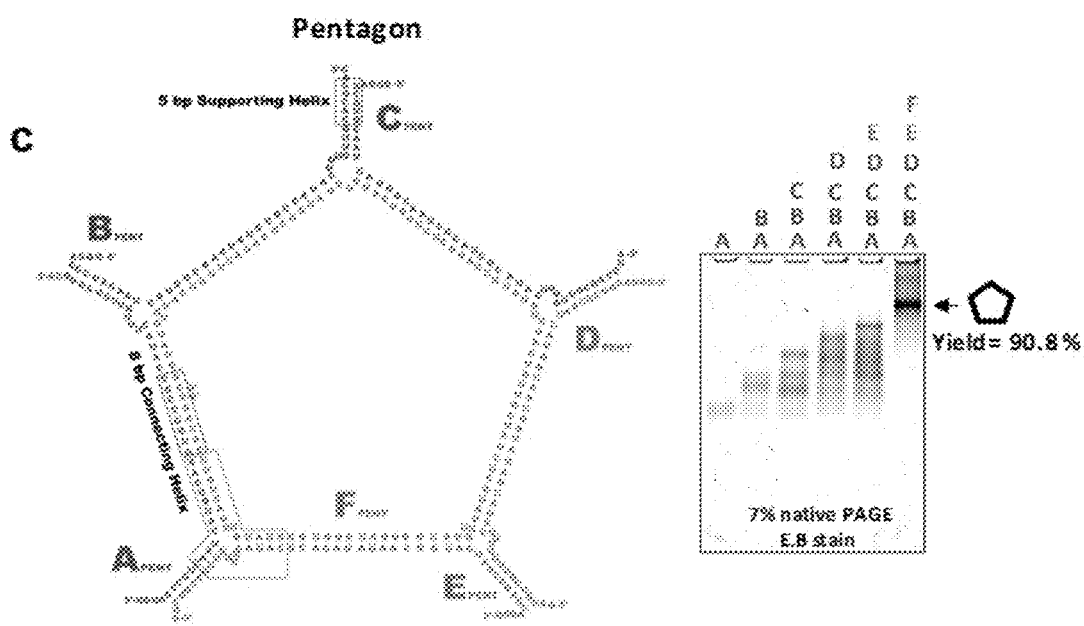

2C). All polygon formations were obtained by one-step self-assembly (7, 10, 11, 19). Each RNA component of corresponding nanoparticles were whole chain labeled with Cy5 to evaluate participation of all RNA strands in their corresponding assemblies. Yield of correctly assembled polygons was estimated to be >90% based on native PAGE gel evaluations. Equilibrium constants of dissociation were obtained from apparent KD gels, and KD values were determined to be 18.8, 20.3 and 22.5 nM for triangles, squares and pentagons, respectively (FIGS. 7 and 8).

These results demonstrate that each RNA nanoparticle assembles into the desired nanostructure, and indicated by a stretching of the 60. ∠AOB to wider conformations. The assembly of RNA strands into specific-shaped nanoparticles based on the 60. ∠AOB of the pRNA 3WJ motif was controlled by modulating the number of short external stands and the length of the long internal strand.

Figure 3:
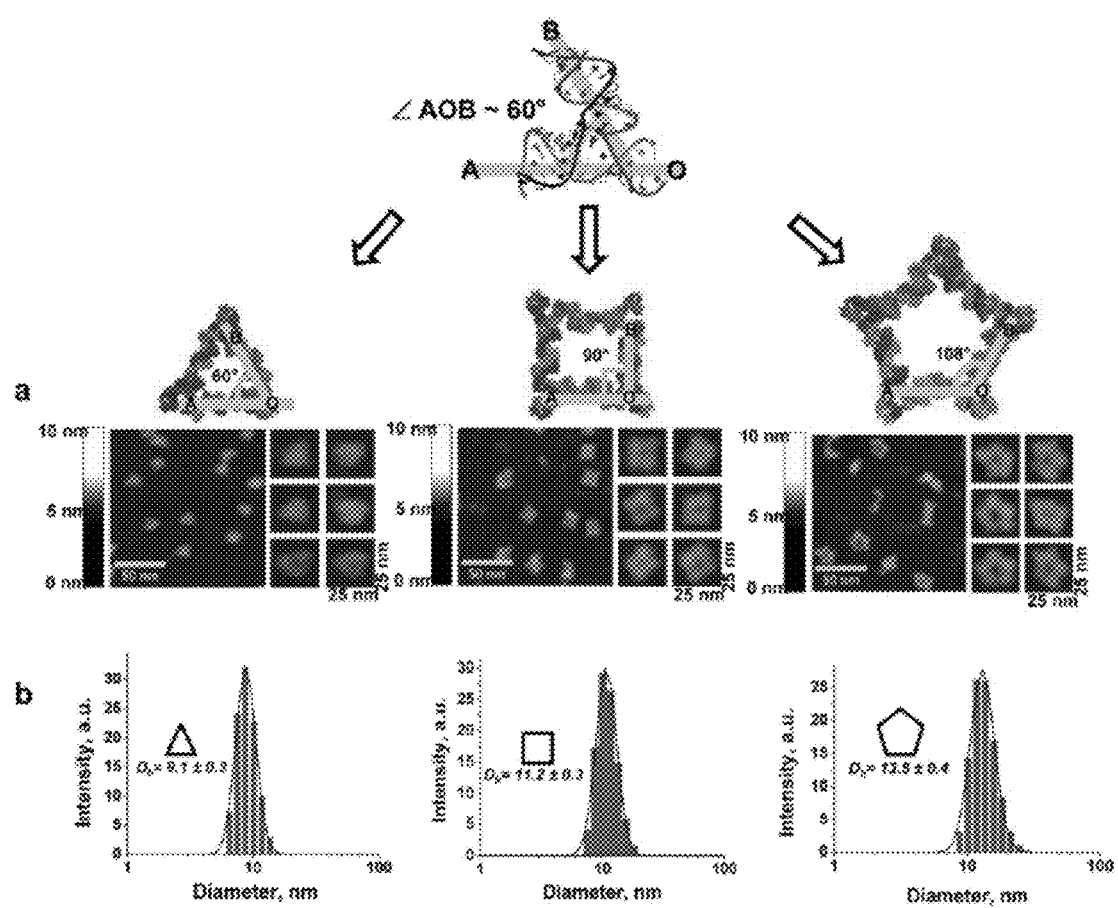
FIG. 3 shows structural characterization of polygons. (A) Atomic Force Microscopy (AFM) images of triangular, square and pentagonal nanoparticles derived from the pRNA 3WJ motif. (B) Polygons size distribution histogram obtained via dynamic light scattering.

Structural Characterization of Polygons by Atomic Force Microscopy (AFM) and DLS To further evaluate the size and shape of the resulting RNA assemblies, structural characterization of each polygon was conducted by AFM. AFM images of the pRNA 3WJ based polygons revealed that the shapes of resulting polygons were similar to their predicted, theoretical 3D models (FIG. 3A). The estimated average dimensions were found to be 13±1.1, 14±1.8 and 17±1.6 nm for triangles, squares and pentagons, respectively. These values do not reflect the true sizes of the RNA polygons due to the AFM tip convolution, but rather demonstrate that the average size of the nanoparticles increases from triangle to pentagon. In addition, the central cavity of each RNA shape is visible, and the size of the cavity gradually increases with the number of polygon vertices. The measured heights for all nanoparticles was found to be 2 nm, in agreement with previously reported heights of nucleic acid double helices (26,53).

Quantification analysis was performed to compare apparent yields between polygons observed on AFM mica surface.

Equal concentrations (1 nM) of the polygons were deposited on a mica surface and correctly folded polygons were manually counted in a 0.5 $\mu m^2$ area, resulting in 48 triangular particles, 33 square particles and 17 pentagon nanoparticles (FIG. 9). The estimated number of triangular nanoparticles adsorbed on the mica was 1.5 times more than that of the square and three times more than that of the pentagon. However, native PAGE revealed that the yields among the three polygons were almost equal. The difference in adsorption amounts between polygons on the mica surface was presumably due to variation in their sizes and 3D conformations, resulting in different dynamic and physical properties.

Hydrodynamic Diameters of the Polygons by DLS was performed to determine the apparent hydrodynamic diameters for each of the polygons.

DLS was performed to determine the apparent hydrodynamic diameters for each of the polygons. The diameters were found to be 9.1, 11.2 and 13.5 nm for triangles, squares and pentagons, respectively (FIG. 3B). The increase in number of 3WJ cores corresponds with the larger observed diameter. The measured diameters agreed with their corresponding 3D models. However, there was a discrepancy between polygon sizes determined by AFM and DLS. This could be attributed to the fundamentally different techniques, as DLS determines the average size distribution profile of nanoparticles in solution assuming that the polygons have globular shapes [refer to manual at http://www.malvern.com], while AFM imaging can produce images larger than the real diameter due to tip size used (54) and the resolution of imaging equipment. Nevertheless, the two techniques demonstrated that the relative size of the nanoparticles increased from triangle to square to pentagon.

Accordingly, native PAGE, AFM and DLS showed the formation of compact molecular 2D assemblies of triangle, square and pentagon based on the pRNA 3WJ ∠AOB.

Consequently, the naturally preserved 60° ∠AOB could be stretched to reach the formation of square and pentagon. The stretching, or tension, that the angle underwent could have had a significant impact on the overall stability of the nanoparticles. Therefore, it was of great interest to evaluate and compare the polygon's stabilities.

Stability Comparison Between Triangle, Square and Pentagon

TGGE Investigation of Polygon Stability

Figure 4A:
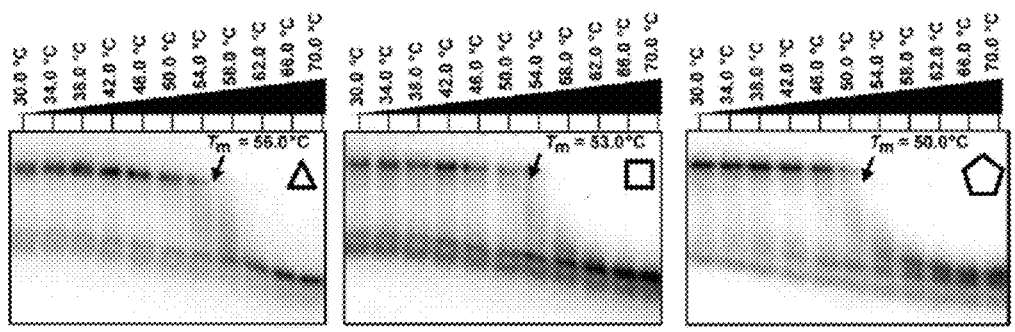
FIGS. 4A and 4B shows a comparison of polygon stabilities. (A) Melting temperatures of triangle, square and pentagon measured by 7% perpendicular TGGE and (B) boiling resistance assay in absence and presence of 8 M urea. Calculated percentage of recovery for polygons after boiling is shown below each gel with error bars calculated from several independent experiments.
Figure 4B:
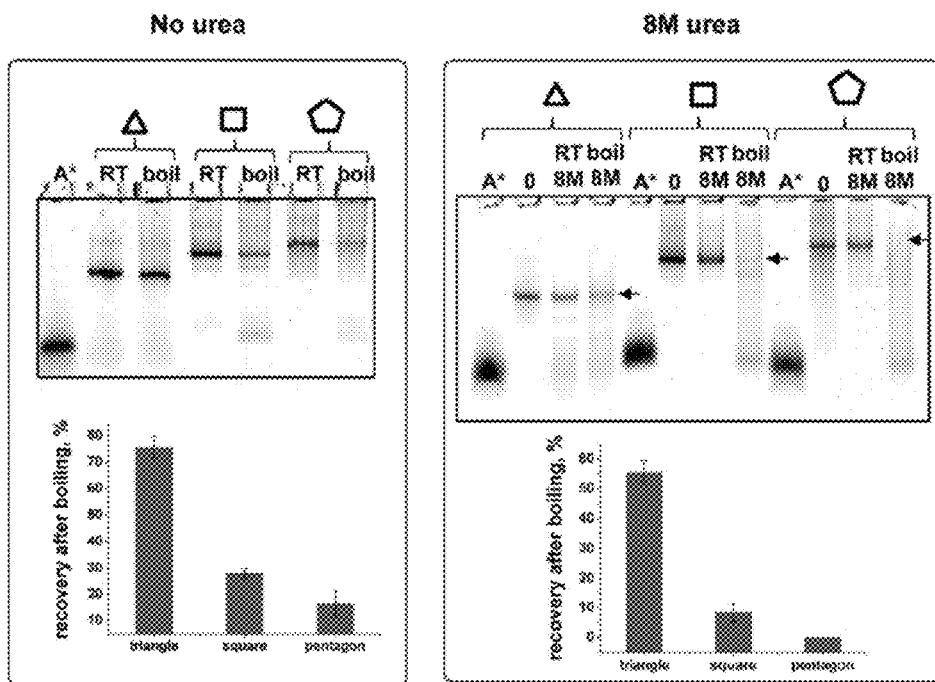

The stabilities of polygons were studied using a perpendicular TGGE (Biometra GmbH). This convenient technique has garnered widespread use for measuring melting temperatures of RNA nanoparticles with multiple strands (5, 7, 14, 26, 28, 55). The preassembled polygons were subjected to 7% native TGGE with a gradient temperature of 30-70° C. perpendicular to electrical current. The following apparent TM values were obtained for the polygons at 100 nM total concentration (Ct) in presence of 0.2 mM MgCl2: triangle TM=56° C., square TM=53° C. and pentagon TM=50° C. (FIG. 4A). The triangular nanoscaffolds were more stable than squares and pentagons, although the number of RNA bp was much higher in the pentagon construct, as compared to the square and triangle. Usually, the stability of nucleic acids with the same base-pair content is directly dependent on metal ion and total nucleic acid concentrations. Since these two criteria were the same, it was assumed that the higher the number of bp in a given RNA structure the higher the stability. Therefore, the most stable shape produced should be the pentagon. However, based on TGGE data the opposite was found. This was likely due to the tension caused by the stretching of the native pRNA 3WJ 60° ∠AOB. The triangular construct angle was preserved (60°), the square and pentagon angles were stretched to the wider conformations of 90° and 108°, respectively. Previously it has been shown that any nucleotide mutations or deletions within the native core structure of the pRNA 3WJ motif would also result in the loss of its thermodynamic stability (10). Interestingly, the measured triangle and square TM values differed by +3° C., as did the square and pentagon. Boiling resistance assay in the presence and absence of 8 M urea further confirmed that the triangle was the most stable nanoparticle (FIG. 4B). The quantification of nanoparticle bands after heating to 100° C. resulted in 75±4% recovery of the triangular assembly, suggesting a TM>100° C. By definition, TM is the measured temperature when half the RNA concentration has melted, i.e. 50% recovery. The percentage of recovery for square was 28±2% and for pentagon was 16±5%, much lower than the value estimated for triangle recovery. The experiment with the presence of 8 M urea in boiling solution showed that the overall trend of stability remained the same, but the percentage of recovery was 55±4% for triangle, 8±3% for square and no pentagon fraction was detected. Overall, the nanoparticle with fewer 3WJ motifs (triangle) resulted in a higher thermostability and resistance in chemical degradation and the change in stability was in large part due to the stretching of the ∠AOB.

Toxicity Assay for CpG-RNA Polygons

Figures 10A, 10B, 10C:
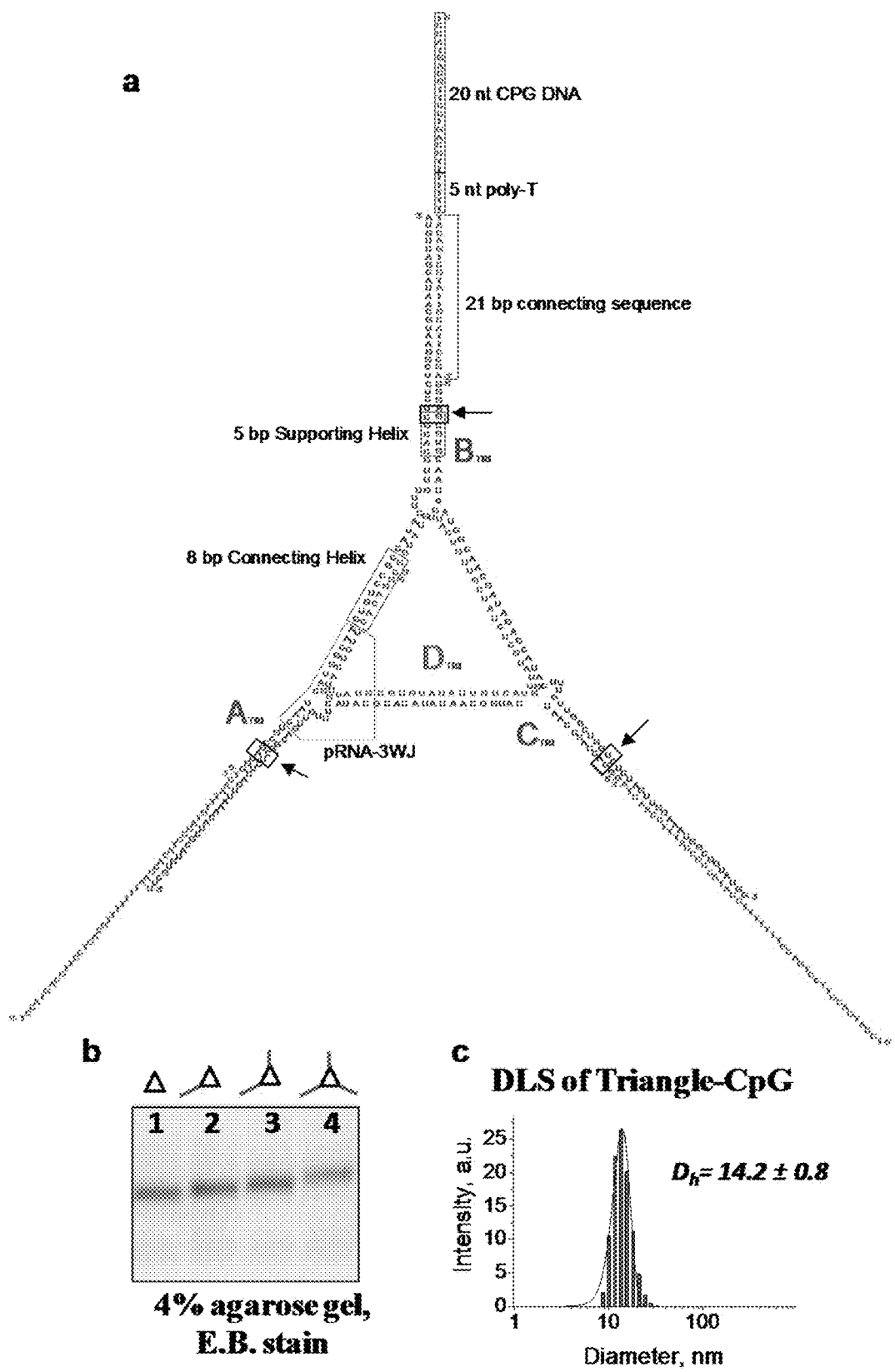
FIGS. 10A and 10B shows secondary structure of triangle-CpG nanoparticle and characterization. (a) 2D structure of RNA triangle harboring 3 CpG adjuvants. Note: Arrows indicate to base pairs that have been deleted in RNA triangle nanoparticle use for animal confocal microscope, and cytotoxicity studies. (b) This is 4% agarose gel assembly of RNA triangle nanoscaffold with CpG adjuvants.
FIG. 10C shows (c) DLS characterization of the triangle-3CpG complex showing apparent hydrodynamic diameter of around 14 nm. The error represents standard deviation from several independent measurements.
Figures 11A, 11B, 11C:
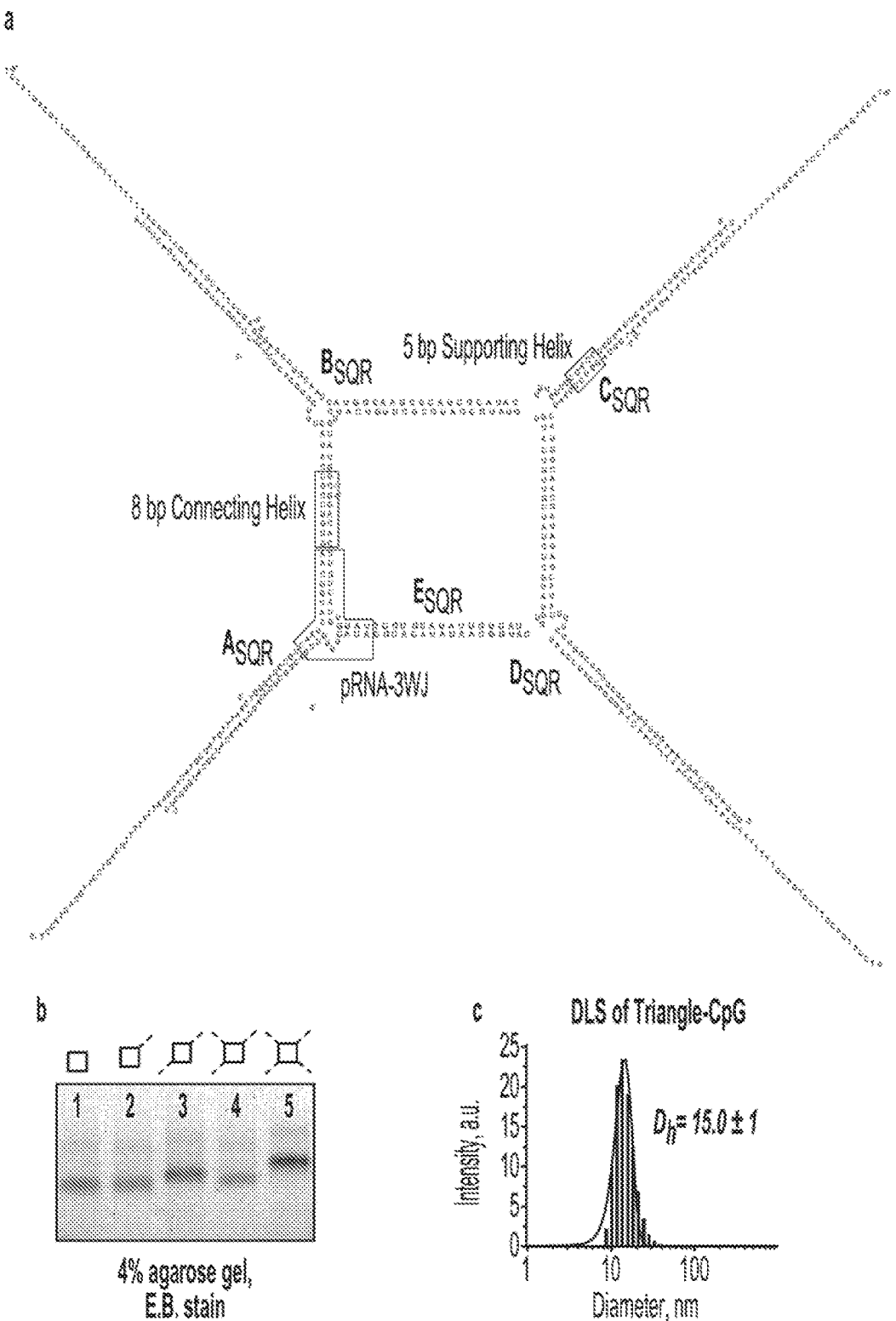
FIG. 11 shows the secondary structure of a square-CpG nanoparticle and characterization. (a) 2D structure of RNA square harboring 4 CpG adjuvants. Figure discloses regions $A_{SQR}$-$E_{SQR}$ as SEQ ID NOS 59 and 60, 61 and 62, 63 and 64, 65, and 66, respectively. (b) This is 4% agarose gel showing assembly of RNA square nanoscaffold with CpG adjuvants. (c) DLS characterization of the square-4CpG complex showing apparent hydrodynamic diameter of around 15 nm. The error represents standard deviation from several independent measurements.
Figures 12A, 12B, 12C:
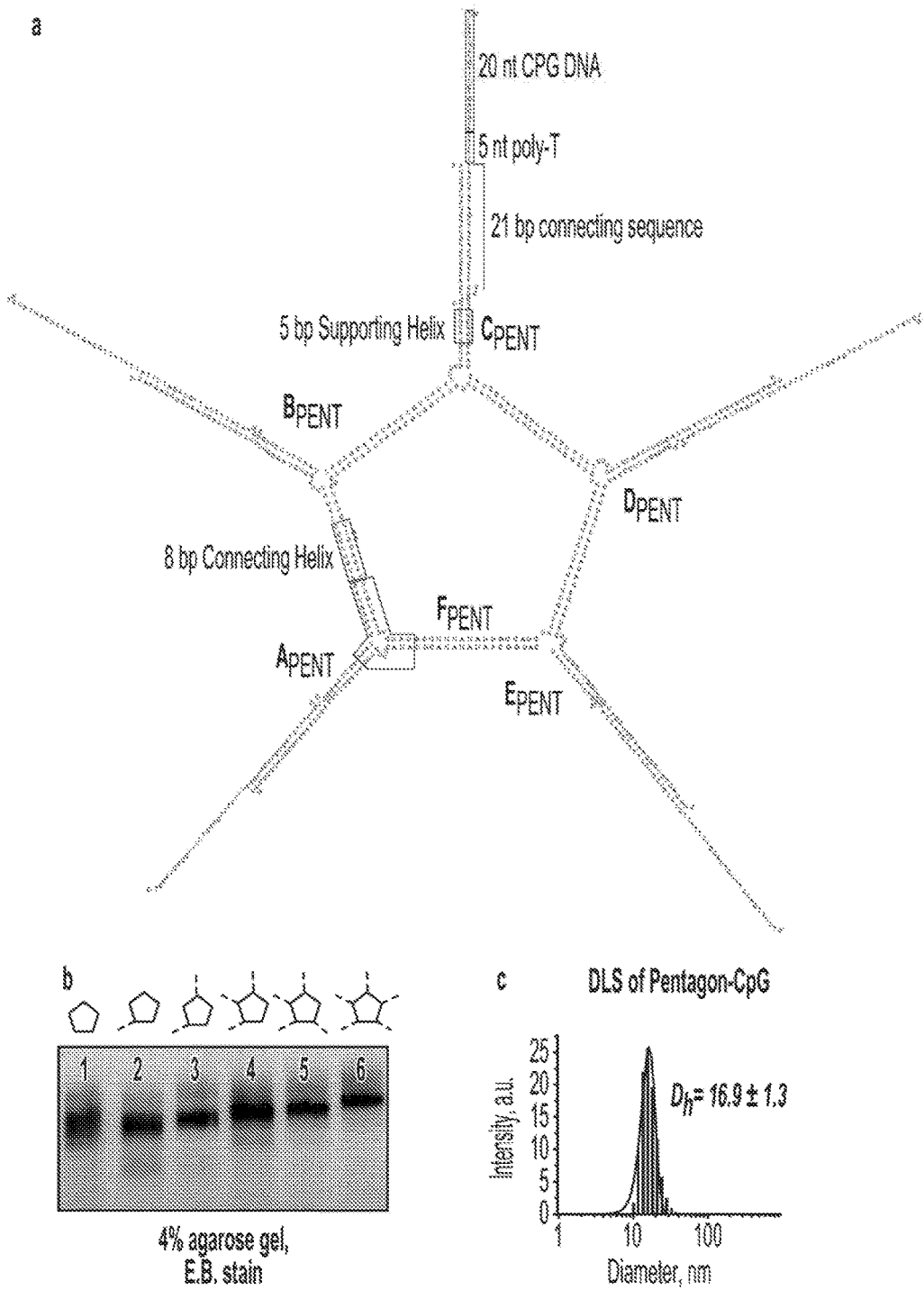
FIG. 12 shows the secondary structure of a pentagon-CpG nanoparticle and characterization. (a) 2D structure of RNA pentagon harboring 5 CpG adjuvants. Figure discloses regions $A_{PENT}$-$F_{PENT}$ as SEQ ID NOS 67 and 68, 69 and 70, 71 and 72, 73 and 74, 75 and 76, and 77, respectively. (b) This is 4% agarose gel showing assembly of RNA pentagon nanoscaffold with CpG adjuvants. (c) DLS characterization of the pentagon-5CpG complex showing apparent hydrodynamic diameter of around 16 nm. The error represents standard deviation from several independent measurements.
Figure 13:
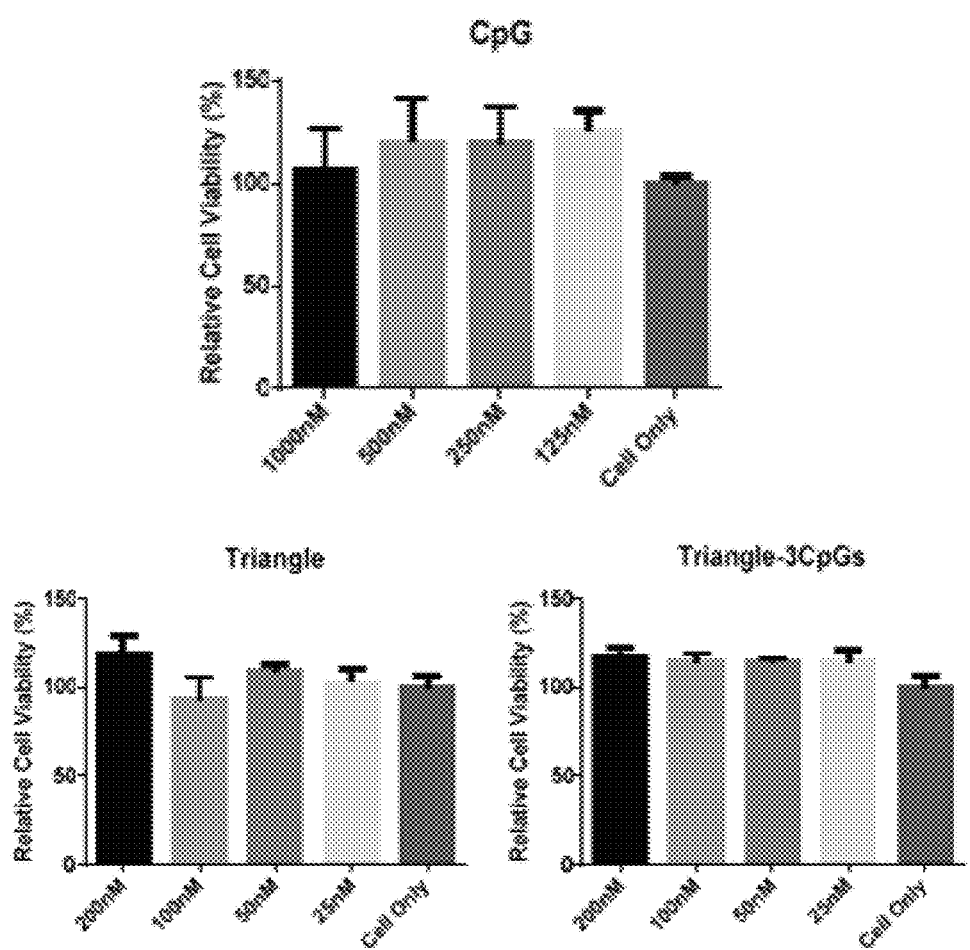
FIG. 13 shows the effect of RNA-CpG adjuvants on RAW264.7 cell viability. The cells were incubated with different concentrations of RNA polygons only, RNA polygons-CpG complexes, and free CpG.

The modulation effect of triangle, square and pentagon harboring immunologic adjuvant CpG oligonucleotide is an immunological adjuvant popularly used as vaccine adjuvant or immunotherapy reagent for disease control and treatment (42). To evaluate whether RNA polygons can enhance the immunomodulation effect, CpG oligonucleotide was incorporated with each RNA polygon using one-pot self-assembly (FIGS. 10-12). The toxicity assay for the resulting complexes revealed no toxicity; moreover the RNA polygon-CpG complexes induced cell proliferation during the incubation period, as compared to the cell only control (FIG. 13).

Measurement of the Release of TNF-Alpha and IL-6 Cytokines

Figures 5A, 5B, 5C, 5D:
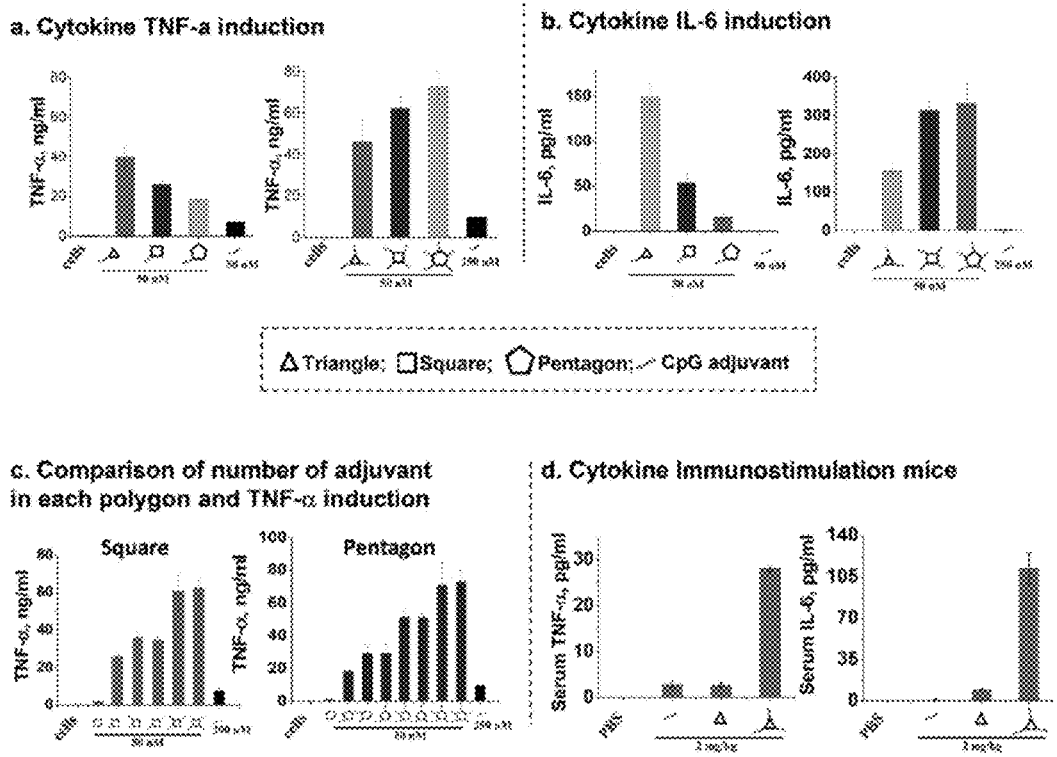
FIGS. 5A-5D shows the effect of cytokine induction in macrophage-like RAW264.7 cells and mice by RNA-CpG polygons. Induction of (A) TNF-α and (B) IL-6 cytokines by 50 nM RNA polygons-CpG. (C) Dependences of TNF-α induction with the number of CpGs per RNA polygon. The error bars represent standard deviation from at least three independent experiments. (D) Immunostimulatory activity by triangle-CpG nanoparticle in animal model. The error bars represent standard deviations of two independent measurements of the cytokine levels from serum aliquots of the tested mouse.

The extracellular immunostimulatory efficacy of RNA polygons was evaluated by measuring the release of cytokines TNF-α and IL-6 after addition to mouse macrophage-like RAW264.7 cells (FIGS. 5A and B), as previously described (56,57). The triangular RNA nanoparticle coupled with only one CpG exhibited the highest level of cytokine induction for both TNF-α and IL-6 compared to square and pentagonal RNA nanoparticles. Increasing the number of CpG per nanoparticle yielded the opposite effect, as pentagonal RNA nanocarriers showed the highest level of the induction of both TNF-α and IL-6 presumably due to the increased local CpG concentration. The results suggest that the cytokine release by CpG coupled to RNA polygons with different shapes remarkably increases the immunostimulatory activity compared to CpG alone (FIG. 5). RNA particles with the size of about 10 nm, such as the triangle, induced the greatest amount of TNF-α and IL-6. In addition, the induction of cytokines was highly dependent on the number of CpG per polygon. With increasing number of CpG per polygon, a stronger immune response is observed (FIG. 5C), demonstrating an advantage of transiting from triangle to pentagon that can carry five CpG oligonucleotides.

Enhancement of Modulation Effect in Animal by Immunological Adjuvant Incorporated into RNA Triangle To examine whether RNA nanoparticles retain their immunostimulatory activity in vivo, nanoparticles were administered to CD-1 mice by injection into the tail vein at 2 mg/kg (CpG oligonucleotide per body weight), following level determination of cytokine TNF-α and IL-6 levels after 3 h post-administration in collected blood serum. FIG. 5D shows that free triangle nanoparticles and free CpGs did not induce any cytokine production, whereas the complex triangle-CpG resulted in elevated levels of both cytokines. The difference in immunostimulatory activity of triangle-CpG was estimated to be 10-fold compared to free CpG in vivo. These data are in agreement with the in vitro stimulation of murine RAW264.7 cells.

Comparison of Cellular Uptake by Different CpG-RNA Polygons

Figure 6A:
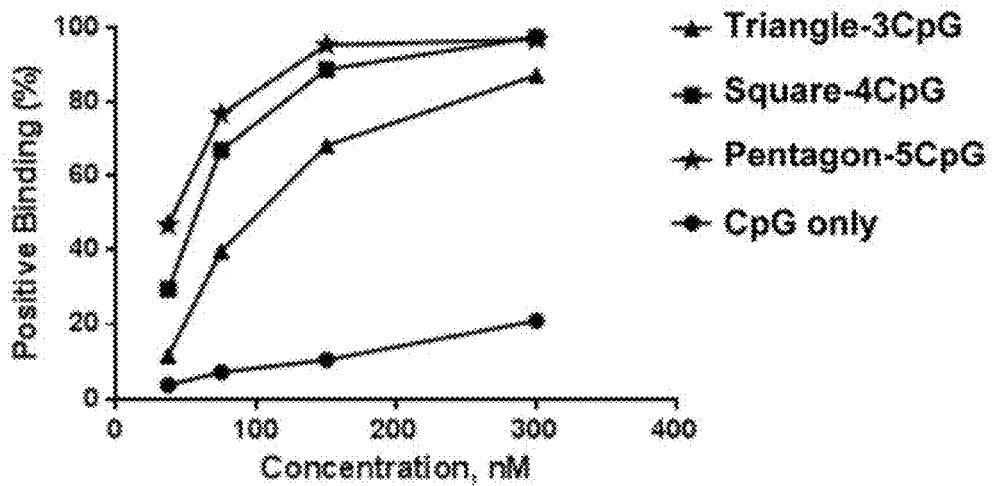
FIGS. 6A and 6B shows a comparison of RNA polygon-CpG complexes binding to the cells. (A) The plot represents the summary of the flow cytometry data showing each RNA nanoparticle-CpG adjuvants binding to the cell in a dose-dependent manner. (B) Confocal images showing the binding comparison of the triangle-CpG and CpG to the RAW624.7 cells by colocalization of nucleus (blue), actin or cytoplasm (green) and Cy-3-labeled CpGs (red) signals.
Figures 14A, 14B, 14C:
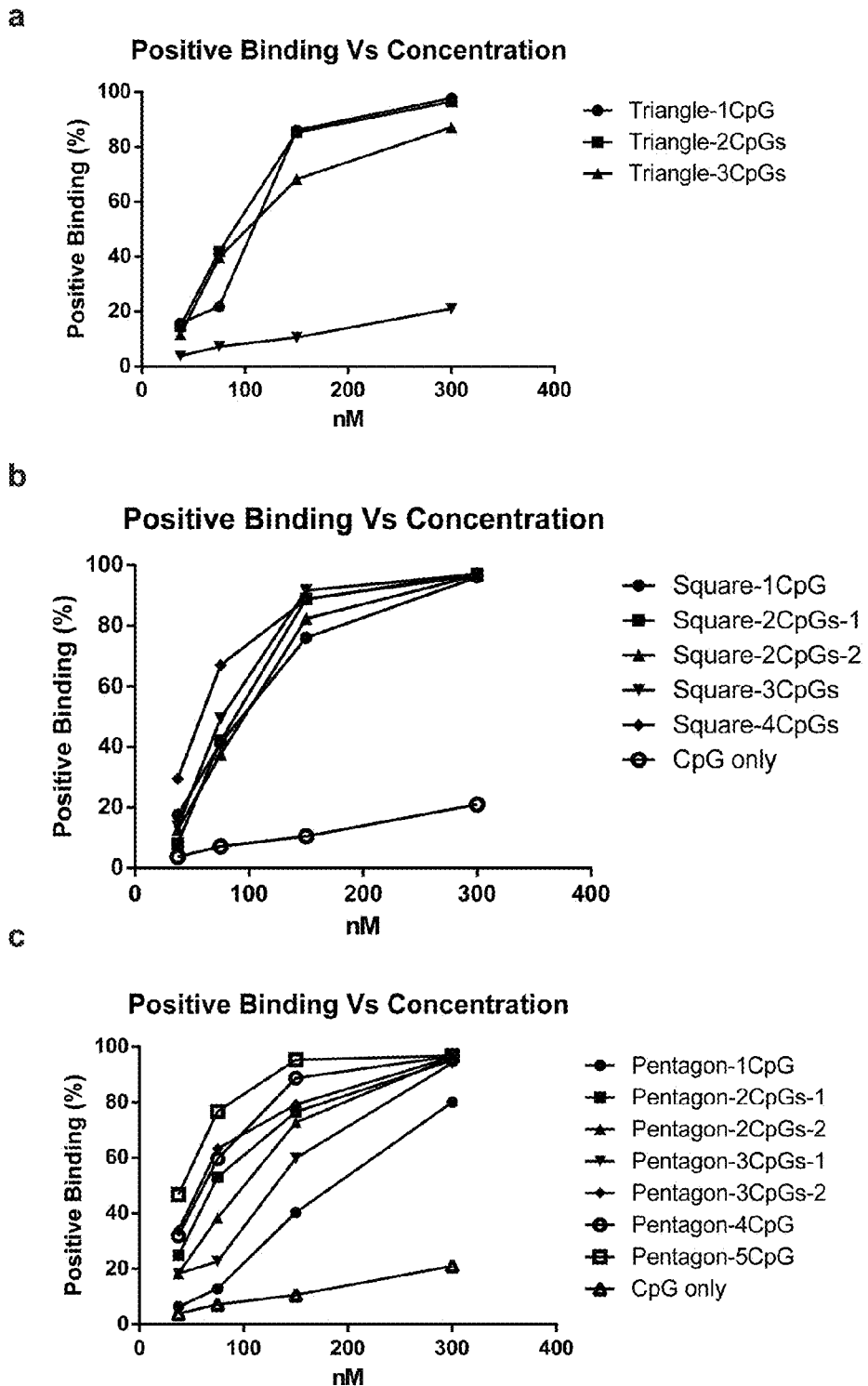
FIG. 14 shows the binding effect of RNA polygons harboring CpG adjuvants to RAW264.7 cells. Concentration dependent binding of (a) triangle-3CpGs, (b) square-4CpGs, and (c) pentagon-5CpGs nanoparticles.
Figure 15:
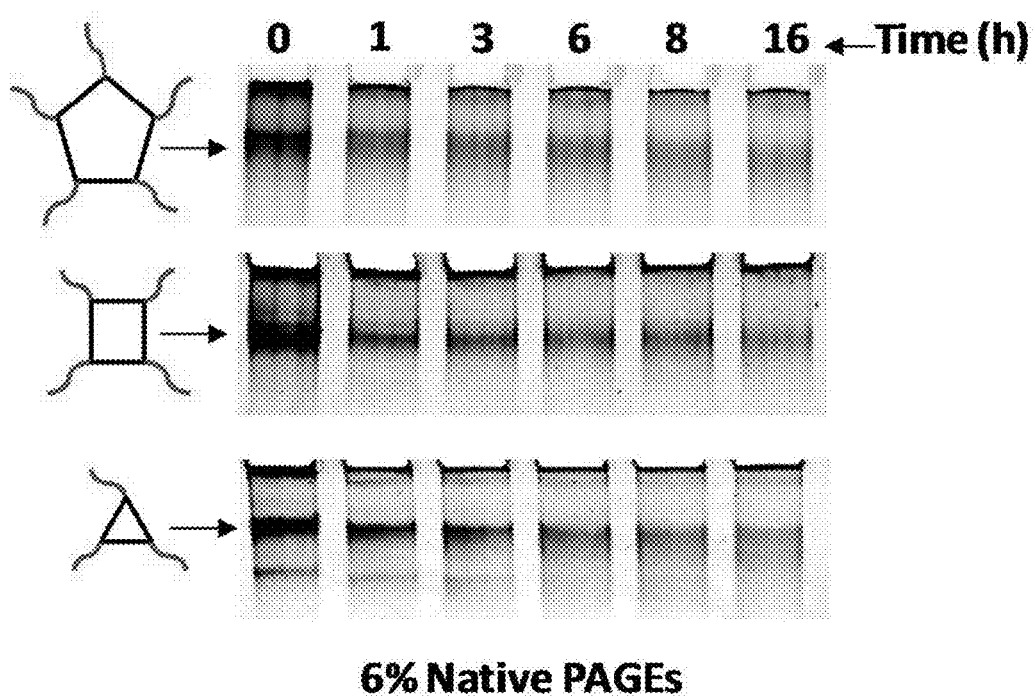
FIG. 15 shows the results of a serum stability assay of RNA polygons coupled with CpGs motifs. Preassembled complexes (1 µM) of RNA triangle, square and pentagon (2′-F modified) harboring DNA CpG were incubated in RPMI-1640 medium containing 10% fetal bovine serum (Sigma). Aliquots (10 µL) were taken at 0 hr, 1 hr, 3 hr, 6 hr, 8 hr and 16 hr time points after incubation at 37° C., followed by analysis using 6% native PAGE gel.
Figure 18:
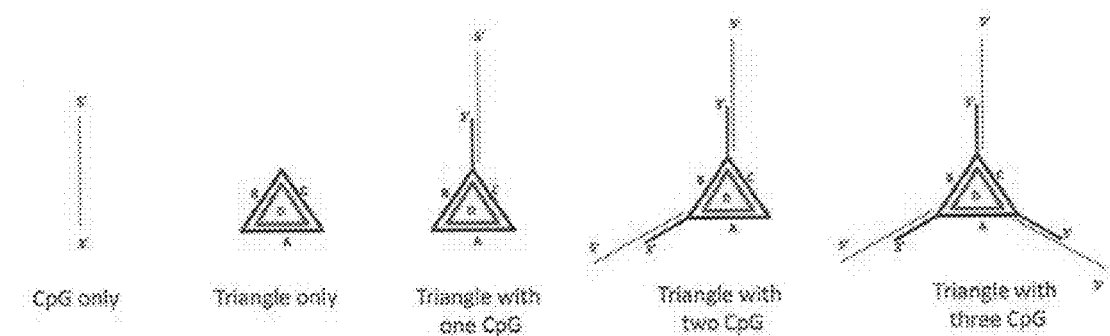
FIG. 18 shows CpG only, a nanostructure RNA triangle only, and a RNA nanostructure triangle with optionally one, two and three CpGs.
Figure 19:
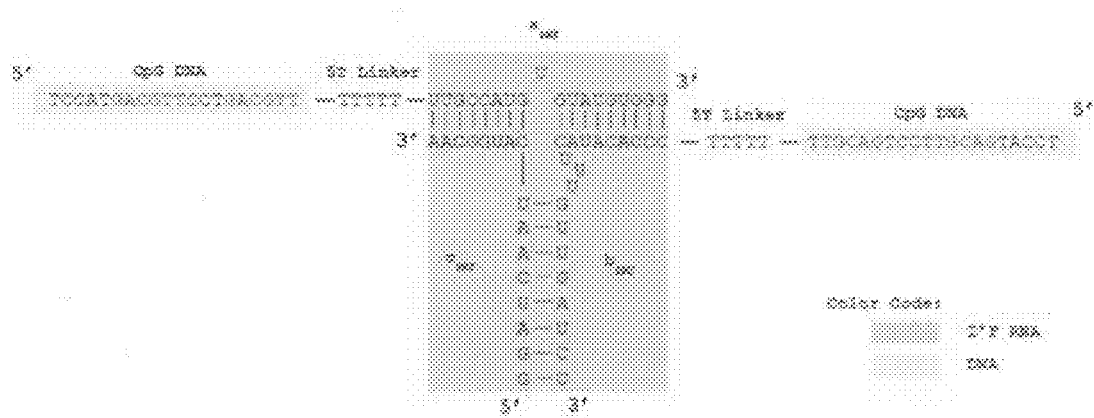
FIG. 19 shows thermodynamically stable RNA three-way junction (3WJ) for efficient delivery of immunostimulatory CpG oligonucleotides, RNA or antigen to immune cells. Figure discloses SEQ ID NOS 86-88, respectively, in order of appearance.
Figure 20:
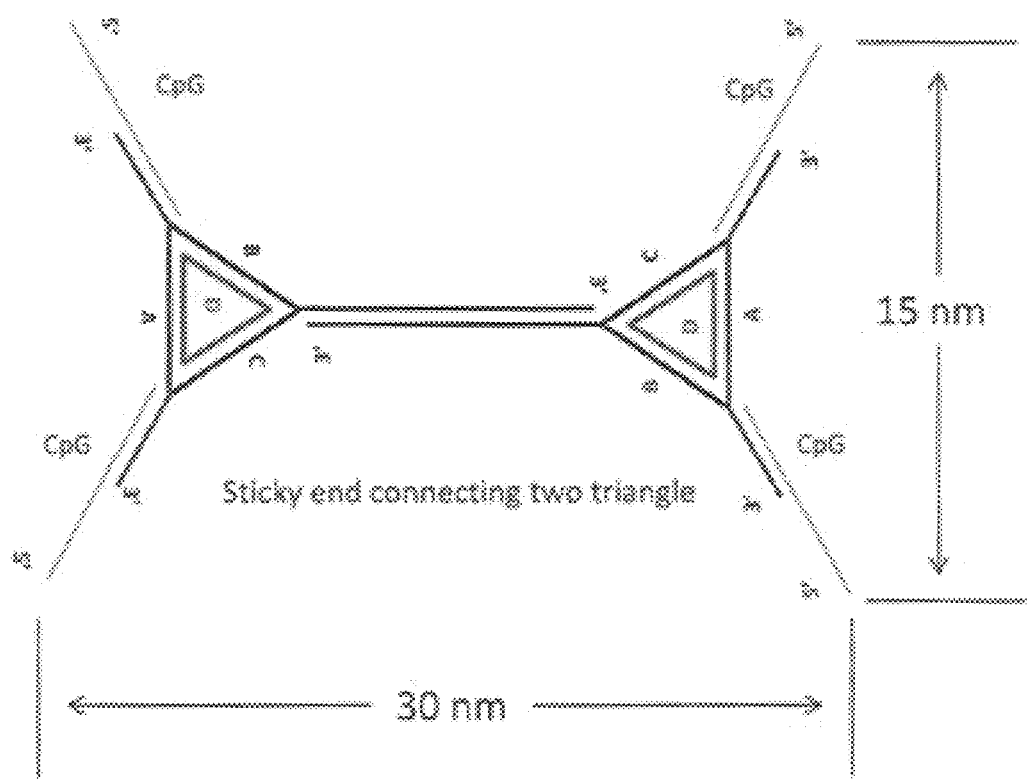
FIG. 20 shows a bowtie-like RNA nanoparticle triangle dimer for delivery of 4CpG. The size of the nanoparticle is twice as triangle (about 20 nm×15 nm).
Figure 21:
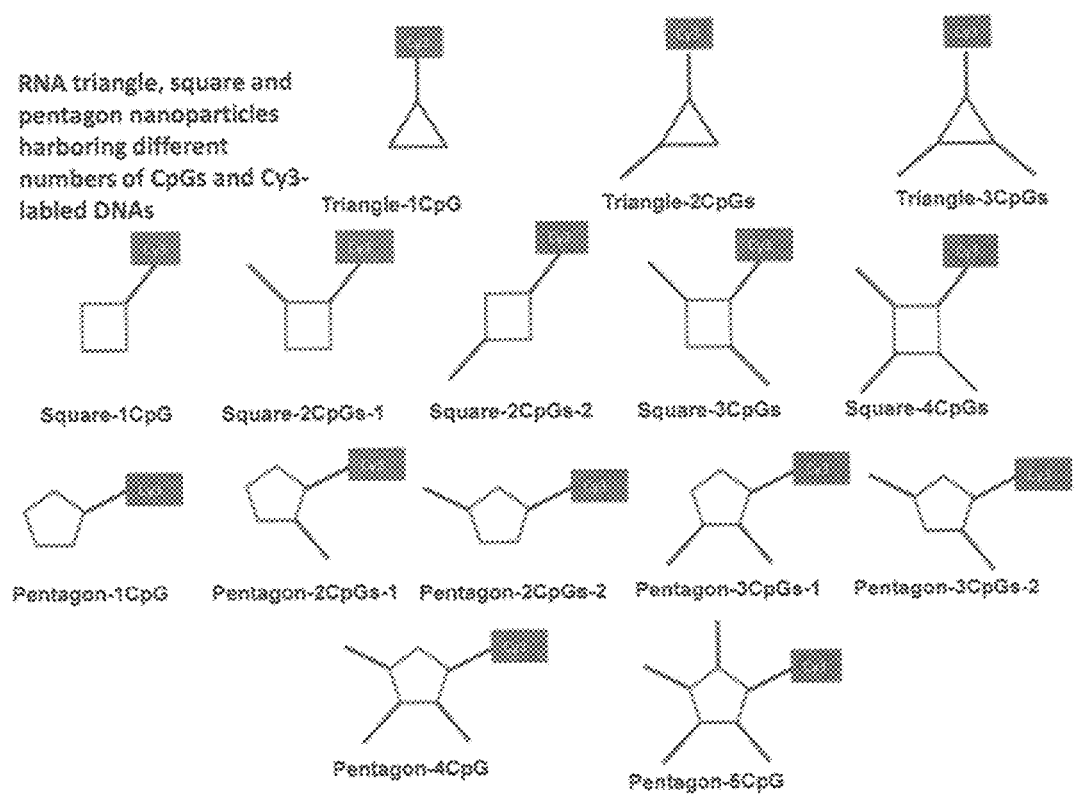
FIG. 21 shows RNA triangle, square and pentagon nanoparticles harboring different numbers of CpGs and Cy3-labeled DNAs
Figure 22:
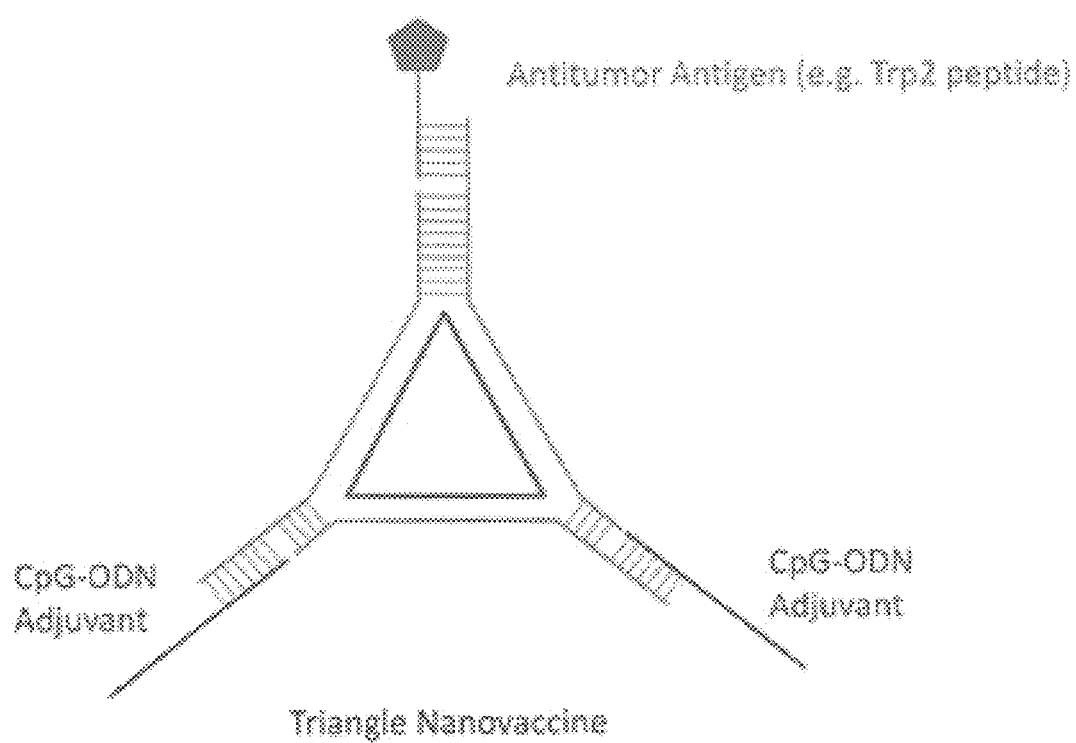
FIG. 22 shows an RNA nanoparticle for anticancer vaccine or immunotherapy
Figure 23:
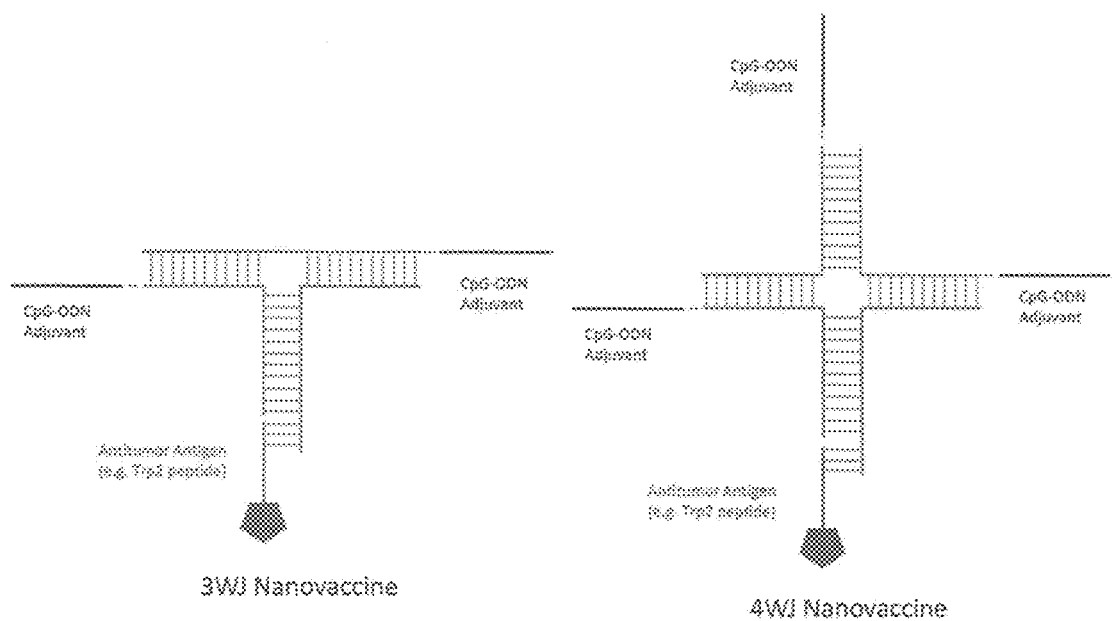
FIG. 23 shows a 3WJ nanovaccine containing CpG-ODN adjuvant and antitumor antigen and a 4WJ nanovaccine containing CpG-ODN adjuvant and antitumor antigen
Figure 24:
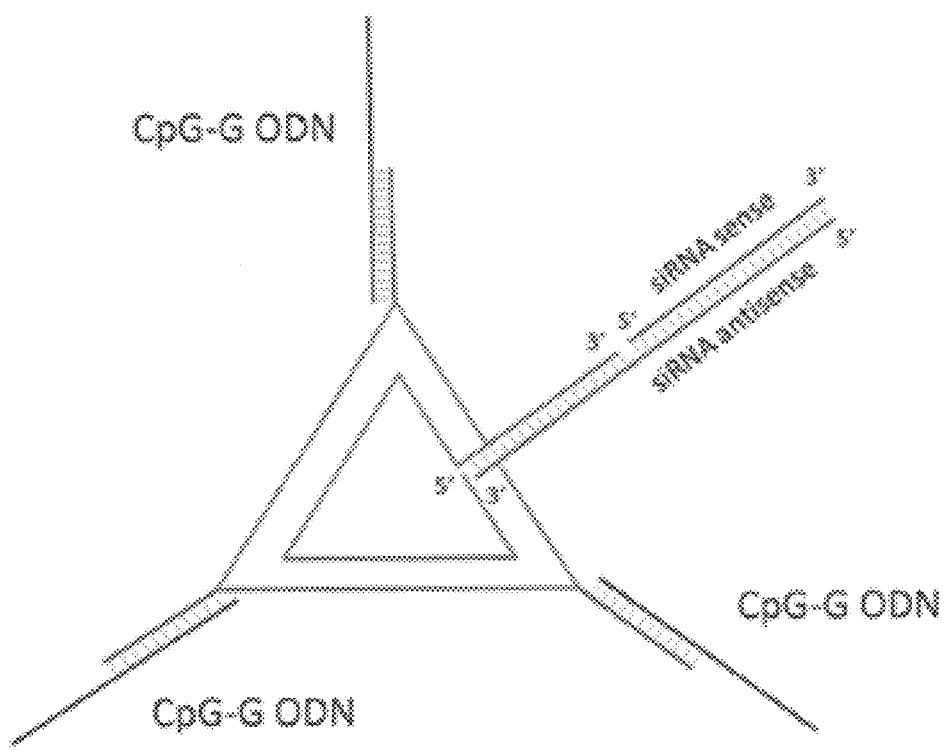
FIG. 24 shows a Triangle RNA nanostructure harboring CpG-G ODN and siRNA.
Figure 25:
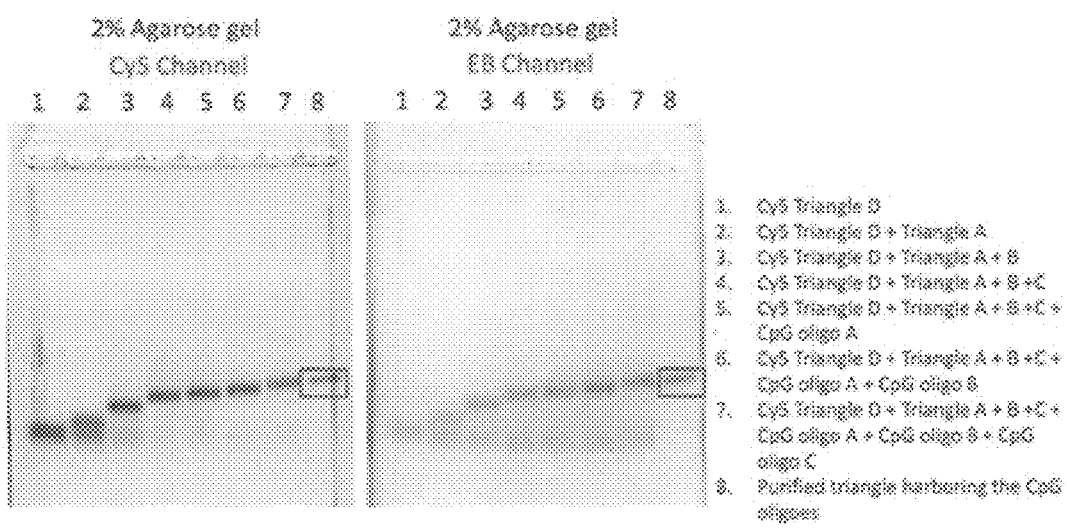
FIG. 25 shows the assemblies of RNA nanostructure triangles harboring CpG oligonucleotides.
Figure 26:
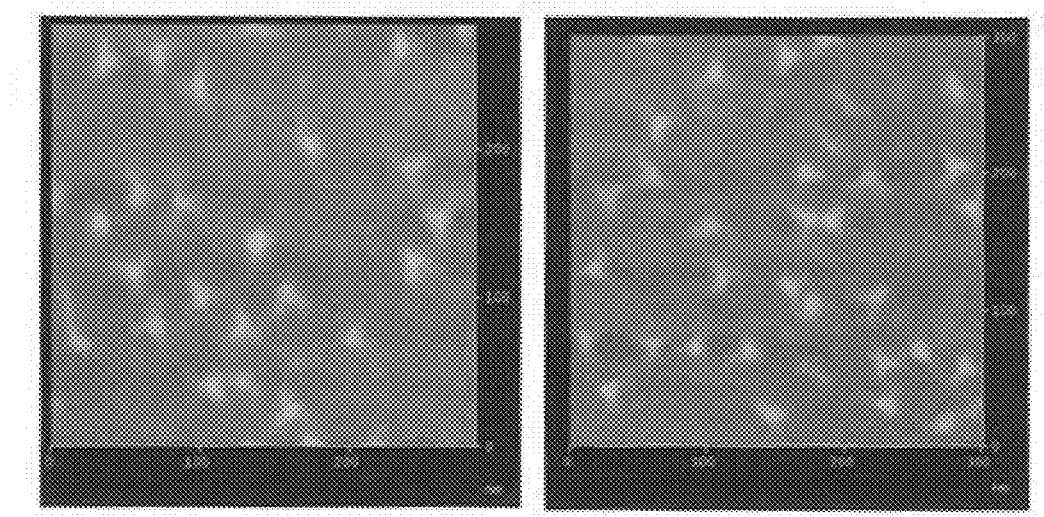
FIG. 26 shows AFM images of RNA nanostructure triangles harboring three CpGs.
Figure 27:
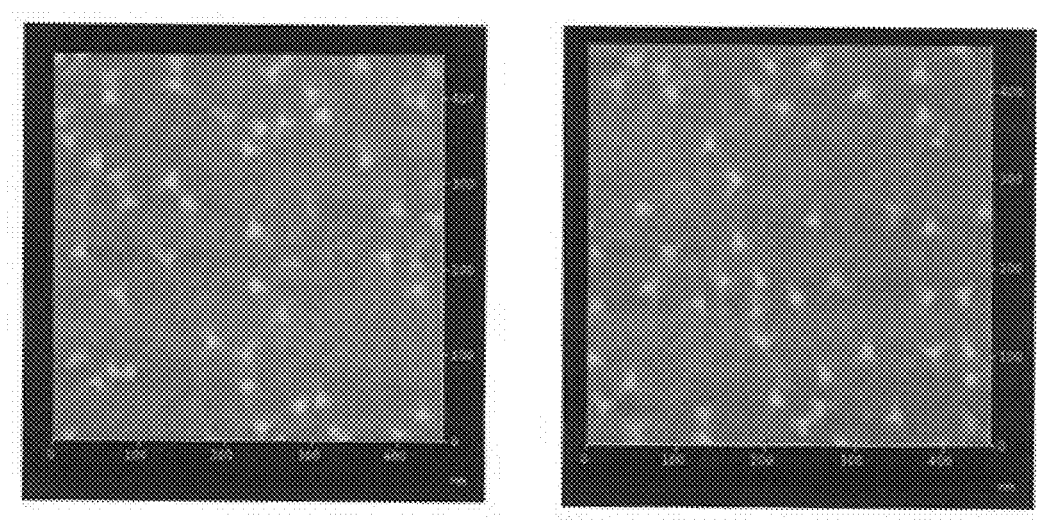
FIG. 27 shows AFM images of RNA nanostructure triangles harboring three CpGs.
Figure 28:
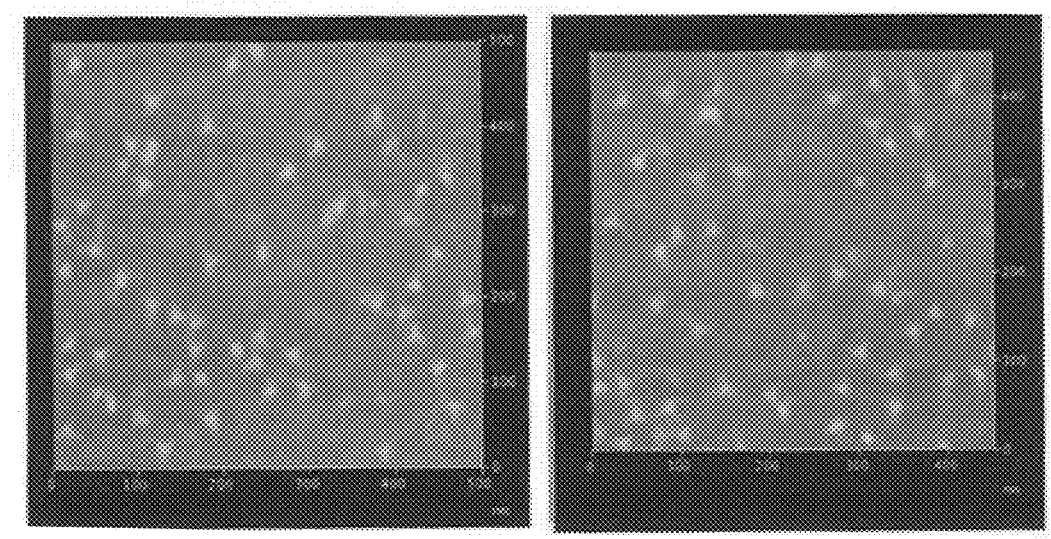
FIG. 28 shows AFM images of RNA nanostructure triangles harboring three CpGs.
Figure 29:
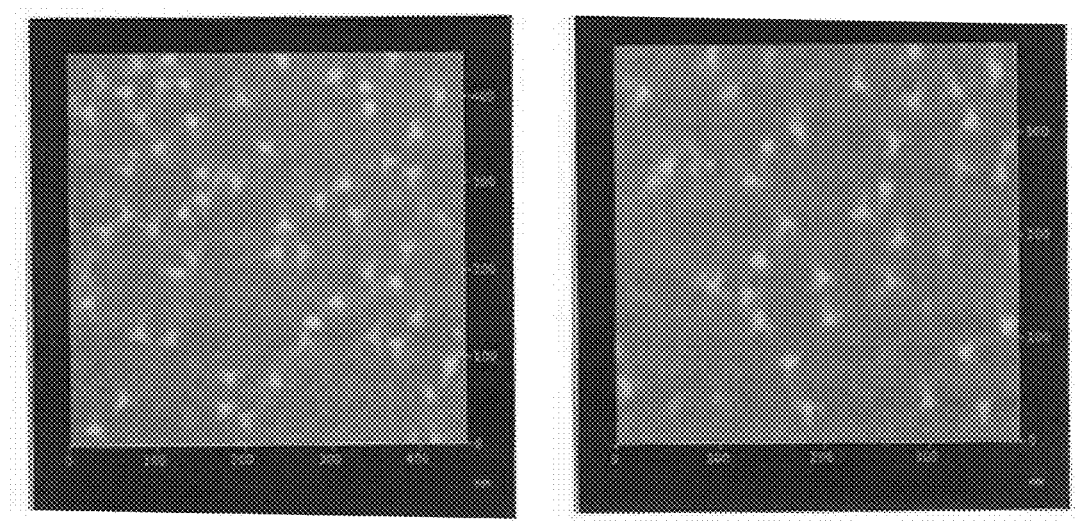
FIG. 29 shows AFM images of RNA nanostructure triangles harboring three CpGs.
Figure 32:
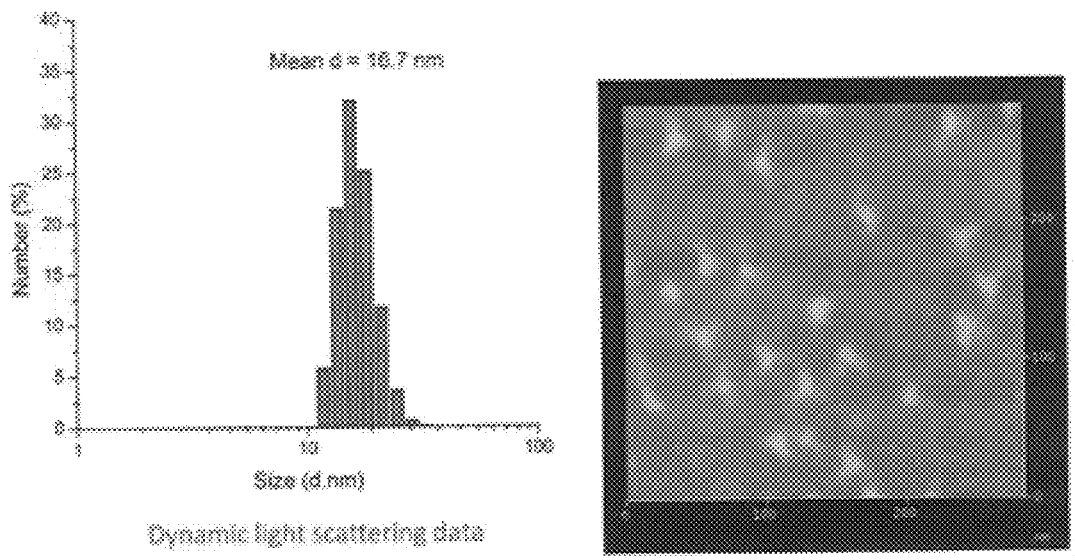
FIG. 32 shows Dynamic Light Scattering (DLS) data showing the mean diameter of triangle-3CpGs of 16.7 nM and its agreement with AFM imaging data.
Figure 33:
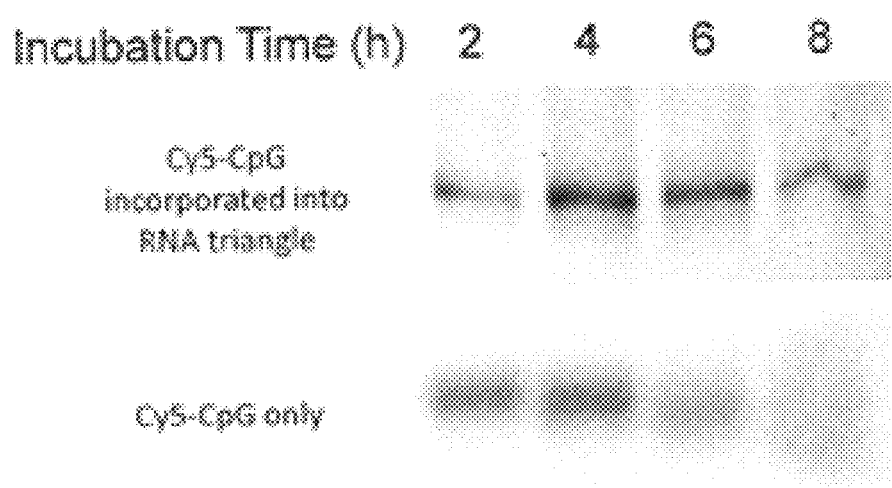
FIG. 33 shows how the RNA nanostructure triangle protects CpG oligonucleotides from degradation in serum over time.
Figure 34:
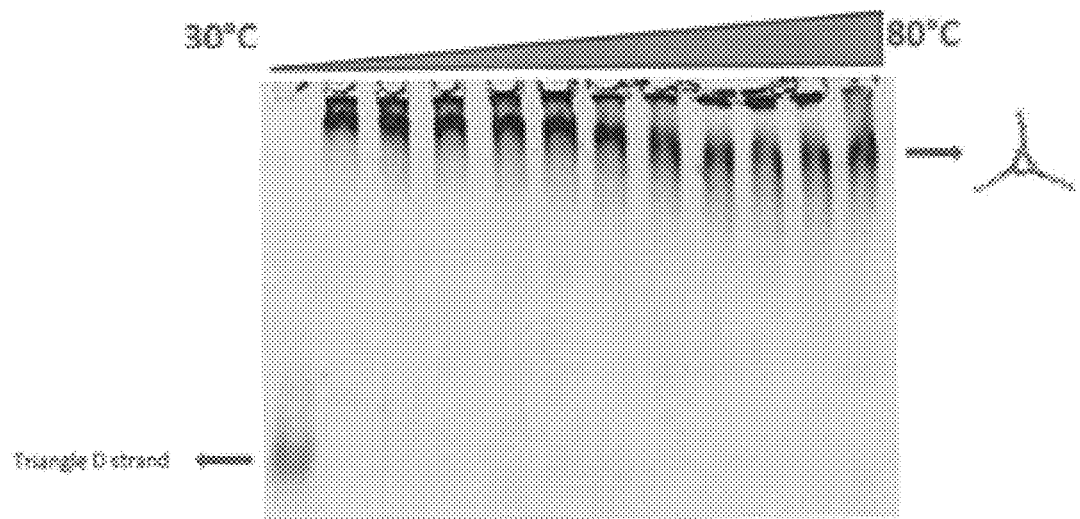
FIG. 34 shows a Temperature Gradient Gel Electrophoresis (TGGE) of RNA nanostructure triangle harboring CpG oligonucleotides over increasing temperatures from 30° C. to 80° C.
Figure 35:
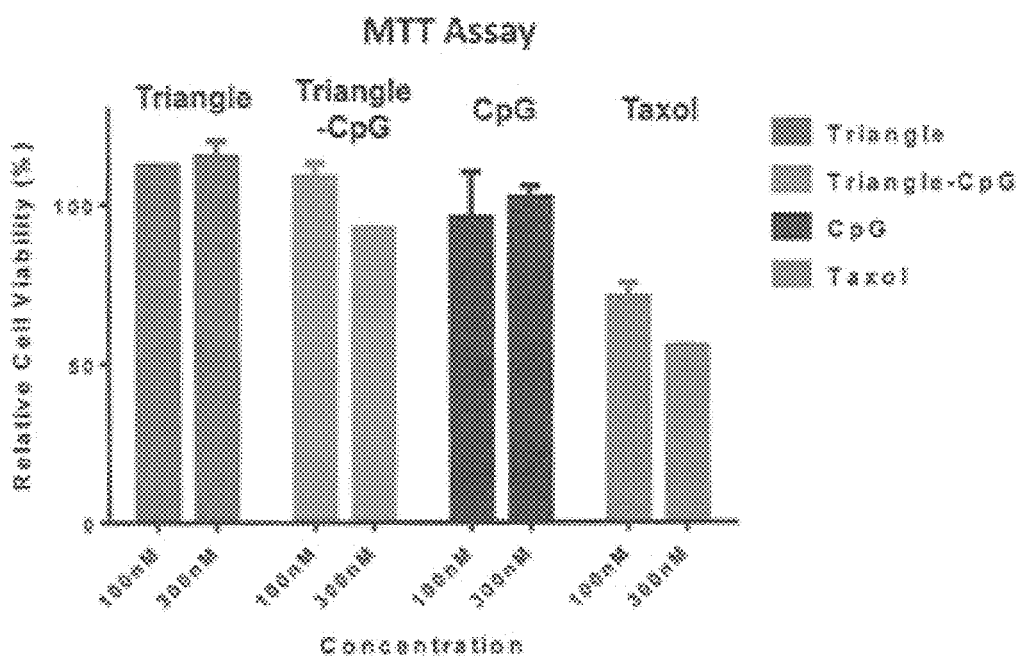
FIG. 35 shows a chart of relative cell viability vs. concentration from investigation of toxicity of RNA Triangle-CpG.
Figure 36:
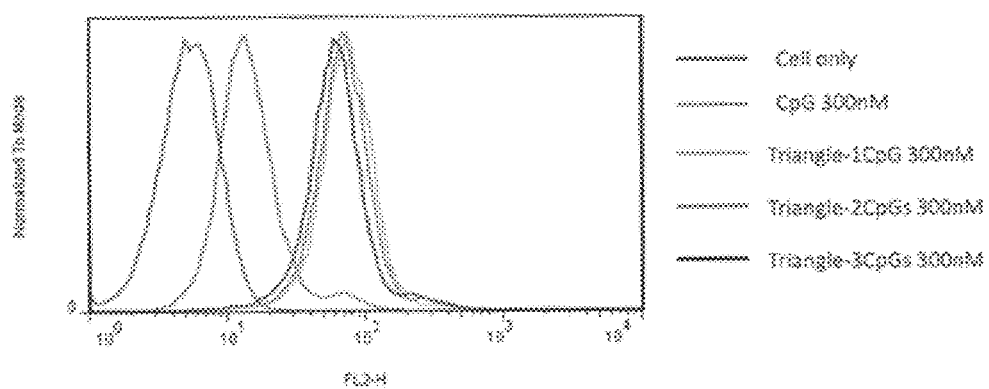
FIG. 36 shows a flowcytometry study of 300 nM triangle RNA harboring different numbers of CpGs binding to raw 264.7 cells. Positive binding: Triangle-1CpG 300 nM=Triangle-2CpGs 300 nM=Triangle-3Cpgs 300 nM>CpG 300 nM.
Figure 37:
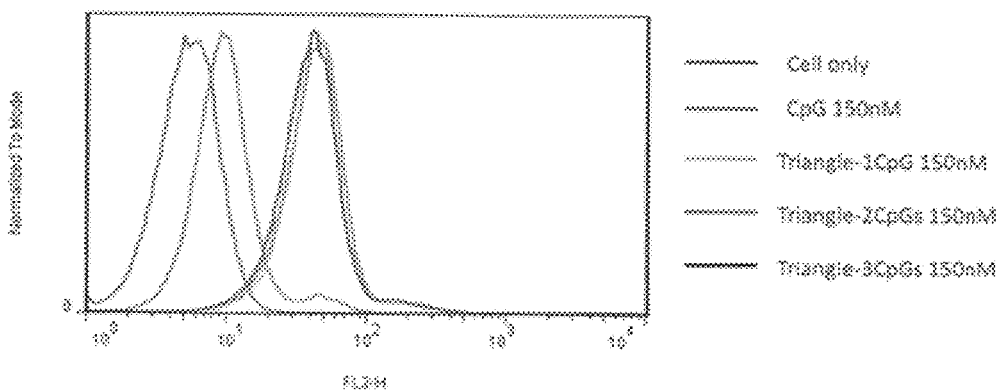
FIG. 37 shows a flowcytometry study of 1500 nM triangle RNA harboring different numbers of CpGs binding to raw 264.7 cells. Positive binding: Triangle-1CpG 150 nM=Triangle 2CpGs 15-nM=Triangle-3CpGs 150 nM>CpG 150 nM.
Figure 38:
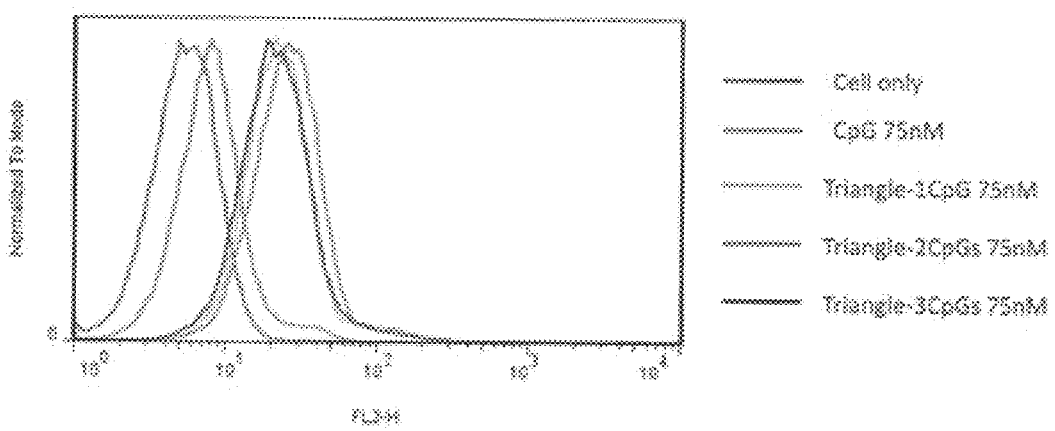
FIG. 38 shows a flowcytometry study of 75 nM triangle RNA harboring different numbers of CpGs binding to raw 264.7 cells. Positive binding: Triangle-1CpG 75 nM=Triangle-2CpGs 75 nM=Triangle-3CpGs 75 nM>CpG 75 nM.
Figure 39:
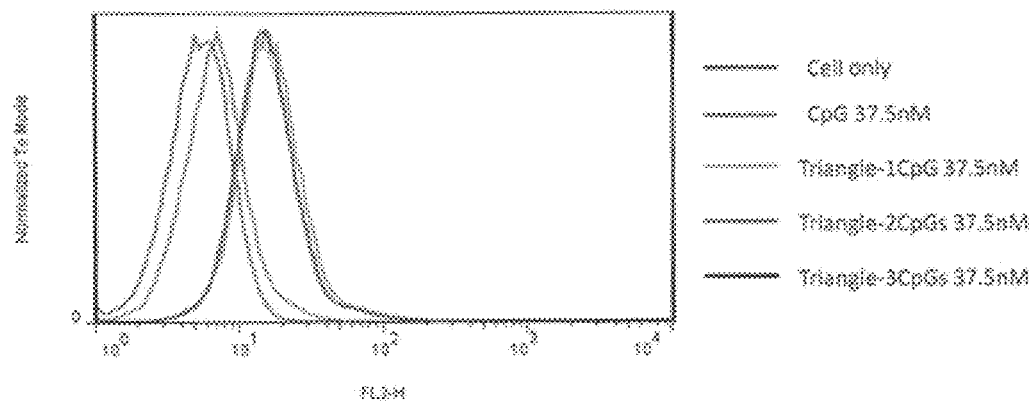
FIG. 39 shows a flowcytometry study of 37.5 nM triangle RNA harboring different numbers of CpGs binding to raw 264.7 cells. Positive binding: Triangle-1CpG 37.5 nM=Triangle 2CpGs 37.5 nM=Triangle-3CpGs 37.5 nM>CpG 37.5 nM.
Figure 40:
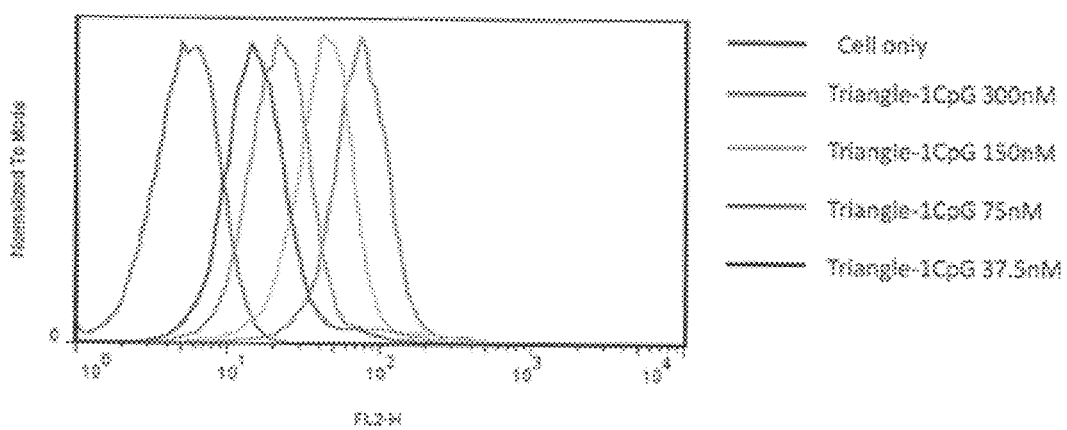
FIG. 40 shows a flowcytometry studying different concentration of triangle-1CpG binding to raw 264.7 cells. Positive binding: Triangle-1CpG 300 nM>Triangle-1CpG 150 nM>Triangle-1CpG 75 nM>Triangle-1CpG 37.5 nM.
Figure 41:
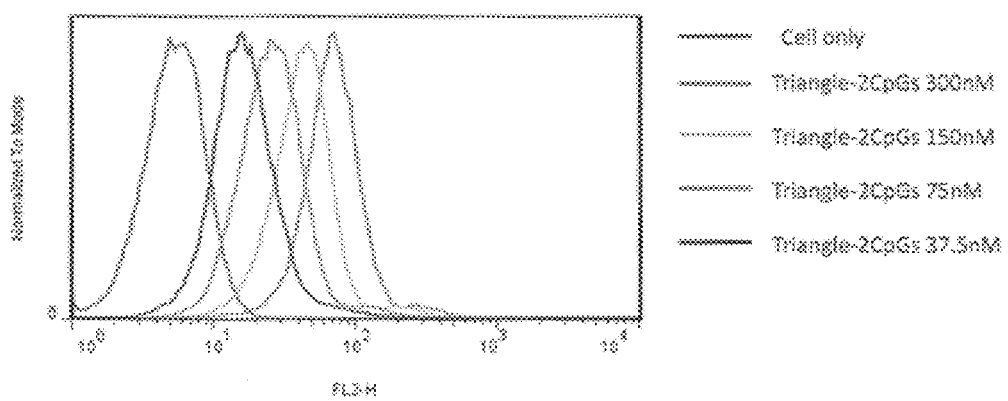
FIG. 41 shows a flowcytometry studying different concentration of triangle-2CpGs binding to raw 264.7 cells. Positive binding: Triangle-2CpG 300 nM>Triangle-2CpG 150 nM>Triangle-2CpG 75 nM>Triangle-2CpG 37.5 nM.
Figure 42:
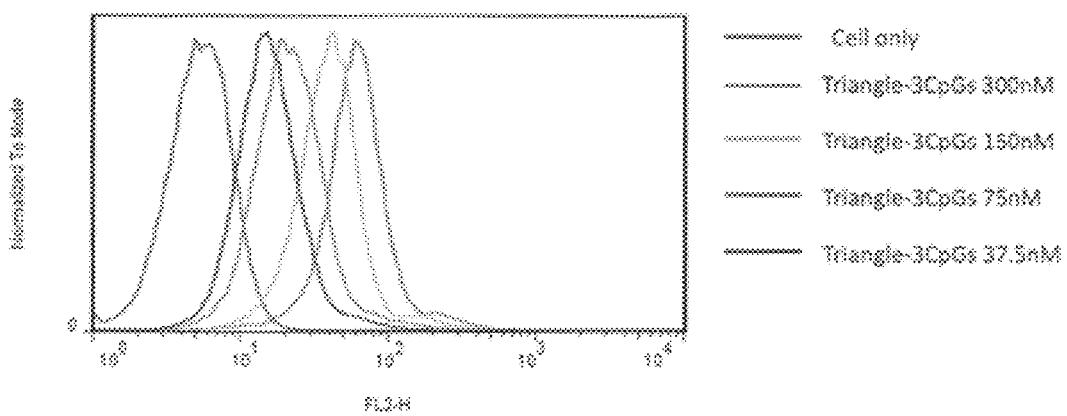
FIG. 42 shows a flowcytometry studying different concentration of triangle-3CpGs binding to raw 264.7 cells. Positive binding: Triangle-3CpG 300 nM>Triangle-3CpG 150 nM>Triangle-3CpG 75 nM>Triangle-3CpG 37.5 nM.
Figure 43:
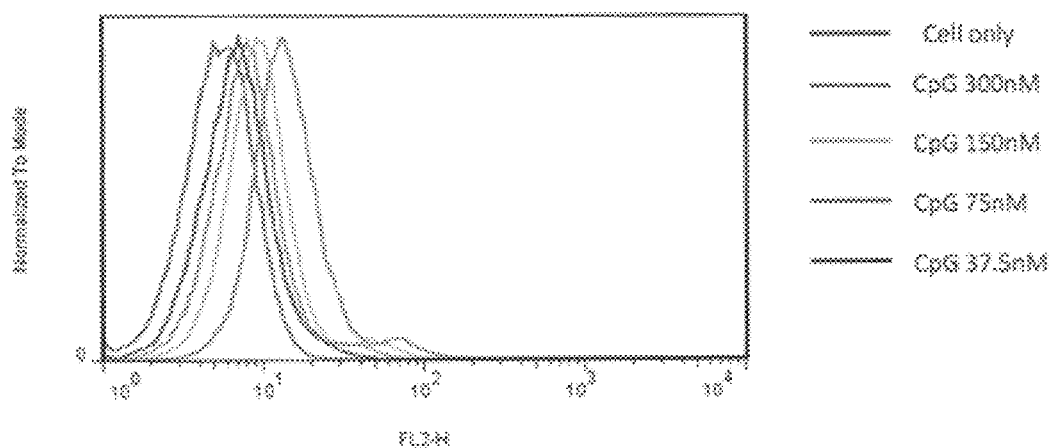
FIG. 43 shows a flowcytometry studying different concentration of CpG binding to raw 264.7 cells. Positive binding: CpG 300 nM>CpG 150 nM>CpG 75 nM>CpG 37.5 nM.
Figure 44:
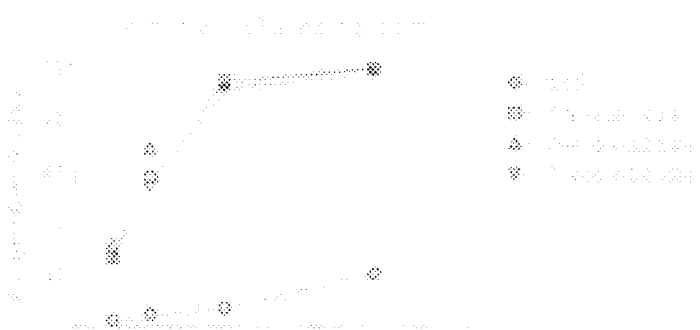
FIG. 44 shows a table showing differing concentrations of CpG, Triangle-1CpG, Triangle-2CpGs, and Triangle-3CpGs and their respective levels of binding. Triangle-1CpG, Triangle-2CpGs and Triangle-3CpGs all have much stronger binding than CpG only. Triangle should enhance the delivery of CpG, which is also in agreement with the previous cytokine data (stronger binding correlates to stronger cytokine induction).
Figure 45:
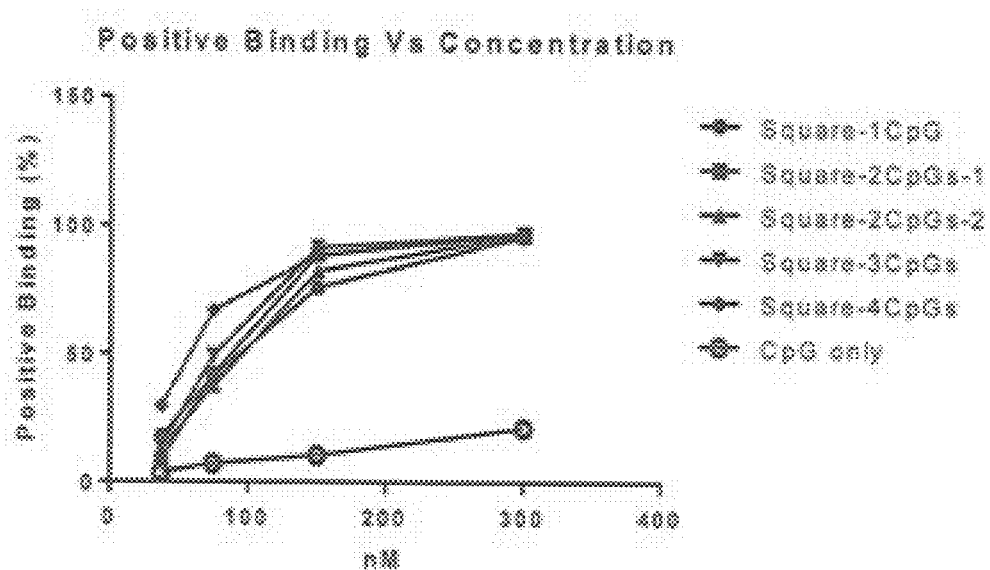
FIG. 45 shows a flowcytometry comparing square RNA harboring different number of CpGs binding to raw 264.7 cells. Positive binding: Square-1CpG=Square-2CpGs-1=Square-2CpGs-2=Square-3CpGs=Square-4CpGs>CpG Only
Figure 46:
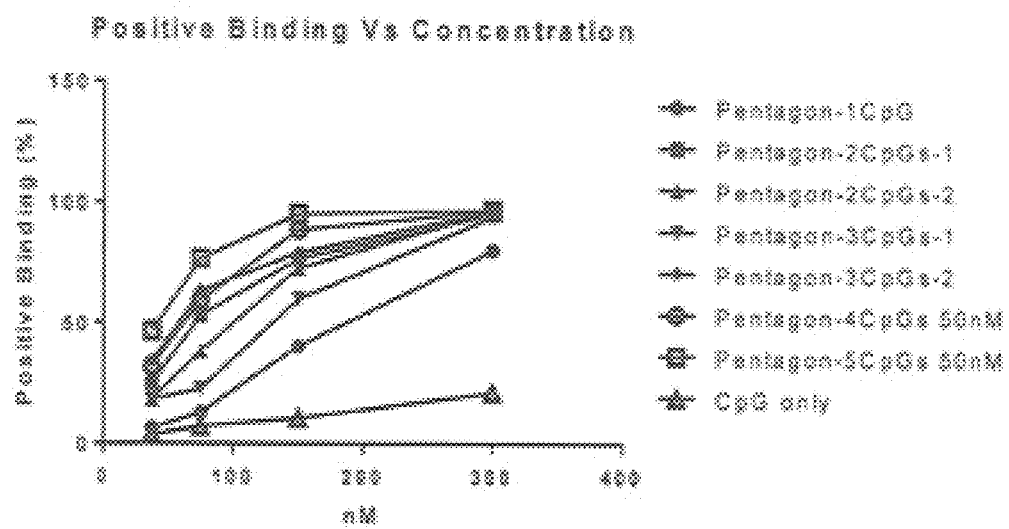
FIG. 46 shows a flowcytometry comparing pentagon RNA harboring different number of CpGs binding to raw 264.7 cells. Positive binding: Pentagon-5CpG=Pentagon-4CpG=Pentagon-3CpGs-1=Pentagon-3CpGs-2=Pentagon-2CpGs-1=Pentagon-2CpGs-2>Pentagon-1CpG>CpG only.
Figure 47:
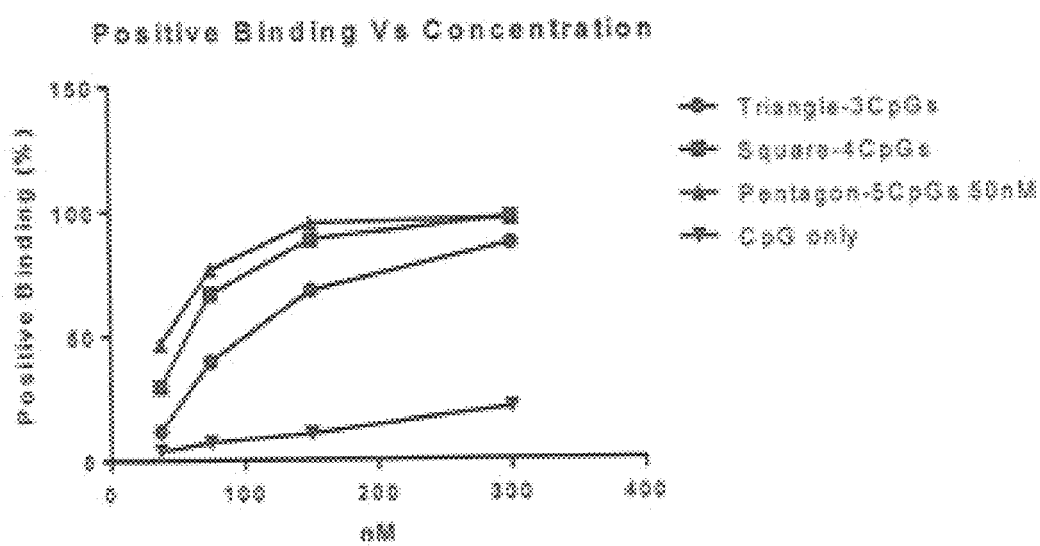
FIG. 47 shows a flowcytometry comparing triangle-3CpG, square-4CpG, and pentagon-5CpG RNA nanostructures binding to raw 264.7 cells. Positive binding: Pentagon-5CpG=Square-4CpG=Triangle-3CpG>CpG only.
Figure 48:
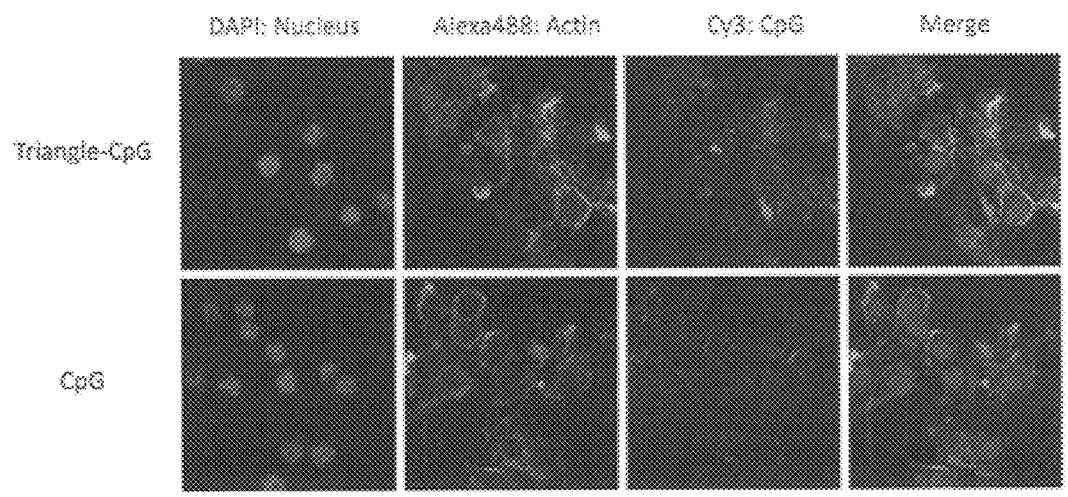
FIG. 48 shows confocal imaging of triangle-CpG interacting with raw cells.
Figure 49:
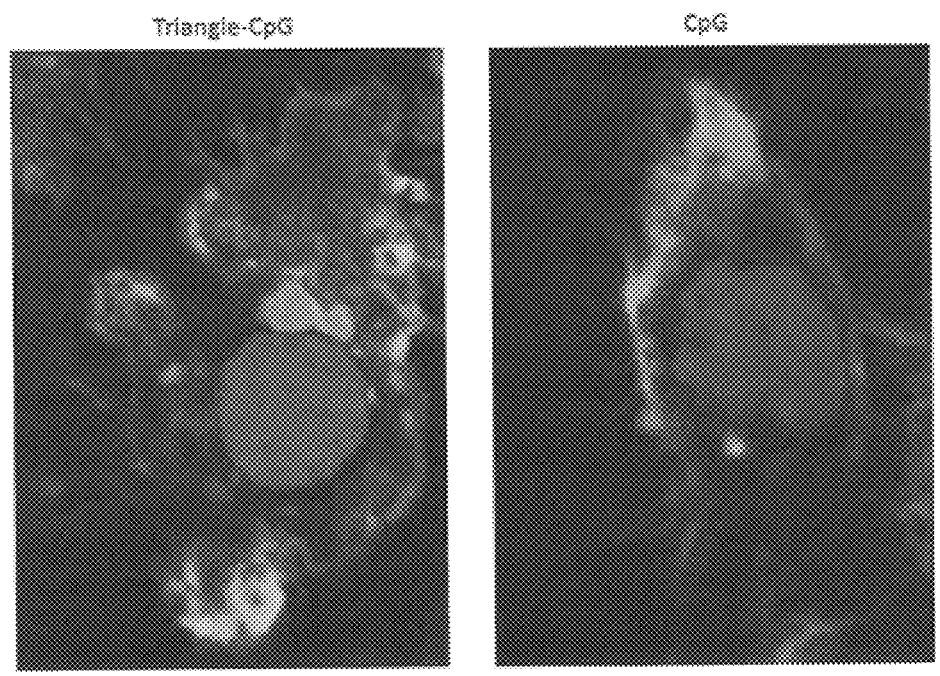
FIG. 49 shows confocal imaging of triangle-CpG interacting with raw cells.
Figure 50:
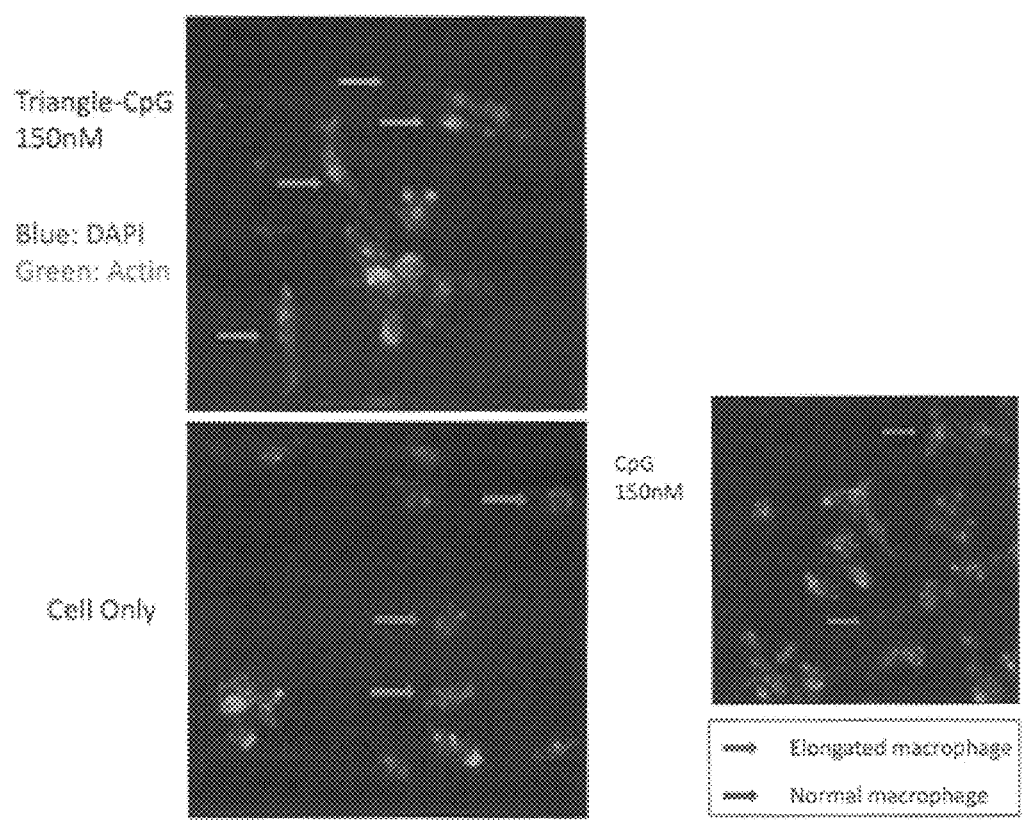
FIG. 50 shows fluorescent imaging of morphology changes of triangle-CpG induced raw cells. Upon treatment with triangle-CpG or CpG, the cell morphology changed from a round form to an elongated form with more spreading and forming pseudopodia.
Figure 51:
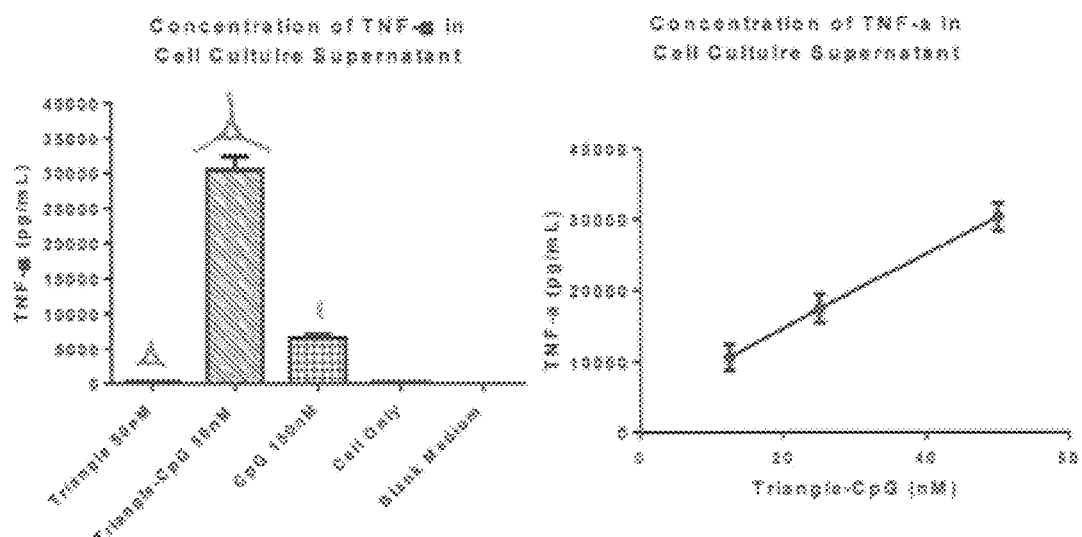
FIG. 51 shows results of TNF-alpha cytokine ELISA assay for 1) Triangle-CpG compared to Triangle RNA, CpG, cell only, and blank medium and 2) increasing concentration of Triangle-CpG.
Figure 52:
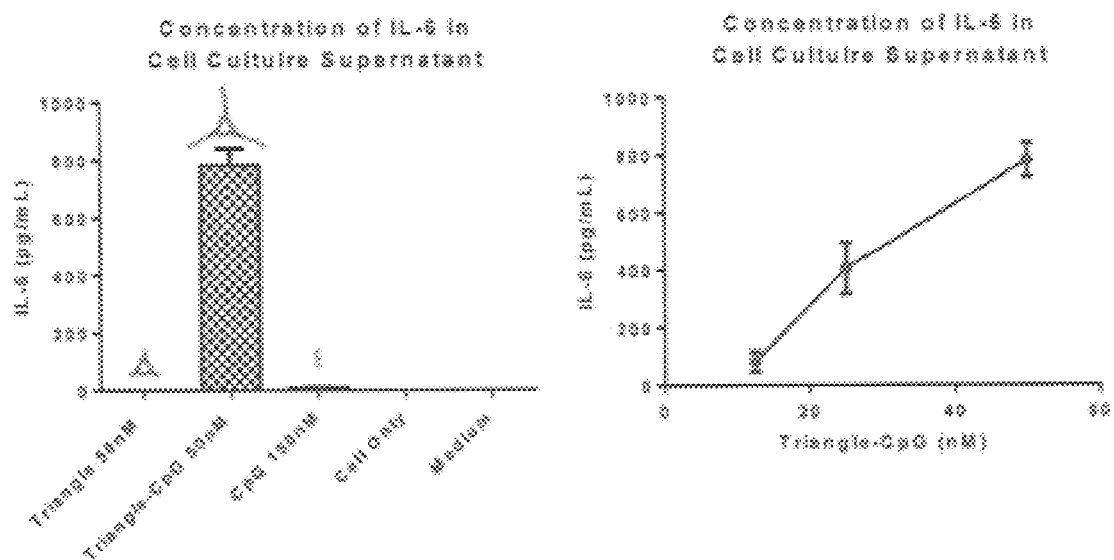
FIG. 52 shows IL-6 cytokine ELISA assay for 1) Triangle-CpG compared to Triangle RNA, CpG, cell only, and blank medium and 2) increasing concentration of Triangle-CpG.
Figure 53:
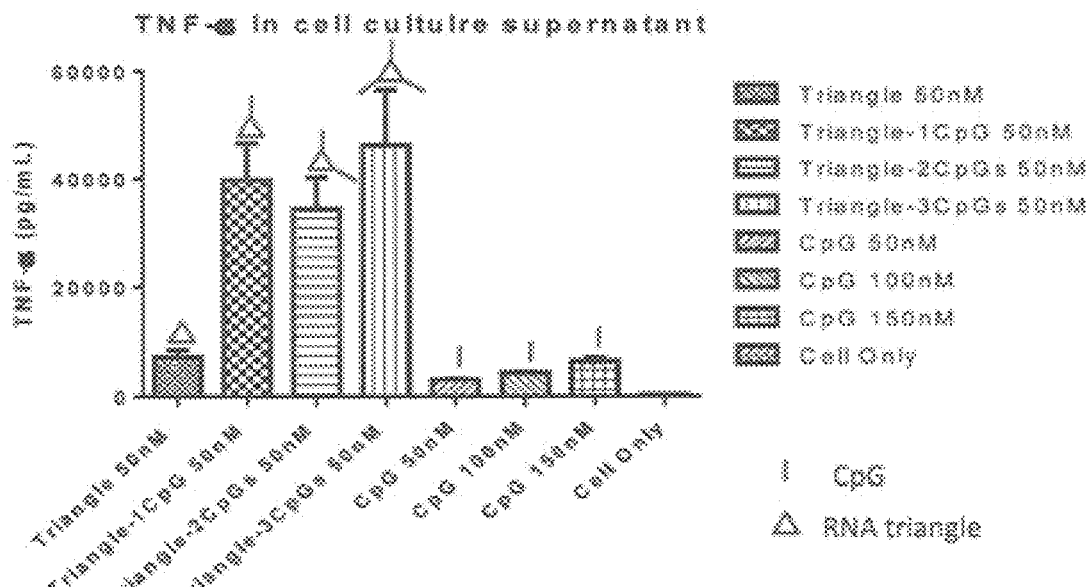
FIG. 53 shows a chart comparing TNF-alpha cytokine ELISA assay for RNA triangles harboring different numbers of CpG.
Figure 54:
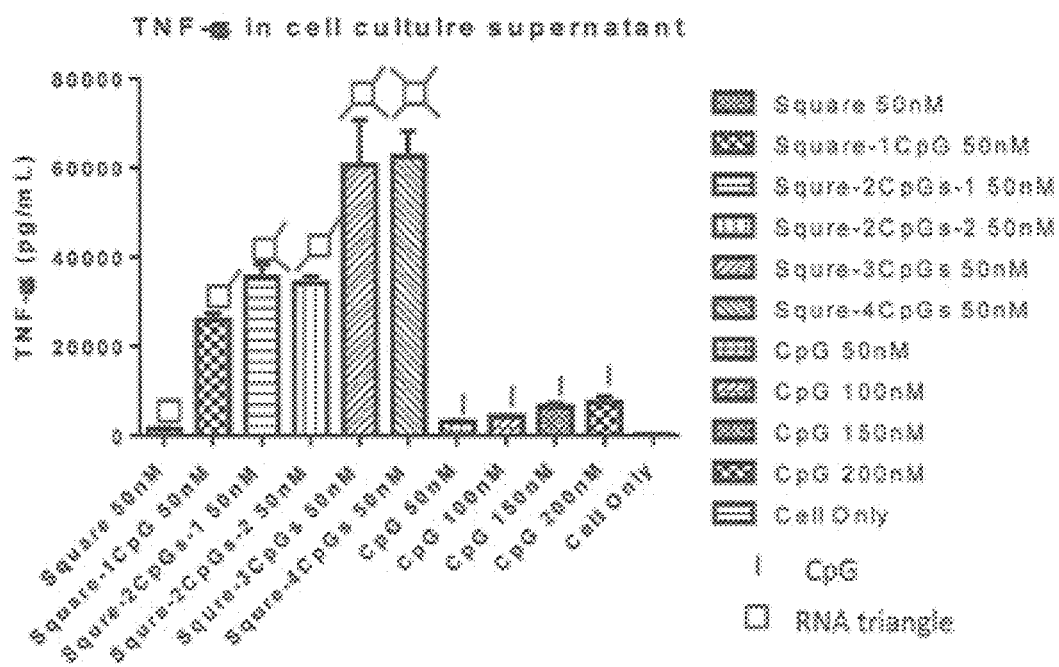
FIG. 54 shows a chart comparing TNF-alpha cytokine ELISA assay for RNA squares harboring different numbers of CpG.
Figure 55:
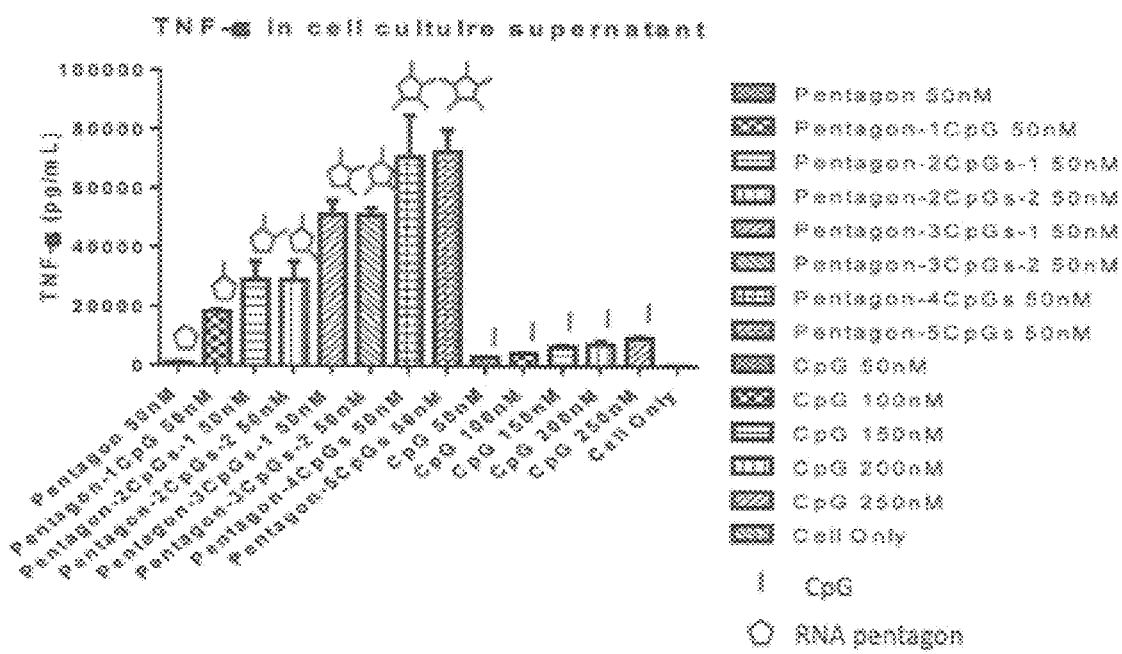
FIG. 55 shows a chart comparing TNF-alpha cytokine ELISA assay for RNA pentagons harboring different numbers of CpG.
Figure 60:
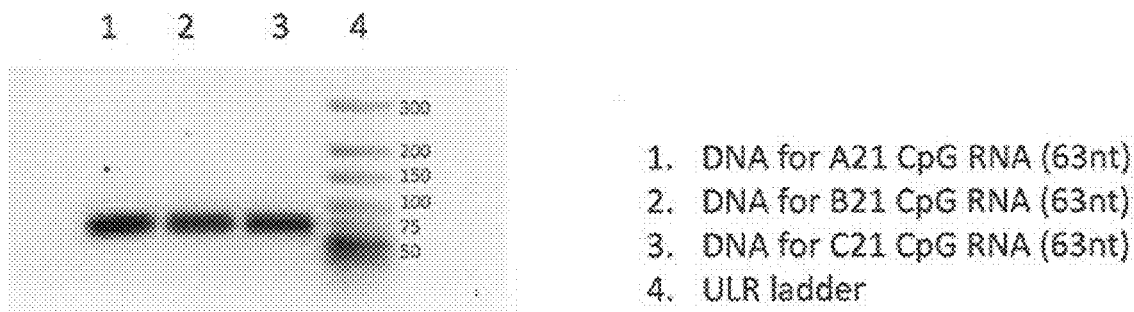
FIG. 60 shows the PCR of the DNA templates for A21, B21 and C21 CpG RNA.
Figure 61:
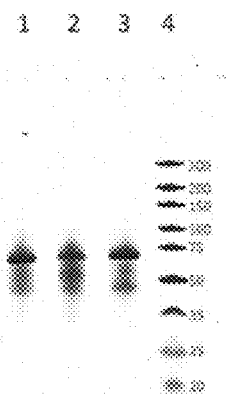
FIG. 61 shows the image of 2'F CpG RNA made by in vitro transcription.
Figure 62:
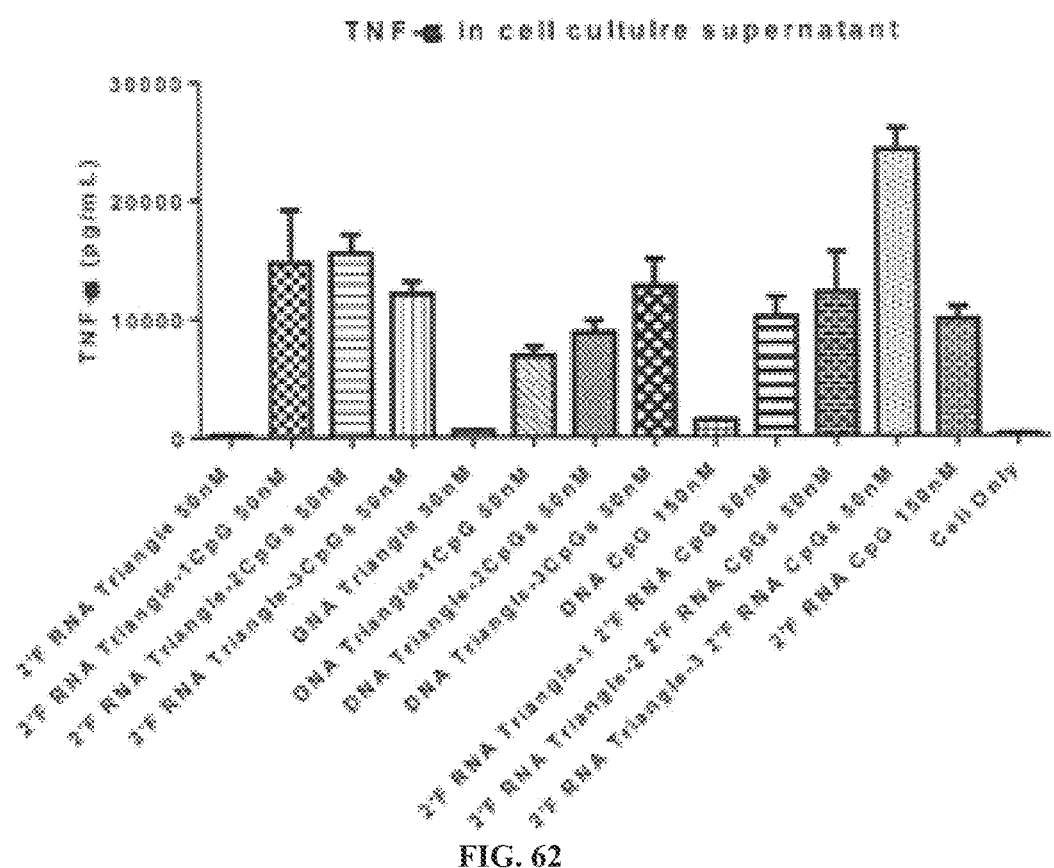
FIG. 62 shows a summary of data of the cytokine testing of 2'F RNA triangle harboring DNA CpG, DNA triangle harboring DNA CpG, and 2'F RNA triangle harboring 2'F RNA CpG.
Figure 63:
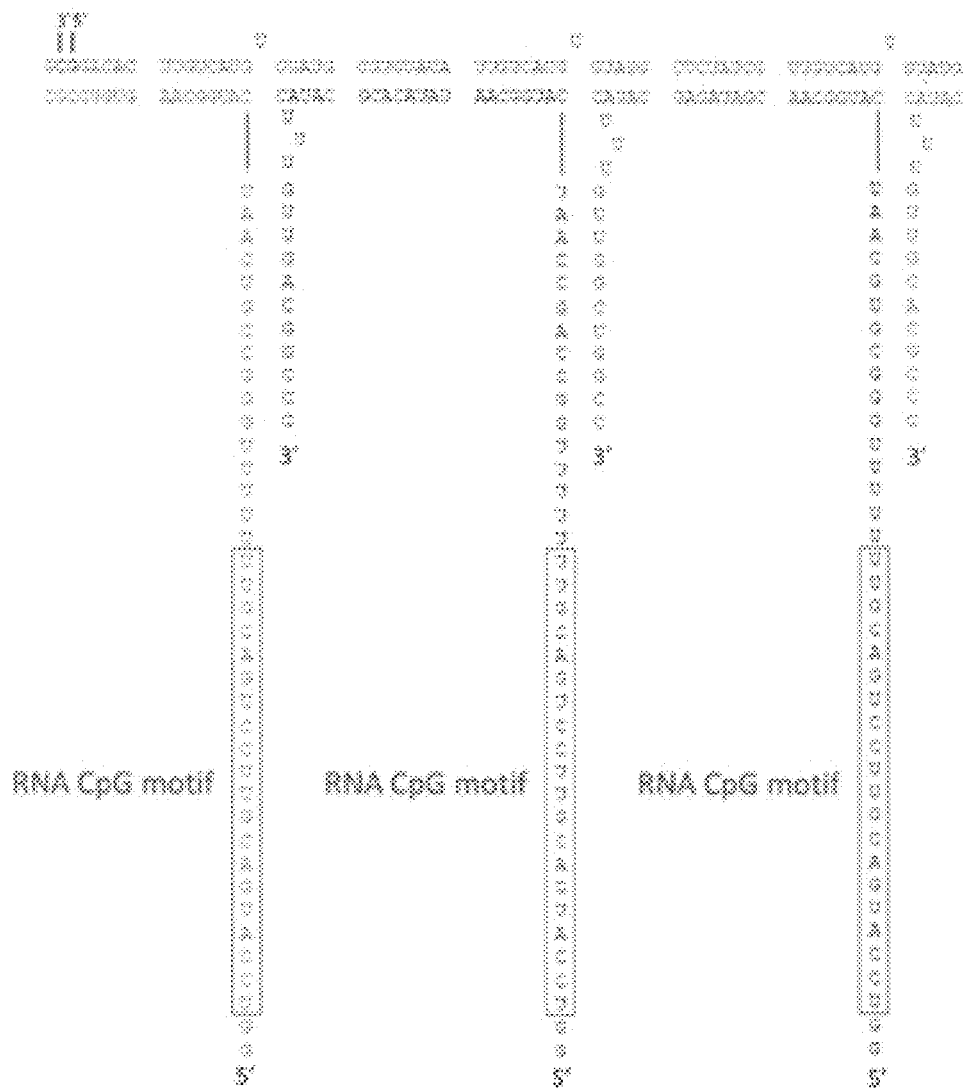
FIG. 63 shows the design of an RNA Nanostructure Triangle with RNA CpG motif. Figure discloses SEQ ID NOS 89-93, respectively, in order of appearance.

Previously, it has been demonstrated that the CpG oligonucleotide can be readily recognized by TLR9 on the endosomal membrane of macrophages, resulting in cellular uptake of the CpG adjuvants (58,59). To investigate whether there is a difference between the efficiency of RNA polygons binding to the cells, we quantified the cellular uptake of polygons-CpG using flow cytometry assay (9,10). FIG. 6A demonstrates the binding of different RNA polygon-CpG to the RAW264.7 cells in a dose-dependent manner. There was an increase in binding efficiency from triangle to pentagon with more CpGs (FIG. 14). Notably, all RNA polygons-CpG complexes remain intact after 16 h incubation in fetal bovine serum (FBS) indicating robustness of the assembled complex in extracellular environment (FIG. 15). Overall, RNA polygon-CpG complexes exhibit significantly more binding efficiency to cells compared to CpG oligonucleotides alone.

Figure 6B:
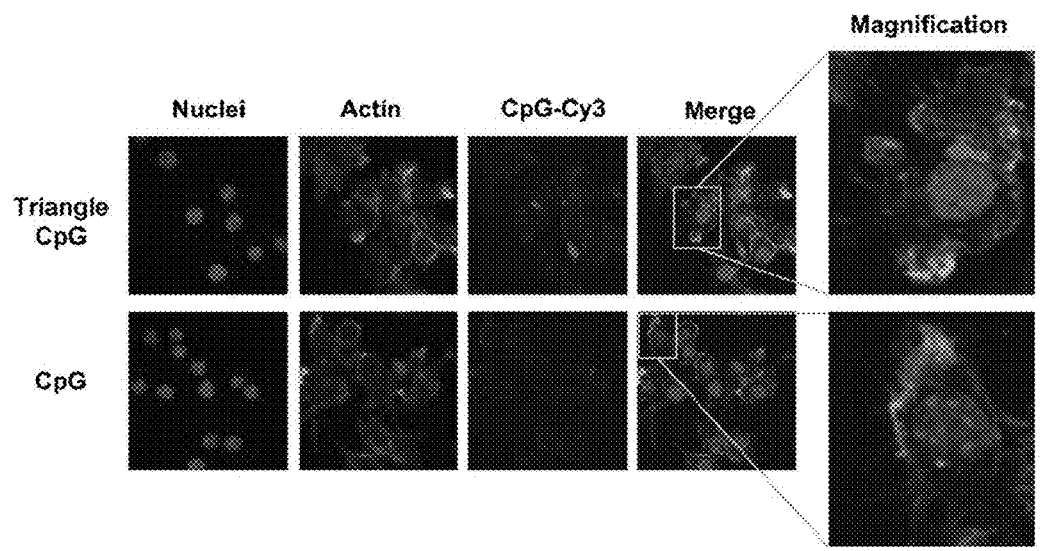

This observation was further confirmed by confocal microscopy images (FIG. 6B) revealing that RNA nanoparticle harboring CpGs are localized in the cytoplasm exclusively and that there are much higher amounts of triangular nanoparticles inside the cell compared to free CpG, suggesting that RNA nanoparticles could efficiently enhance the cellular uptake of the CpG adjuvants.

Collectively, both flow cytometry and confocal imaging demonstrated that all RNA nanoparticles with different shape and harboring CpGs have much stronger binding and cellular entry to the macrophage-like RAW 264.7 cells compared to free CpGs. In addition, cellular uptake was highly dependent on the number of CpG per polygon. With the increasing number of CpG per polygon, more efficient cell entry was observed (FIG. 5C), demonstrating the advantage of the transition from triangle to pentagon nanoparticles that can carry five CpG.

Artificial construction of RNA nanoparticles requires knowledge of the structural properties of RNA motifs, such as interhelical or intrahelical distances, X-Y and X-Y-Z angles, number and orientations of RNA branches in multi-way junctions, canonical and non-canonical interactions, binding sites for proteins, metal ions and small molecules (2, 10, 16, 25, 51, 60). Progression in RNA structural biology allowed for the analysis of RNA 3D motifs from existing RNA structures at atomic resolution and various data bases, including www.pdb.com, RNA multi-way junction (61) and find RNA motif (62). This study, based on the previously reported versatile pRNA 3WJ 3D motifs (PDB accession ID: 4KZ2) (10,51), shows that the 3WJ structure can be folded into desired conformations based on the dynamics of the 60° ∠AOC, demonstrating the ability to tune the physical and structural properties of RNA polygons for a variety of technological, biological and medicinal needs. This approach, based on the propagation of the central RNA strand used to direct the folding of corresponding short or external strands into planar triangle, square and pentagon conformations, resulted in the 60°, 90° and 108° bending of interhelical ∠AOC of the pRNA 3WJ. This is especially important for medical applications where one needs to construct different RNA nano-scaffolds based on a nontoxic and thermodynamically stable building block. The following advantages result from this technique: (i) the number and combination of therapeutic molecules can be tuned to an RNA-based nano-carrier; (ii) the nano-scaffold has a controllable size and shape and (iii) variable thermodynamic and RNase resistance properties can be applied depending on the application of the nano-scaffold.

In addition to the discovery of the unique approach for the rational design of stable RNA nanoparticles, it has been demonstrated that each RNA polygon has the potential to serve as multivalent nanocarriers of vaccine adjuvants, particularly of CpG oligodeoxynucleotides. The designed RNAs self-assemble into distinct, non-toxic homogeneous nanoparticles with high chemical, thermal and intracellular stability. We found that the size and shape of the RNA nanostructures are important factors for the induction of immunostimulatory processes in vitro and in animal models and that there is a correlation between the cytokine induction and the local CpG concentration effect. The highest level of secretion of pro-inflammatory cytokines tumor necrosis factor TNF-a, interleukin (IL)-6 was obtained with the smallest nanoparticle (triangle~9 nm size) harboring one CpG compared to square (~11 nm) and pentagon (~13 nm). However, upon increasing the numbers of CpG per RNA nanoparticle the cytokine induction was affected more by pentagon as the number or local concentration of CpG is highest in the pentagon. This study illustrates the importance of the size and shape of RNA nanoparticles for improvement of activity of CpG based vaccines targeting infectious diseases and cancer cells, as well as for increasing immune-response by the innate and adaptive immune systems. The RNA nanoparticles harboring CpGs are safe, effective, versatile and easy to manufacture, offering new solutions to address the unmet needs in current vaccines and adjuvants. Recent findings on the thermodynamically ultra-stable (10,11) and heat-resistant (18) RNA nanoparticles have expanded the potential for application of pRNA 3WJ derived nanoparticles in the fields of biomedical, nanotechnology, or polymer industries.

In FIG. 64, cytokine testing of 2'F triangle harboring CpG, DNA triangle harboring DNA CpG and 2'F triangle harboring 2'F RNA CpG shows increased TNF-α in cell culture supernatant in the 2'F Triangle harboring 2'F RNA CpG compared to 2'F triangle harboring DNA CpG and DNA triangle harboring DNA CpG.

Throughout this document, various references are mentioned. All such references are incorporated herein by reference, including the references set forth in the following list:

REFERENCES

1. Guo, P., Zhang, C., Chen, C., Trottier, M. and Garver, K. (1998) Inter-RNA interaction of phage phi29 pRNA to form a hexameric complex for viral DNA transportation. *Mol. Cell*, 2, 149-155.
2. Guo, P. (2010) The emerging field of RNA nanotechnology. *Nat. Nanotechnol.*, 5, 833-842.
3. Chen, C., Zhang, C. and Guo, P. (1999) Sequence requirement for hand-in-hand interaction in formation of pRNA dimers and hexamers to gear phi29 DNA translocation motor. *RNA*, 5, 805-818.
4. Geary, C., Chworos, A. and Jaeger, L. (2010) Promoting RNA helical stacking via A-minor junctions. *Nucleic Acids Res.*, 39, 1066-1080.
5. Grabow, W. W., Zakrevsky, P., Afonin, K. A., Chworos, A., Shapiro, B. A. and Jaeger, L. (2011) Self-assembling RNA nanorings based on RNAI/II inverse kissing complexes. *Nano Lett.*, 11, 878-887.
6. Shu, D., Moll, W. D., Deng, Z., Mao, C. and Guo, P. (2004) Bottom-up assembly of RNA arrays and superstructures as potential parts in nanotechnology. *Nano Lett.*, 4, 1717-1723.
7. Shu, Y., Haque, F., Shu, D., Li, W., Zhu, Z., Kotb, M., Lyubchenko, Y. and Guo, P. (2013) Fabrication of 14 different RNA nanoparticles for specific tumor targeting without accumulation in normal organs. *RNA*, 19, 766-777.
8. Shu, D., Huang, L., Hoeprich, S. and Guo, P. (2003) Construction of phi29 DNA-packaging RNA (pRNA) monomers, dimers and trimers with variable sizes and shapes as potential parts for nano-devices. *J. Nanosci. Nanotechnol.*, 3, 295-302.
9. Shu, Y., Shu, D., Haque, F. and Guo, P. (2013) Fabrication of pRNA nanoparticles to deliver therapeutic RNAs and bioactive compounds into tumor cells. *Nat. Protoc.*, 8, 1635-1659.
10. Shu, D., Shu, Y., Haque, F., Abdelmawla, S. and Guo, P. (2011) Thermodynamically stable RNA three-way junctions for constructing multifunctional nanoparticles for delivery of therapeutics. *Nat. Nanotechnol.*, 6, 658-667.
11. Haque, F., Shu, D., Shu, Y., Shlyakhtenko, L., Rychahou, P., Evers, M. and Guo, P. (2012) Ultrastable synergistic tetravalent RNA nanoparticles for targeting to cancers. *Nano Today*, 7, 245-257.
12. Shu, D., Zhang, L., Khisamutdinov, E. and Guo, P. (2013) Programmable folding of fusion RNA complex driven by the 3WJ motif of phi29 motor pRNA. *Nucleic Acids Res.*
13. Ponchon, L. and Dardel, F. (2007) Recombinant RNA technology: the tRNA scaffold. *Nat. Methods*, 4, 571-576.
14. Severcan, I., Geary, C., Chworos, A., Voss, N., Jacovetty, E. and Jaeger, L. (2010) A polyhedron made of tRNAs. *Nat. Chem.*, 2, 772-779.
15. Nasalean, L., Baudrey, S., Leontis, N. B. and Jaeger, L. (2006) Controlling RNA self-assembly to form filaments. *Nucleic Acids Res.*, 34, 1381-1392.
16. Novikova, I. V., Hassan, B. H., Mirzoyan, M. G. and Leontis, N. B. (2010) Engineering cooperative tecto-RNA complexes having programmable stoichiometries. *Nucleic Acids Res.*, 39, 2903-2917.
17. Ishikawa, J., Fujita, Y., Maeda, Y., Furuta, H. and Ikawa, Y. (2010) GNRA/receptor interacting modules: versatile modular units for natural and artificial RNA architectures. *Methods*, 54, 226-238.
18. Khisamutdinov, E. F., Jasinski, D. L. and Guo, P. (2014) RNA as a boiling-resistant anionic polymer material to build robust structures with defined shape and stoichiometry. *ACS Nano*
19. Afonin, K. A., Bindewald, E., Yaghoubian, A. J., Voss, N., Jacovetty, E., Shapiro, B. A. and Jaeger, L. (2010) In vitro assembly of cubic RNA-based scaffolds designed in silico. *Nat. Nanotechnol.*, 5, 676-682.
20. Ohno, H., Kobayashi, T., Kabata, R., Endo, K., Iwasa, T., Yoshimura, S. H., Takeyasu, K., Inoue, T. and Saito, H. (2011) Synthetic RNA-protein complex shaped like an equilateral triangle. *Nat. Nanotechnol.*, 6, 116-120.
21. Shapiro, B. A., Bindewald, E., Kasprzak, W. and Yingling, Y. (2008) Protocols for the in silico design of RNA nanostructures. *Methods Mol. Biol.*, 474, 93-115.
22. Lee, J. B., Hong, J., Bonner, D. K., Poon, Z. and Hammond, P. T. (2012) Self-assembled RNA interference microsponges for efficient siRNA delivery. *Nat. Mater.*, 11, 316-322.
23. Guo, P (2012) Rolling circle transcription of tandem siRNA to generate spherulitic RNA nanoparticles for cell entry. *Mol. Ther. Nucleic Acids*, 1, e36.
24. Jaeger, L., Westhof, E. and Leontis, N. B. (2001) TectoRNA: modular assembly units for the construction of RNA nano-objects. *Nucleic Acids Res.*, 29, 455-463.
25. Leontis, N. B. and Westhof, E. (2002) The annotation of RNA motifs. *Comp. Funct. Genomics*, 3, 518-524.
26. Chworos, A., Severcan, I., Koyfman, A. Y., Weinkam, P., Oroudjev, E., Hansma, H. G. and Jaeger, L. (2004) Building programmable jigsaw puzzles with RNA. *Science*, 306, 2068-2072.
27. Dibrov, S. M., McLean, J., Parsons, J. and Hermann, T. (2011) Self-assembling RNA square. *Proc. Natl. Acad. Sci. U.S.A.*, 108, 6405-6408.
28. Severcan, I., Geary, C., Verzemnieks, E., Chworos, A. and Jaeger, L. (2009) Square-shaped RNA particles from different RNA folds. *Nano Lett.*, 9, 1270-1277.
29. Garver, K. and Guo, P. (2000) Mapping the inter-RNA interaction of phage phi29 by site-specific photoaffinity crosslinking. *J. Biol. Chem.*, 275, 2817-2824.
30. Chen, C., Sheng, S., Shao, Z. and Guo, P. (2000) A dimer as a building block in assembling RNA: a hexamer that gears bacterial virus phi29 DNA-translocating machinery. *J. Biol. Chem.*, 275, 17 510-17 516.
31. Cayrol, B., Nogues, C., Dawid, A., Sagi, I., Silberzan, P. and Isambert, H. (2009) A nanostructure made of a bacterial noncoding RNA. *J. Am. Chem. Soc.*, 131, 17 270-17 276.
32. Lescoute, A. and Westhof, E. (2006) Topology of three-way junctions in folded RNAs. *RNA.*, 12, 83-93.
33. Leontis, N. B. and Westhof, E. (2003) Analysis of RNA motifs. *Curr. Opin. Struct. Biol.*, 13, 300-308.
34. Walter, F., Murchie, A. I., Duckett, D. R. and Lilley, D. M. (1998) Global structure of four-way RNA junctions studied using fluorescence resonance energy transfer. *RNA.*, 4, 719-728.
35. Lilley, D. M. (2000) Structures of helical junctions in nucleic acids. *Q. Rev. Biophys.*, 33, 109-159.
36. Batey, R. T., Rambo, R. P. and Doudna, J. A. (1999) Tertiary motifs in RNA structure and folding. *Angew. Chem. Int. Ed. Engl.*, 38, 2326-2343.
37. Binzel, D. W., Khisamutdinov, E. F. and Guo, P. (2014) Entropy-driven one-step formation of Phi29 pRNA 3WJ from three RNA fragments. *Biochemistry*, 53, 2221-2231.
38. Krieg, A. M. (2003) CpG motifs: the active ingredient in bacterial extracts? *Nat. Med.*, 9, 831-835.
39. Medzhitov, R. (2001) CpG DNA: security code for host defense. *Nat. Immunol.*, 2, 15-16.
40. Latz, E., Schoenemeyer, A., Visintin, A., Fitzgerald, K. A., Monks, B. G., Knetter, C. F., Lien, E., Nilsen, N. J., Espevik, T. and Golenbock, D. T. (2004) TLR9 signals after translocating from the ER to CpG DNA in the lysosome. *Nat. Immunol.*, 5, 190-198.
41. Hemmi, H., Takeuchi, O., Kawai, T., Kaisho, T., Sato, S., Sanjo, H., Matsumoto, M., Hoshino, K., Wagner, H., Takeda, K. et al. (2000) A toll-like receptor recognizes bacterial DNA. *Nature*, 408, 740-745.
42. Borsi, L., Carnemolla, B., Nicolo, G., Spina, B., Tanara, G. and Zardi, L. (1992) Expression of different tenascin isoforms in normal, hyperplastic and neoplastic human breast tissues. *Int. J. Cancer*, 52, 688-692.
43. Mo, J. H., Park, S. W., Rhee, C. S., Takabayashi, K., Lee, S. S., Quan, S. H., Kim, I. S., Min, Y. G., Raz, E. and Lee, C. H. (2006) Suppression of allergic response by CpG motif oligodeoxynucleotide-house-dust mite conjugate in animal model of allergic rhinitis. *Am. J. Rhinol.*, 20, 212-218.
44. Sandler, A. D., Chihara, H., Kobayashi, G., Zhu, X. Y., Miller, M. A., Scott, D. L. and Krieg, A. M. (2003) CpG oligonucleotides enhance the tumor antigen-specific immune response of a granulocyte macrophage colony-stimulating factor-based vaccine strategy in neuroblastoma. *Cancer Res.*, 63, 394-399.
45. Saha, A., Baral, R. N., Chatterjee, S. K., Mohanty, K., Pal, S., Foon, K. A., Primus, F. J., Krieg, A. M., Weiner, G. J. and Bhattacharya-Chatterjee, M. (2006) CpG oligonucleotides enhance the tumor antigen-specific immune response of an anti-idiotype antibody-based vaccine strategy in CEA transgenic mice. *Cancer Immunol. Immunother.*, 55, 515-527.
46. Winter, P. M., Morawski, A. M., Caruthers, S. D., Fuhrhop, R. W., Zhang, H., Williams, T. A., Allen, J. S., Lacy, E. K., Robertson, J. D., Lanza, G. M. et al. (2003) Molecular imaging of angiogenesis in early-stage atherosclerosis with alpha(v)beta3-integrin-targeted nanoparticles. *Circulation*, 108, 2270-2274.
47. Mohri, K., Nishikawa, M., Takahashi, N., Shiomi, T., Matsuoka, N., Ogawa, K., Endo, M., Hidaka, K., Sugiyama, H., Takahashi, Y. et al. (2012) Design and development of nanosized DNA assemblies in polypod-like structures as efficient vehicles for immunostimulatory CpG motifs to immune cells. *ACS Nano*, 6, 5931-5940.
48. Noel, A., Jost, M. and Maquoi, E. (2008) Matrix metalloproteinases at cancer tumor-host interface. *Semin. Cell Dev. Biol.*, 19, 52-60.
49. Matsuoka, N., Nishikawa, M., Mohri, K., Rattanakiat, S. and Takakura, Y. (2010) Structural and immunostimulatory properties of Y-shaped DNA consisting of phosphodiester and phosphorothioate oligodeoxynucleotides. *J. Control. Release*, 148, 311-316.
50. Narunsky, L., Oren, R., Bochner, F. and Neeman, M. (2014) Imaging aspects of the tumor stroma with therapeutic implications. *Pharmacol. Ther.*, 141, 192-208.
51. Zhang, H., Endrizzi, J. A., Shu, Y., Haque, F., Sauter, C., Shlyakhtenko, L. S., Lyubchenko, Y., Guo, P. and Chi, Y. I. (2013) Crystal structure of 3WJ core revealing divalent ion-promoted thermostability and assembly of the Phi29 hexameric motor pRNA. *RNA*, 19, 1226-1237.
52. Collins, T. J. (2007) ImageJ for microscopy. *Biotechniques*, 43, 25-30.
53. Lyubchenko, Y. L. and Shlyakhtenko, L. S. (2009) AFM for analysis of structure and dynamics of DNA and protein-DNA complexes. *Methods*, 47, 206-213.
54. Lyubchenko, Y. L., Gall, A. A., Shlyakhtenko, L. S., Harrington, R. E., Jacobs, B. L., Oden, P. I. and Lindsay, S. M. (1992) Atomic force microscopy imaging of double stranded DNA and RNA. *J. Biomol. Struct. Dyn.*, 10, 589-606.
55. Chadalavada, D. M. and Bevilacqua, P. C. (2009) Analyzing RNA and DNA folding using temperature gradient gel electrophoresis (TGGE) with application to in vitro selections. *Methods Enzymol.*, 468, 389-408.
56. Li, J., Pei, H., Zhu, B., Liang, L., Wei, M., He, Y., Chen, N., Li, D., Huang, Q. and Fan, C. H. (2011) Self-assembled multivalent DNA nanostructures for noninvasive intracellular delivery of immunostimulatory CpG oligonucleotides. *ACS Nano*, 5, 8783-8789.
57. Mohri, K., Takahashi, N., Nishikawa, M., Kusuki, E., Shiomi, T., Takahashi, Y. and Takakura, Y. (2012) Increased immunostimulatory activity of polypod-like structured DNA by ligation of the terminal loop structures. *J. Control. Release*, 163, 285-292.
58. Murphy, M. K., Piper, R. K., Greenwood, L. R., Mitch, M. G., Lamperti, P. J., Seltzer, S. M., Bales, M. J. and Phillips, M. H. (2004) Evaluation of the new cesium-131 seed for use in low-energy x-ray brachytherapy. *Med. Phys.*, 31, 1529-1538.
59. Lee, F. T., Rigopoulos, A., Hall, C., Clarke, K., Cody, S. H., Smyth, F. E., Liu, Z., Brechbiel, M. W., Hanai, N., Nice, E. C. et al. (2001) Specific localization, gamma camera imaging, and intracellular trafficking of radiolabelled chimeric anti-G(D3) ganglioside monoclonal antibody KM871 in SK-MEL-28 melanoma xenografts. *Cancer Res.*, 61, 4474-4482.
60. Afonin, K. A., Cieply, D. J. and Leontis, N. B. (2008) Specific RNA self-assembly with minimal paranemic motifs. *J. Am. Chem. Soc.*, 130, 93-102.
61. Bindewald, E., Hayes, R., Yingling, Y. G., Kasprzak, W. and Shapiro, B. A. (2008) RNA Junction: a database of RNA junctions and kissing loops for three-dimensional structural analysis and nanodesign. *Nucleic Acids Res.*, 36, D392-D397.
62. Petrov, A. I., Zirbel, C. L. and Leontis, N. B. (2011) WebFR3D—a server for finding, aligning and analyzing recurrent RNA 3D motifs. *Nucleic Acids Res.*, 39, W50-W55.

63. Shu V. Shu D, Haque F, Guo P. Fabrication of pRNA Nanoparticles to Deliver Therapeutic RNAs and Bioactive Compounds into Tumor Cells. Nature Protocols 8, 1635-1659 (2013).
64. Shu Y, Haque F, Shu D, Li W, Zhu Z, Kotb M, Lyubchenko Y, Guo P. Fabrication of 14 different RNA nanoparticles for specific tumor targeting without accumulation in normal organs. RNA. 2013 June; 19(6):767-77.
65. Reif R, Haque F, Guo P. Fluorogenic RNA Nanoparticles for Monitoring RNA Folding and Degradation in Real Time in Living Cells. Nucleic Acid Ther. 2012 December; 22(6):428-37.
66. Shu D, Shu Y, Haque F, Abdelmawla S and Guo P. 2011. Thermodynamically stable RNA three-way junction for most recent constructing multifunctional nanoparticles for delivery of therapeutics. Nature Nanotechnology. 6(10): 658-67.
67. Abdelmawla S, Guo S, Zhang L, Pulukuri S M, Patankar P, Conley P, Trebley J, Guo P, Li Q X. 2011. Pharmacological Characterization of Chemically Synthesized Monomeric phi29 pRNA Nanoparticles for Systemic Delivery. Mol Ther. 19(7):1312-22.
68. Liu J, Guo S, Cinier M, Shlyakhtenko L, Shu Y, Chen C, Shen G, and Guo P. 2011. Fabrication of Stable and RNase-Resistant RNA Nanoparticles Active in Gearing the Nanomotors for Viral DNA Packaging. ACS Nano. 5 (1), 237-45.
69. Guo P. 2010. The emerging field of RNA nanotechnology. Nature Nanotechnology. 5, 833-45.
70. Guo S, Huang F, and Guo P. 2006. Construction of folate-conjugated phage phi29 motor pRNA for delivery of chimeric siRNA to nasopharyngeal carcinoma cells. Gene Ther. 13, 814-820.
71. Khaled A, Guo S, LI F, Guo P. 2005. Controllable Self-Assembly of Nanoparticles for Specific Delivery of Multiple Therapeutic Molecules to Cancer Cells Using RNA Nanotechnology. Nano Letters. 5: 1797-1808.
72. Guo S, Tschammer N, Mohammed S and Guo P. Specific Delivery of Therapeutic RNAs to Cancer Cells via the Dimerization Mechanism of phi29 Motor pRNA. Human Gene Therapy. 2005, 16(9.) 1097-1109S.
73. U.S. Patent Application Publication No. 2009/0081157 to Kornbluth et al. for "Immunostiulatory Combinations for Vaccine Adjuvants."
74. International Patent Application Publication No. WO 2005/003293 to Guo et al. for "pRNA Chimera."
75. International Patent Application Publication No. WO 2012/170372 to Guo for "pRNA Multivalent Junction Domain for Use in Stable Multivalent RNA Nanoparticles."

All publications, patents, and patent applications mentioned in this specification, including the Appendixes, are herein incorporated by reference to the same extent as if each individual publication, patent, or patent application was specifically and individually indicated to be incorporated by reference.

SEQUENCE LISTING

```
<160> NUMBER OF SEQ ID NOS: 93

<210> SEQ ID NO 1
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggagccguc aaucauggca aguguccgcc auacuuuguu gcacgcac                48

<210> SEQ ID NO 2
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gggagcgugc aaucauggca acgauagagc auacuuuguu ggcuggac                48

<210> SEQ ID NO 3
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggaccagcc aaucauggca auauacacgc auacuuuguu gacggcgg                48
```

```
<210> SEQ ID NO 4
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggacacuugu cauguguaug cguguauauu gucaugugua ugcucuaucg uugucaugug      60
uauggc                                                                66

<210> SEQ ID NO 5
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggagccguc aaucauggca aguguccgcc auacuuuguu gcacgcac                  48

<210> SEQ ID NO 6
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggagcgugc aaucauggca agcgcaucgc auacuuuguu gcgaccua                  48

<210> SEQ ID NO 7
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gggaggucgc aaucauggca acgauagagc auacuuuguu ggcuggac                  48

<210> SEQ ID NO 8
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggaccagcc aaucauggca auauacacgc auacuuuguu gacggcgg                  48

<210> SEQ ID NO 9
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ggacacuugu cauguguaug cguguauauu gucaugugua ugcucuaucg uugucaugug      60
```
uaugcgaugc gcuugucaug uguauggc                                              88

<210> SEQ ID NO 10
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gggagccguc aaucauggca aguguccgcc auacuuuguu guagggca                        48

<210> SEQ ID NO 11
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gggacccuac aaucauggca aauaugcgcc auacuuuguu gcacgcac                        48

<210> SEQ ID NO 12
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gggagcgugc aaucauggca agcgcaucgc auacuuuguu gcgaccua                        48

<210> SEQ ID NO 13
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gggaggucgc aaucauggca acgauagagc auacuuuguu ggcuggag                        48

<210> SEQ ID NO 14
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gggaccagcc aaucauggca auauacacgc auacuuuguu gacggcgg                        48

<210> SEQ ID NO 15
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 15
ggacacuugu cauguguaug cguguauauu gucaugugua ugcucuaucg uugucaugug           60
uaugcgaugc gcuugucaug uguauggcgc auauuuguca uguguauggc    110

<210> SEQ ID NO 16
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uccaugacgu uccugacguu uuuuuacag ucguauugca uuccga    46

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tccatgacgt tcctgacgtt tttttacag tcgtattgca ttccga    46

<210> SEQ ID NO 18
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uccaugacgu uccugacguu uuuuccaua ccgccauuuc caacua    46

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tccatgacgt tcctgacgtt tttttccata ccgccatttc caacta    46

<210> SEQ ID NO 20
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uccaugacgu uccugacguu uuuuuaagca caugcgaugu uuaacu    46

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tccatgacgt tcctgacgtt tttttaagca catgcgatgt ttaact          46

<210> SEQ ID NO 22
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gguccaugac guuccugacg uuuuuuuggg ccgucaauca uggcaagugu ccgccauacu   60
uuguugcacg ccc                                                      73

<210> SEQ ID NO 23
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gguccaugac guuccugacg uuuuuuuggg cgugcaauca uggcaacgau agagcauacu   60
uuguuggcug gcc                                                      73

<210> SEQ ID NO 24
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gguccaugac guuccugacg uuuuuuuggc cagccaauca uggcaauaua cacgcauacu   60
uuguugacgg ccc                                                      73

<210> SEQ ID NO 25
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
taatacgact cactatatcc atgacgttcc tgacgttttt tttacagtcg tattgcattc   60
cga                                                                 63

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taatacgact cactatatcc atgacgttcc tgacgttt                           38

<210> SEQ ID NO 27
<211> LENGTH: 37
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 27
tcggaatgca atacgactgt aaaaaaaacg tcaggaa                              37

<210> SEQ ID NO 28
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
taatacgact cactatatcc atgacgttcc tgacgttttt ttccataccg ccatttccaa     60
cta                                                                  63

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
taatacgact cactatatcc atgacgttcc tgacgttt                             38

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tagttggaaa tggcggtatg gaaaaaaacg tcaggaa                              37

<210> SEQ ID NO 31
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
taatacgact cactatatcc atgacgttcc tgacgttttt ttaagcacat gcgatgttta     60
act                                                                  63

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
taatacgact cactatatcc atgacgttcc tgacgttt                             38
```

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
agttaaacat cgcatgtgct taaaaaaacg tcaggaa                37

<210> SEQ ID NO 34
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 34
uugucaugug uaug                14

<210> SEQ ID NO 35
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 35
cauacuuugu uga                13

<210> SEQ ID NO 36
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 36
ucaaucaugg caa                13

<210> SEQ ID NO 37
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 37
gggagccguc aaucauggca aguguccgcc auacuuuguu gcacgcac                48

<210> SEQ ID NO 38
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 38
gggagcgugc aaucauggca acgauagagc auacuuuguu ggcuggac                48

<210> SEQ ID NO 39

```
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
gggaccagcc aaucauggca auauacacgc auacuuuguu gacggcgg                48

<210> SEQ ID NO 40
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggacacuugu cauguguaug cguguauauu gucaugugua ugcucuaucg uugucaugug    60
uauggc                                                              66

<210> SEQ ID NO 41
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gggagccguc aaucauggca aguguccgcc auacuuuguu gcacgcac                48

<210> SEQ ID NO 42
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gggagcgugc aaucauggca agcgcaucgc auacuuuguu gcgaccua                48

<210> SEQ ID NO 43
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gggaggucgc aaucauggca acgauagagc auacuuuguu ggcuggac                48

<210> SEQ ID NO 44
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gggaccagcc aaucauggca auauacacgc auacuuuguu gacggcgg                48
```

```
<210> SEQ ID NO 45
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ggacacuugu cauguguaug cguguauauu gucaugugua ugcucuaucg uugucaugug      60
uaugcgaugc gcuugucaug uguauggc                                        88

<210> SEQ ID NO 46
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gggagccguc aaucauggca aguuccgcc auacuuuguu guagggca                   48

<210> SEQ ID NO 47
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gggacccuac aaucauggca aauaugcgcc auacuuuguu gcacgcac                   48

<210> SEQ ID NO 48
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gggagcgugc aaucauggca agcgcaucgc auacuuuguu gcgaccua                   48

<210> SEQ ID NO 49
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gggaggucgc aaucauggca acgauagagc auacuuuguu ggcuggag                   48

<210> SEQ ID NO 50
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gggaccagcc aaucauggca auauacacgc auacuuuguu gacggcgg                   48
```

<210> SEQ ID NO 51
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 51
ggacacuugu cauguguaug cguguauauu gucaugugua ugcucuaucg uugucaugug    60
uaugcgaugc gcuugucaug uguauggcgc auauuuguca uguguauggc              110

<210> SEQ ID NO 52
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tccatgacgt tcctgacgtt tttttaagca catgcgatgt ttaact                  46

<210> SEQ ID NO 53
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gggagccguc aaucauggca aguguccgcc auacuuuguu gcacgcucuc ucggaaugca    60
auacgacugu a                                                        71

<210> SEQ ID NO 54
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tccatgacgt tcctgacgtt tttttacag tcgtattgca ttccga                   46

<210> SEQ ID NO 55
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gggagcgugc aaucauggca acgauagagc auacuuuguu ggcuggucuc uaguuggaaa    60
uggcgguaug g                                                        71

<210> SEQ ID NO 56
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tccatgacgt tcctgacgtt tttttccata ccgccatttc caacta      46

<210> SEQ ID NO 57
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gggaccagcc aaucauggca auauacacgc auacuuuguu gacggcucuc aguuaaacau     60
cgcaugugcu u                                                         71

<210> SEQ ID NO 58
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ggacacuugu cauguguaug cguguauauu gucaugugua ugcucuaucg uugucaugug     60
uauggc                                                               66

<210> SEQ ID NO 59
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tccatgacgt tcctgacgtt tttttaagca catgcgatgt ttaact         46

<210> SEQ ID NO 60
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gggagccguc aaucauggca aguuccgcc auacuuuguu gcacgcucuc ucggaaugca      60
auacgacugu a                                                         71

<210> SEQ ID NO 61
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tccatgacgt tcctgacgtt tttttttacag tcgtattgca ttccga        46

<210> SEQ ID NO 62
<211> LENGTH: 71

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gggagcgugc aaucauggca agcgcaucgc auacuuuguu gcgaccucuc auugaucuau       60
gaucguacga u                                                            71

<210> SEQ ID NO 63
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tccatgacgt tcctgacgtt tttttatcgt acgatcatag atcaat                      46

<210> SEQ ID NO 64
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gggaggucgc aaucauggca acgauagagc auacuuuguu ggcuggucuc uaguuggaaa       60
uggcgguaug g                                                            71

<210> SEQ ID NO 65
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 65
tccatgacgt tcctgacgtt tttttccata ccgccatttc caactaggga ccagccaauc       60
auggcaauau acacgcauac uuuguugacg gcucucaguu aaacaucgca ugcuu           117

<210> SEQ ID NO 66
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ggacacuugu cauguguaug cguguauauu gucaugugua ugcucuaucg uugucaugug       60
uaugcgaugc gcuugucaug uguauggc                                          88

<210> SEQ ID NO 67
<211> LENGTH: 46
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 67
tccatgacgt tcctgacgtt tttttaagca catgcgatgt ttaact                    46

<210> SEQ ID NO 68
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gggagccguc aaucauggca aguguccgcc auacuuuguu guagggucuc auguuaagua     60
acgucuagaa u                                                          71

<210> SEQ ID NO 69
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tccatgacgt tcctgacgtt tttttattct agacgttact taacat                    46

<210> SEQ ID NO 70
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gggacccuac aaucauggca aauaugcgcc auacuuuguu gcacgcucuc gaaagcuugu     60
agcuauaguu a                                                          71

<210> SEQ ID NO 71
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tccatgacgt tcctgacgtt tttttaact atagctacaa gctttc                     46

<210> SEQ ID NO 72
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gggagcgugc aaucauggca agcgcaucgc auacuuuguu gcgaccucuc auugaucuau     60
gaucguacga u                                                          71

<210> SEQ ID NO 73
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
tccatgacgt tcctgacgtt tttttatcgt acgatcatag atcaat        46

<210> SEQ ID NO 74
<211> LENGTH: 71
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
gggaggucgc aaucauggca acgauagagc auacuuguu ggcuggucuc uaguuggaaa        60
uggcgguaug g        71

<210> SEQ ID NO 75
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
tccatgacgt tcctgacgtt tttttccata ccgccatttc caacta        46

<210> SEQ ID NO 76
<211> LENGTH: 71
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
gggaccagcc aaucauggca auauacacgc auacuuguu gacggcucuc aguuaaacau        60
cgcaugugcu u        71

<210> SEQ ID NO 77
<211> LENGTH: 110
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 77
ggacacuugu cauguguaug cguguauauu gucaugugua ugcucuaucg uugucaugug        60
uaugcgaugc gcuugucaug uguauggcgc auauuuguca uguguauggc        110

<210> SEQ ID NO 78
<211> LENGTH: 64
<212> TYPE: RNA
<213> ORGANISM: Artificial Sequence
<220> FEATURE:
<223> OTHER INFORMATION: Description of Artificial Sequence: Synthetic oligonucleotide

```
<400> SEQUENCE: 78
ggacacuugu cauguguaug cguguauauu gucaugugua ugcucuaucg uugucaugug    60
uaug                                                                64

<210> SEQ ID NO 79
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gggccgucaa ucauggcaag uguccgc                                       27

<210> SEQ ID NO 80
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ggccagccaa ucauggcaau auacacgcau acuuuguuga cggccc                  46

<210> SEQ ID NO 81
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gggcgugcaa ucauggcaac gauagagcau acuuuguugg cuggcc                  46

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cauacuuugu ugcacgccc                                                19

<210> SEQ ID NO 83
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
gggccgucaa ucauggcaag uguccgccau acuuuguugc acgcccucgg aaugcaauac    60
gacugua                                                             67

<210> SEQ ID NO 84
<211> LENGTH: 67
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 84
gggcgugcaa ucauggcaac gauagagcau acuuguugg cuggccuagu uggaaauggc    60
gguaugg                                                             67

<210> SEQ ID NO 85
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
ggccagccaa ucauggcaau auacacgcau acuuguuga cggcccaguu aaacaucgca    60
ugugcuu                                                             67

<210> SEQ ID NO 86
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
tccatgacgt tcctgacgtt tttttuugcc auguguaugu ggg                     43

<210> SEQ ID NO 87
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ggaucaauca uggcaa                                                   16

<210> SEQ ID NO 88
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
tccatgacgt tcctgacgtt tttttcccac auacuuuguu gaucc                   45

<210> SEQ ID NO 89
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89

```
ggacacuugu cauguguaug cguguauauu gucaugugua ugcucu

7. The nanostructure of claim 1, further comprising at least one adjuvant, antigen, and/or targeting ligand.

8. The nanostructure of claim 1, wherein the nanostructure induces an immune response.

9. The nanostructure of claim 8, wherein the immune response increases cytokine at least ten fold as compared to the adjuvant, the antigen, and/or the targeting ligand provided independently of the RNA nanostructure.

10. The nanostructure of claim 7, wherein the antigen is derived from a bacteria, virus, or cell.

11. The nanostructure of claim 7, wherein the antigen binds to a neutralizing antibody or an inhibitory antibody.

12. The nanostructure of claim 7, wherein the antigen is selected from B-cell epitope, T-cell epitope, T-helper epitope, epitopes derived from PG120, gp4leptopes, glycans, peptides, T-helper peptides, and streptavidin.

13. The nanostructure of claim 7, wherein the targeting ligand is selected from an aptamer, a cell surface marker, folate, siRNA and shRNA.

14. The nanostructure of claim 7, wherein the targeting ligand targets B cells, T cells, dendritic cells, macrophages, and/or cancer cells.

15. A composition, comprising: (a) an RNA nanostructure, wherein the RNA nanostructure is selected from RNA nanostructure of claim 1, RNA three-way junction, and RNA four-way junction, and wherein the RNA nanostructure contains a stretched intrahelical angle between HI and H2; and (b) an adjuvant, an antigen, and/or a targeting ligand.

16. The composition of claim 15, wherein the adjuvant is a composition comprising: (a) an RNA-oligonucleotide, wherein the RNA-oligonucleotide comprises single-stranded or double stranded oligonucleotide, and wherein RNA-oligonucleotide is about 8-50 bases in length; and (b) an immunostimulatory motif, wherein the immunostimulatory motif is conjugated to the RNA-oligonucleotide.

* * * * *